(12) United States Patent
Huang et al.

(10) Patent No.: US 9,879,294 B2
(45) Date of Patent: Jan. 30, 2018

(54) METHODS FOR DEGRADING OR CONVERTING CELLULOSIC MATERIAL

(75) Inventors: Hongzhi Huang, Beijing (CN); Haiyu Ren, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 165 days.

(21) Appl. No.: 13/982,857

(22) PCT Filed: Mar. 26, 2012

(86) PCT No.: PCT/CN2012/073040
§ 371 (c)(1),
(2), (4) Date: Jul. 31, 2013

(87) PCT Pub. No.: WO2012/130120
PCT Pub. Date: Oct. 4, 2012

(65) Prior Publication Data
US 2013/0309723 A1 Nov. 21, 2013

Related U.S. Application Data

(60) Provisional application No. 61/477,418, filed on Apr. 20, 2011.

(30) Foreign Application Priority Data

Mar. 25, 2011 (WO) ................ PCT/CN2011/072143
Dec. 19, 2011 (WO) ................ PCT/CN2011/084230

(51) Int. Cl.
| | |
|---|---|
| *C12P 7/00* | (2006.01) |
| *C12N 9/08* | (2006.01) |
| *C12N 9/42* | (2006.01) |
| *C12P 21/04* | (2006.01) |
| *C07H 21/04* | (2006.01) |
| *C12P 19/00* | (2006.01) |
| *C12P 19/14* | (2006.01) |
| *C12P 5/00* | (2006.01) |
| *C12P 7/02* | (2006.01) |
| *C12P 7/26* | (2006.01) |
| *C12P 7/40* | (2006.01) |
| *C12P 13/04* | (2006.01) |

(52) U.S. Cl.
CPC ............ *C12P 19/00* (2013.01); *C12N 9/0065* (2013.01); *C12N 9/2437* (2013.01); *C12P 5/00* (2013.01); *C12P 7/02* (2013.01); *C12P 7/26* (2013.01); *C12P 7/40* (2013.01); *C12P 13/04* (2013.01); *C12P 19/14* (2013.01); *C12Y 111/01006* (2013.01)

(58) Field of Classification Search
CPC ................................ C12N 9/0065; C12P 5/00
See application file for complete search history.

(56) References Cited

U.S. PATENT DOCUMENTS 9,637,725 B2 * 5/2017 Liu ...................... C12N 9/0065

FOREIGN PATENT DOCUMENTS

| | | |
|---|---|---|
| JP | 2004261137 | 9/2004 |
| WO | 2007/019442 A2 | 2/2007 |
| WO | 2007/089290 A2 | 8/2007 |
| WO | 2009/042871 A1 | 4/2009 |
| WO | 2010/080408 A2 | 7/2010 |
| WO | 2013/091547 A1 | 6/2013 |

OTHER PUBLICATIONS

Branden et al. Introduction to Protein Structure, Garland Publishing Inc., New York, p. 247, 1991.*
Kumar et al. Biocatalytic Conversion of Renewable Reedstocks to Industrial Chemials. ACS. pp. 363-376. 2004.*
Scott. Catalase improves saccharification of lignocellulose by reducing lytic polysaccharide monooxygenase-associated enzyme inactivation. Biotechnol Lett (2016) 38:425-434.*
Chance et al., Methods in Enzymology, vol. 2, pp. 764-791 (1955).
Fedorova et al., NCBI Accession No. XP_002487825 (2009).
Johnson et al., GenBank Accession No. ABH85895.1 (2006).
Moyer, GenBank Accession No. AAB76420.1 (1997).
Nierman et al., NCBI Accession No. XP_748550 (2008).

* cited by examiner

*Primary Examiner* — Yong Pak
(74) *Attorney, Agent, or Firm* — Elias Lambiris

(57) ABSTRACT

Provided are methods for degrading or converting a cellulosic material, comprising: treating the cellulosic material with an enzyme composition in the presence of a polypeptide having catalase activity; and enzyme composition used for degrading or converting a cellulosic material comprising one or more (e.g., several) enzymes having cellulolytic and/or hemicellulolytic activity and a polypeptide having catalase activity.

11 Claims, 6 Drawing Sheets

```
            M   R   G   A   Y   S   L   G   A   F   A   S   L   I   A   V   A   S   A   A
   1    atgcgaggggcatactctctcggcgcctttgccagtctcatcgcggtagcttcggctgcc
            C   P   M   L   T   G   E   I   P   A   G   S   I   A   N   P   H   H   L   G
  61    tgcccaatgctgactggcgaaatcccagcaggcagcattgcaaaccctcatcaccttgga
            S   R   A   D   S   N   A   S   D   E   T   E   A   F   L   S   E   F   Y   L
 121    agccgcgctgactcgaatgcttccgacgaaacagaagcctttctgtccgaattctacctt
            N   D   N   N   S   F   L   T   T   D   V   G   G   P   I   E   D   Q   N   S
 181    aatgacaacaacagcttcctcactaccgatgtgggcggcccgatagaagaccaaaacagt
            L   K   A   G   I   R   G   S   T   L   L   E   D   F   I   F   R   Q   K   I
 241    ctcaaggccggcattcgcggatcaacgctcttggaggatttcatctttcgccagaagatt
            Q   R   F   D   H   E   R
 301    cagcgctttgatcacgagcgtGTAAGTTCTTGAAATCATATGACTACTTCGATGTGTACT
                            V   P   E   R   A   V   H   A   R   G   A   G   A   H   G   V
 361    TACGACTTCTAGgtgcccgaacgcgctgtgcatgctcgaggtgctggtgctcatggtgta
            F   T   S   Y   A   D   W   S   N   I   T   A   A   S   F   L   G   A   A   G
 421    ttcacatcgtatgctgattggtccaacatcaccgctgcttcattcctaggagctgccgga
            K   E   T   P   T   F   V   R   F   S   T   V   A   G   S   R   G   S   A   D
 481    aaggaaacgcccacctttgtacgcttctcgactgttgccggcagtcgtggtagtgccgat
            T   A   R   D   V   H   G   F   A   T   R   F   Y   T   D   E   G   N   Y
 541    accgctcgtgatgttcacggctttgctacccgcttctatactgacgaaggcaactacgGT
                                                                    D   I   V   G
 601    AAGATCTATCCATGGTCATAGCAGCCTATACATTTGCTAACTCACAGCAGatatcgttgg
            N   N   I   P   V   F   F   I   Q   D   A   I   Q   F   P   D   L   I   H   A
 661    aaacaacattcccgtcttcttcatccaagacgctattcagttccctgacctcattcatgc
            V   K   P   Q   P   A   S   E   I   P   Q   A   A   T   A   H   D   T   A   Y
 721    agtcaagccacagccagccagtgaaatcccacaggccgctactgcccacgacactgctta
            D   F   F   G   Q   Q   P   S   T   L   H   T   L   F   W   A   M   A   G   H
 781    tgatttcttcggccagcagcctagtaccttgcatacccttttctgggcaatggcaggtca
            G   I   P   R   S   F   R   H   V   D   G   F   G   V   H   A   Y   R   F   V
 841    tggtatcccgcggtcttccgccatgttgacggattcggcgttcacgcttaccgatttgt
            T   D   D   G   S   S   K   L   V   K   F   H   W   K   S   L   Q   G   R   A
 901    gactgacgacggctcttcaaagctagtcaaattccactggaagtccttacagggtcgtgc
            S   L   V   W   E   E   A   Q   A   T   A   G   K   N   A   D   F   M   R   Q
 961    aagcttagtctgggaagaagctcaagccactgctggcaagaatgctgatttcatgaggca
            D   L   F   D   N   I   A   A   G   R   Y   P   E   W   E
1021    agatctgtttgacaatattgcagctggccggtacccagaatgggagGTGAGTATAAGTTG
                                                            L   G   V   Q   L   I   E   E   P
1081    CCTGTCCTCCGAAGAATTTCACTAACATGAATAGctcggcgtgcaacttatcgaggaacc
            D   Q   L   S   Y   G   F   D   L   L   D   P   T   K   I   L   P   V   E   Q
1141    agaccagctcagctacggatttgatctgcttgatccaccaagatactcccagttgaaca
            V   P   I   T   P   L   G   K   M   Q   L   N   R   N   P   L   N   Y   F   A
1201    agttccaatcaccccgctcggaaaaatgcaactcaaccgtaacccgctaaactactttgc
            E   T   E   Q   V   M
1261    tgagaccgagcaagtaatgGTACGTTAACTTCTCTTCTCCCCCTCCCCCCAAACAACTCC
                                                    F   Q   P   G   H   I   V   R   G   I   D
1321    GGGTACAGCTCATGCTGATCATTTTAGttccaacctggtcacattgttcgtggcattgat
            F   T   E   D   P   L   L   Q   G   R   L   F   S   Y   L   D   T   Q   L   N
1381    ttcacagaggaccctcttctccaaggccgtctattttcttacctcgacactcagcttaat
            R   N   G   G   P   N   F   E   Q   I   P   I   N   R   P   R   V   P   I   H
1441    cgcaacggtggccccaactttgagcagattccgatcaaccgtcctcgtgttcctatccac
            N   N   N   R   D   G   F   G   Q   M   F   I   P   L   N   D   A   A   Y   S
1501    aataacaaccgagacggttttggccagatgtttattccactcaacgatgcggcatactcg
```

Fig. 1

```
           P  N  T  L  S  D  G  N  P  K  Q  A  N  E  T  V  G  N  G  F
1561  ccaaacaccctaagcgatggcaaccctaagcaggcaaatgagactgttggaaatggtttc
       F  T  T  P  G  R  T  A  N  G  N  L  V  R  A  K  S  P  T  F
1621  tttactactccaggacgcactgccaatggaaacctcgtccgcgccaaaagcccaacgttt
       A  D  V  W  S  Q  P  G  L  F  Y  N  S  L  T  A  T  E  Q  Q
1681  gcggatgtgtggtcccaacctggcctcttttacaactccttgacagccaccgaacaacag
       F  V  I  N  A  L  R  F  E  L  A  N  V  A  S  E  T  V  K  N
1741  tttgtcatcaatgctctgcggttcgagctagccaatgtagcaagtgagactgtgaagaat
       N  F  I  T  Q  I  N  R  V  N  N  T  L  A  T  L  V  A  T  A
1801  aacttcatcacccagatcaatcgcgtaaacaacaccttggcaacacttgtagccactgca
       I  G  V  N  A  P  E  P  D  P  T  Y  Y  H  H  N  K  T  S  D
1861  attggtgtcaatgctcctgaacccgacccgacttactaccaccacaacaagacgtctgat
       V  G  T  F  G  T  P  L  K  K  I  D  G  L  K  V  G  V  L  A
1921  gtgggaacattcggtactcctctgaagaagattgatggtctcaaggtcggagtccttgct
       S  V  N  D  E  N  S  I  S  E  G  Q  S  L  A  R  S  L  A  D
1981  tctgtcaacgatgaaaacagtatttccgagggacagtctctagcacgaagcttggcggat
       L  N  V  D  V  V  I  V  A  E  R  L  A  G  N  V  S  A  T  Y
2041  ttgaatgtggacgtcgttattgtcgctgaacgacttgctggtaatgtctcagctacatac
       S  A  S  D  A  I  N  F  D  A  V  I  V  T  S  G  A  K  G  L
2101  tccgcatctgacgctatcaacttcgatgctgttattgtcacttcaggggctaagggtctc
       F  G  P  Q  T  F  T  A  V  S  N  T  T  L  Y  P  V  G  R  P
2161  tttggacctcaaaccttcaccgccgtatccaacaccactctttatcccgtgggccgtccc
       T  Q  I  L  V  D  A  F  R  Y  G  K  P  V  G  A  V  G  S  A
2221  acgcagattttggtcgacgcttccgctacggcaagccggttggagcagtgggtagtgca
       S  E  A  L  T  V  S  D  I  D  T  D  R  S  G  V  I  T  G  D
2281  agcgaagcgctgactgtttcggacattgatactgaccgcagtggtgtgattactggtgat
       L  N  D  E  F  V  K  Q  L  S  E  D  L  A  T  F  K  F  L  D
2341  ttgaacgacgagtttgtgaagcaactgtcggaggaccttgcaacattcaagttcttggac
       R  F  T  V  D  E  *
2401  cgcttcaccgtcgacgagtag
```

Fig. 1 continued

```
            M  N  R  V  T  N  L  L  A  W  A  G  A  I  G  L  A  Q  A  T
   1 atgaacagagtcacgaatctcctcgcctgggccggcgcgatagggctcgcccaagcaaca
            C  P  F  A  D  P  A  A  L  Y  R  R  Q  D  T  T  S  G  Q  S
  61 tgccccttttgcggaccctgccgctctgtataggcgtcaagatactaccagcggccagtcg
            P  L  A  A  Y  E  V  D  D  S  T  G  Y  L  T  S  D  V  G  G
 121 ccacttgcagcatacgaggtggatgacagcaccggatacctgacctccgatgttggcggg
            P  I  Q  D  Q  T  S  L  K  A  G  I  R  G  P  T  L  L  E  D
 181 cccattcaggaccagaccagcctcaaggcaggcatccgggtccgaccttcttgaggac
            F  M  F  R  Q  K  I  Q  H  F  D  H  E  R
 241 tttatgttccgccagaagatccagcacttcgaccatgaacggGTAAGGACATAATGCTCA 301 CACGAGCGGCTGCGTACCTATTTATTTCCGAGACATTGGGCTGGCTGGCTGGCTGTGACT
                                                              V  P
 361 GCCTGAGTTTGGGGACATACGGAGTACCTTACTGACGCGCTGATCCACTCCAGgttcccg
         E  R  A  V  H  A  R  G  A  G  A  H  G  T  F  T  S  Y  A  D
 421 aaagggcggtccatgctcgaggcgctggagcacacgggaccttcacgagttacgccgact
         W  S  N  I  T  A  A  S  F  L  N  A  T  G  K  Q  T  P  V  F
 481 ggagtaacatcacagcggcgtcctttctgaacgccacaggaaagcagacgccggtgtttg
         V  R  F  S  T  V  A  G  S  R  G  S  A  D  T  A  R  D  V  H
 541 tccggttctcgaccgttgctgggtctcgagggagcgcagacacggcgagagacgttcatg
         G  F  A  T  R  F
 601 gtttcgcgacgcggttGTAAGTTTTGTTGTGTTTCATTCGTTCCGGTCTGTAGAGGAGGG
                                                           Y  T  D  E
 661 TTAGGATATGAGCTAATGTGTGTGTGTGTGTGTGTGTGTGTGAAGttacactgatgaa
         G  N  F
 721 ggcaactttgGTACGTCCCATGCATGGTCCTCAATTCTCTTATCTGGCAGCGATGTGGTC
                                         D  I  V  G  N  N  I  P  V  F  F  I
 781 ATTGTCGACGTTGCTAACTTGCGTAGatatcgtcggaaacaacatcccggtattcttcat
         Q  D  A  I  Q  F  P  D  L  I  H  S  V  K  P  R  P  D  N  E
 841 tcaagatgcaatccagttccctgaccttatccactcggtcaagccgcgtcccgacaacga
         I  P  Q  A  A  T  A  H  D  S  A  W  D  F  F  S  Q  Q  P  S
 901 gattccccaagcggcgacggctcatgattcagcttgggacttcttcagccagcagccaag
         T  M
 961 caccatgGTAAGCAATGGACCAAGGAGCCGCACCTGGGGTGACATGCCAGGGAGTACACG 1021 GAGCGTTCCGATGACTCTCGTGTGACCAAGGCAGTACAACACTCCACGGAGGACTCGAAG
                                                          H  T  L  F  W  A  M
1081 AGATTCGGAAATATGGAACACAGAACTGACAGGATGGTAGcacacgttgttctgggccat
         S  G  H  G  I  P  R  S  Y  R  H  M
1141 gtctggccacggaatccctcgcagctatcgccatatgGTACGTTTGCCTGGCTGAGATGA
                                             D  G  F  G  V  H  T  F  R  F
1201 CCGTGAATCCATTTCTAACCTCAAGTCCAGgatggcttcggcgtccacacgttccggttt
         V  K  D  D  G  S  S  K  L  I  K  W  H  F  K  S  R  Q  G  K
1261 gtcaaagatgacggctcgtccaagttgatcaagtggcatttcaagtcacgccagggaaag
         A  S  L  V  W  E  E  A  Q  V  L  S  G  K  N  A  D  F  H  R
1321 gcgagtctagtctgggaagaggcgcaggttctgtctggcaagaatgccgacttccaccgt
         Q  D  L  W  D  A  I  E  S  G  N  G  P  E  W  D  V  C  V  Q
1381 caggacctctgggatgctattgagtccgggaacggaccagaatgggatgtctgcgtccag
         I  V  D  E  S  Q  A  Q  A  F  G  F  D  L  L  D  P  T  K  I
1441 attgtcgatgagtcccaggcgcaagcctttggcttcgacttgctggacccgacaaagatc
         I  P  E  E  Y  A  P  L  T  K  L  G  L  L  K  L  D  R  N  P
1501 atccccgaggagtacgccccccttgacgaagctgggcctcttgaaactggatcgcaatccg
```

Fig. 2

```
           T  N  Y  F  A  E  T  E  Q  V  M  F  Q  P  G  H  I  V  R  G
1561 accaactacttcgccgagacggagcaggtcatgttccaacccggtcatatcgtccgcggc
        I  D  F  T  E  D  P  L  L  Q  G  R  L  F  S  Y  L  D  T  Q
1621 atcgacttcacggaggatccctgctacagggacgtctcttctcgtaccttgacacgcag
        L  N  R  N  G  G  P  N  F  E  Q  L  P  I  N  M  P  R  V  P
1681 ctgaaccggaatggcgggcccaactttgagcagctgcccatcaacatgccgcgggtgccg
        I  H  N  N  R  D  G  A  G  Q  M  F  I  H  R  N  K  Y  P
1741 attcacaacaataatcgcgacggcgccggccagatgttcatccacaggaacaagtatcct
                                                                Y  T
1801 tGTAAGTACCTCTTTTGCCTCGATCGTTGTGGTGCCGGCTTGCTGACAGACGCAGacact
        P  N  T  L  N  S  G  Y  P  R  Q  A  N  Q  N  A  G  R  G  F
1861 cccaacaccctgaacagtggttatccgcggcaagccaaccaaaatgccggacgcggattc
        F  T  A  P  G  R  T  V  S  G  A  L  V  R  E  V  S  P  T  F
1921 ttcacagcgcctggccgtaccgtcagcggtgccctcgtccgtgaggtgtcgccaacattc
        N  D  H  W  S  Q  P  R  L  F  F  N  S  L  T  P  V  E  Q  Q
1981 aacgaccactggtcgcagccccgtctcttcttcaactccctcactcccgtcgaacagcag
        F  L  V  N  A  M  R  F  E  I  S  L  V  K  S  E  E  V  R  K
2041 ttcctcgtcaacgccatgcgcttcgaaatcagccttgtgaagtcggaagaagtcaggaag
        N  V  L  T  Q  L  N  R  V  S  H  D  V  A  G  R  V  A  A  A
2101 aacgtgctcacccagctcaaccgcgtcagccatgatgtggccgggcgcgtggccgccgct
        I  G  L  A  A  P  D  A  D  D  T  Y  Y  H  N  N  K  T  A  G
2161 atcggcctcgccgcgcccgacgcggacgacacatactaccacaacaacaagacggctggc
        V  S  I  L  G  S  G  P  L  P  T  I  K  T  L  R  V  G  I  L
2221 gtctcgatccttggaagcgggccccttgcctaccatcaagactctccgcgtcggcatcctg
        A  T  T  S  E  S  S  A  L  D  Q  A  A  Q  L  R  T  R  L  E
2281 gctaccacgagcgagtcgagcgcgctggatcaggcagcccagctccgcacccgtctggaa
        K  D  G  L  V  V  T  V  V  A  E  T  L  R  E  G  V  D  Q  T
2341 aaggacgggcttgtggtcacggttgtggctgaaacgctgcgcgagggggtagaccagaca
        Y  S  T  A  D  A  T  G  F  D  G  V  V  V  V  D  G  A  A  A
2401 tactcgacggcggatgccacgggtttcgacggcgttgttgttgtggacggggcggcggcg
        L  F  A  S  T  A  S  S  P  L  F  P  T  G  R  P  L  Q  I  F
2461 ctgtttgccagcaccgcgtcgtcgccgttgttcccgacgggcaggccgttgcagatcttt
        V  D  A  Y  R  W  G  K  P  V  G  V  C  G  G  K  S  S  E  V
2521 gtggacgcgtatcggtggggaaagccggtcggtgtgtgtggtgggaagtcgagcgaggtg
        L  D  A  A  D  V  P  E  N  G  D  G  V  Y  S  E  E  S  V  D
2581 ttggatgcggcggatgttccggaaaatggggacggggtgtattcggaggagtcggtggac
        K  F  V  E  E  F  E  K  G  L  A  T  F  R
2641 aagtttgtggaggagtttgagaagggggttggctactttcaggGTGAGTCTTGGTGCCTTT

2701 GTTTTTTGAGATGTTATTGTTTTGTTTCGTCTCGGACTTTGTGAAAGAATGACGGACTGA

2761 CGTCTTTGGTATCTAGTTTACCGATCGGTTTGCTCTCGACTCTTAGGAGGACGAATGGAC
                                                             E  S  E  L
2821 AGAAAGTGAGACCGAGAGTGACTCAGAGACTGAGTTGGAGTCGGAATAGgaatcggaatt
        E  S  E  S  G  S  E  S  G  S  E  N  E  F  C  I  Q  E  V  D
2881 ggaatcggagtcagggtcggagtcaggatcagagaatgaattttgtatccaggaagtcga
        G  V  Y  Q  I  C  N  H  Q  E  D  E  D  S  E  D  S  T  S  E
2941 tggggtgtatcagatttgtaatcaccaggaggatgaggattctgaggatagcacttcgga
        E  E  G  D  E  V  E  P  V  I  S  W  G  *
3001 agaggagggagatgaagttgagcctgtcatttcatggggatga
```

Fig. 2 continued

```
         M   R   A   V   Q   L   L   P   S   L   A   G   L   I   G   A   A   S   A   V
   1     atgcgcgcagtgcagcttctgcccagcctcgccggcctgattggcgctgcctctgccgtt
         G   C   P   Y   L   T   G   Q   L   D   A   R   D   V   H   N   P   H   E   F
  61     ggatgtccgtatctgacgggccagctcgatgccagagacgtgcacaatccgcacgagttc
         Q   R   R   Q   D   P   G   D   A   A   A   S   T   E   Q   F   L   S   Q   F
 121     cagcgtcgacaggatcccggagatgcggctgcgtccacagagcagttcctgtcccagttc
         Y   L   N   D   S   N   S   Y   M   T   T   D   V   G   G   P   I   S   D   Q
 181     tatctcaatgacagcaacagctacatgaccactgatgtcggcggccccatctcggatcag
         N   S   L   K   A   G   E   R   G   P   T   L   L   E   D   F   I   F   R   Q
 241     aacagtttgaaggccggagagcgcggtccaaccctgttggaggacttcatcttccgtcag
         K   I   Q   H   F   D   H   E   R
 301     aagatccagcactttgatcacgagcggGTAGGTTGTACCATCCATGCGAGAGAGATCGAT
                                             V   P   E   R   A   V   H   A   R   G   A   G   A
 361     CGATGTTGACGTGGTGGCAGgtcccagaacgcgcagtccatgctcgaggagccggcgccc
         H   G   T   F   T   S   Y   G   N   W   S   N   I   T   A   A   S   F   L   S
 421     acggaacgttcacttcctacggaaactggtccaacatcactgcggcctccttcctgagcg
         A   E   G   K   E   T   P   V   F   V   R   F   S   T   V   A   G   S   R   G
 481     ctgaagggaaggagacccccgtgtttgtgcgcttctccaccgtggccggaagtcgaggca
         S   A   D   T   A   R   D   V   H   G   F   A   T   R   F   Y   T   D   E   G
 541     gtgcggacacggcgcgcgatgtgcatggctttgccaccaggttctacactgacgagggca
         N   F                                                                           D   I
 601     actttgGTACGTCGTCTCACAATCCTCTCGACTGGCATCGTCTGACCGCTGAGCAGatat
             V   G   N   N   I   P   V   F   F   I   Q   D   A   I   L   F   P   D   L   I
 661     cgtcggcaacaacattccagtcttcttcatccaggacgccattctcttccctgatctgat
         H   A   V   K   P   S   P   D   N   E   I   P   Q   A   A   T   A   H   D   T
 721     ccatgctgtcaagcccagccccgacaacgagatcccccaggctgcgactgctcatgacac
         A   W   D   F   F   S   Q   Q   P   S   A   L   H   T   L   F   W   A   M   S
 781     ggcctgggacttcttcagccagcagcccagtgcgttgcacacgctcttctgggctatgtc
         G   H   G   I   P   R   S   F   R   H   M   D   G   F   G   V   H   T   F   R
 841     cggccatggaatccctcgctcttttcgccacatggacggctttggcgtccacactttccg
         F   V   T   D   D   G   A   S   K   L   V   K   F   H   W   T   S   L   Q   G
 901     attcgtgactgacgacggcgcctccaagctggtcaaattccactggacctcgctgcaggg
         R   A   S   L   V   W   E   E   A   Q   A   A   A   G   K   N   L   D   Y   M
 961     ccggggccagcctggtctgggaggaggcgcaagcggcagcgggaaagaacctggactatat
         R   Q   D   L   Y   D   N   I   E   A   G   R   Y   P   E   W   E
1021     gcgccaggacctctatgacaacatcgaagccggtcgatatcctgaatgggagGTAGGTGG
                                                                                 L   G   I   Q   I   V
1081     CCGCATTTTCTCGGCATATATATGTCCATGCTGACGTTCCTAGctgggcattcaaatcgt
         D   E   E   D   Q   L   K   F   G   F   D   L   L   D   P   T   K   I   I   P
1141     cgacgaggaggatcagctcaagtttggatttgatctgctggatccaaccaagatcattcc
         V   E   Y   V   P   I   T   P   L   G   K   L   Q   L   N   R   N   P   L   N
1201     tgttgaatatgtccccatcacgccgcttgggaagctgcagctcaaccggaatccgctcaa
         Y   F   A   E   T   E   Q   I   M
1261     ctatttcgccgagacggagcagataatgGTATGTAAACAGTTTGTTGTTCGATTCTTTGC
                                                 F   Q   P   G   H   I   V   R   G   I   D   F   T
1321     AGTAGACTGACGATACATAGttccaaccggcccatattgtgcgcggaattgactttaccg
         E   D   P   L   L   Q   G   R   L   F   S   Y   L   D   T   Q   L   N   R   N
1381     aagaccccttctcaggacggctcttctcctatctcgacacgcagttgaatcggaatg
         G   G   P   N   F   E   Q   L   P   I   N   R   P   R   V   P   W   H   N   N
1441     gaggccccaatttcgagcagcttcccatcaatcgtcctagggtgccatggcataacaaca
         N   R   D   G   F
1501     accgtgatggattcaGTAAGTTTACCCCCCTGCGCTGACTCTCTGCATGCTAACTCCACC
```

Fig. 3

```
            S  Q  A  F  I  P  L  N  K  A  A  Y  S  P  N  T  L  N  N  G
1561  AGgccaagcgtttatccccctgaacaaggcggcctacagcccgaacacgctcaacaatgg
            N  P  K  Q  A  N  Q  T  V  G  D  G  F  F  T  T  P  G  R  T
1621  caaccccaagcaggcgaaccagactgtgggcgatggattcttcaccactcccggacgtac
            T  S  G  R  L  M  R  T  V  S  S  T  F  S  D  V  W  S  Q  P
1681  gaccagtggccggctcatgcgcaccgtcagttcgaccttctccgacgtctggtcgcagcc
            R  L  F  Y  N  S  L  V  P  A  E  Q  Q  F  L  V  N  A  I  R
1741  tcggctgttctacaactcgctggtgccggccgagcagcagttcctcgtcaacgccatccg
            F  E  N  S  N  V  K  S  E  V  V  R  N  N  V  I  I  Q  L  N
1801  tttcgagaactccaacgtcaagagcgaagtggtccggaacaatgtcatcatccagctcaa
            R  V  D  N  D  L  A  R  R  V  A  R  V  I  G  V  A  E  P  E
1861  ccgcgtcgataacgacctcgcccgccgggttgctcgggtcattggcgttgcagaacccga
            P  D  P  T  Y  Y  H  N  N  K  T  A  N  V  G  T  F  G  T  P
1921  gcccgatccaacctattatcacaacaacaagacggccaacgtgggtacgtttggcacgcc
            L  K  R  I  D  G  L  K  V  G  V  L  A  T  V  G  D  P  D  S
1981  gctcaagcggatcgacggtctcaaagtcggtgtgcttgccacagttggcgacccagacag
            I  S  Q  G  Q  S  L  S  D  A  L  S  D  S  K  V  D  V  T  V
2041  tatcagtcagggccagagcctcagtgacgcgctctcggactccaaggtcgatgtcactgt
            V  A  E  S  F  T  D  G  V  D  A  L  Y  T  N  S  D  A  T  G
2101  cgttgctgagtcttcacggacggggtcgatgcgctctacaccaactcggacgcgaccgg
            F  D  A  V  I  V  A  D  G  A  E  G  L  F  T  P  S  S  F  T
2161  cttcgacgccgttatcgtggctgatggcgccgaagggcttttttaccccgagtagcttcac
            A  K  P  T  N  S  F  S  T  T  T  L  Y  P  A  G  R  P  L  Q
2221  agccaaaccgacgaactcattctcgacgacaacgctttatccggccggtcgtccgctgca
            I  L  V  D  A  F  R  F  G  K  P  V  G  A  L  G  S  G  A  K
2281  gatcctggtcgacgccttccggttcggcaagcccgtcggcgctctgggcagcggagctaa
            A  L  D  A  A  G  I  S  T  S  R  P  G  V  Y  V  A  N  S  T
2341  ggcgcttgatgcggcaggtatctcgactagccggcctggtgtgtacgtcgccaactcgac
            S  E  A  F  T  D  D  I  E  D  G  L  R  T  F  K  F  L  D  R
2401  cagcgaggcgttcacggacgatatcgaggatggtttgcgaacgttcaagttcctcgaccg
            F  A  L  D  E  *
2461  gtttgcgctggatgagtga
```

Fig. 3 continued

SEQUENCE LISTING

```
<160> NUMBER OF SEQ ID NOS: 43

<210> SEQ ID NO 1
<211> LENGTH: 2354
<212> TYPE: DNA
<213> ORGANISM: Thermoascus aurantiacus

<400> SEQUENCE: 1
atggctgcta caatcgctgg tgggctacac aaggcccagg acctcatcaa gaacaccaca      60
tcgagggaca agaagctggt ggacttggag cgcgacactg acaatatcca cacaaagtgc     120 cccttacgt cagaccatgg cgttgctatt agcaataccg acaattggct gaaggctgtg      180
gattaccagc atactggtcc atccctcctg gaagatcagt ttgctagaga gaaggtatat     240
ccaatttctc ttcccgaatg aaagctcggt tgcagcattt gactcgcatc cagattcacc     300
gcttcgatca cgagcgcatt ccagaaagag tggttcatgc acgaggagca ggtgccttcg     360
gaaacttcag actcaaggag agcgcggcgg atgttaccca cgcaggagta ctgacggaca     420
cgtcgcgaaa caccccagtc tttgtccgtt tctccactgt ccaagggagt aggggtagtg     480
ccgacacagt ccgcgacgtt cgaggattcg cggttaagtt ctacaccgac gagggtaatt     540
gggatatagt gggcaacaac atccctgtct tcttcatcca ggaagctata aagtttcccg     600
atgtcggtac gcgatctcgt attctacccg ttgtcaggtc tagcaactaa ctgcactaag     660
ttcacgctgt caagccggag ccacacaatg aggtccctac agcgcagacg gcccataata     720
acttctggga cttcgtatat atgcatcccg aggcgacaca catgttcatg tggatcatgt     780
ctgatagagc aattccacga tcgttccgta tgatgcaagg attcagtgtg aacactttcg     840
```

```
ttctcgttaa caaagagggc aaacgctcct ttgtcaagtt ccattggatc cccaagcttg    900
gcctgcactc actcgtttgg gatgaggccc agaaaattgc tggccaggat cccgattttc    960
accggaaaga cctctgggag gccattgcca caagatcta ccccaaatgg gattttggta   1020
tccaggtgat cccagaggag aaacagcatg acttcgaatt tgatctcctc gatgccacca   1080
agctctggcc cgaggatctc atccccgtcc gtatcatcgg agagctggag cttaaccgca   1140
atccggacga gttcttcacc cagacagagc aggttgcttt ctgcaccagc acattgtcc   1200
ccggcataga attctctgat gaccctctac tccatggccg caacttctcc tacttcgata   1260
cccagattac cagactggga attaactggg aagagcttcc aatcaaccgt cccgtatgtc   1320
ctgttttcaa ccacaacagg gacggccagt cgcgacatag gatcacacag ggaactgtta   1380
actactggcc caaccgcttt gaagcttgtc caccgaccaa acccgaggaa ggtgggttcg   1440
taacataccc gtcgacattc cacggcctca acagcgcac cttgagttat aagttccgtg   1500
aacatcataa ccaagcgcag atgttctata actccctgtc ggagcacgaa aagctccatc   1560
ttaccaaggc attcagcttc gagcttgacc actgcgacga cccaaccgtc tacagtcggt   1620
tggccggcga acgcctggcc gaaatcgacc tcgggctcgc ccagaaagtc gccgagatgg   1680
tcggcgcccc gatcccgacg agagccctca aggagaacaa aggccagcga gcggtccggc   1740
tgtccttcac ggaattctat cctcctaacc caaccatcga gtcccgccgt gtggctatca   1800
taatcggcga cggctacgac ccgatagcgt tcttgggcat caaagcagcc gtcgaggccg   1860
ccaacgctct gcccttcatc atcggcacca agcgccagcc catgttcgcc gaaggcgaag   1920
acagaaccac ctccaaggcc gtcatcccgg accaccagta cgacggacag cgctcgaccc   1980
tgttcgacgc gaccttcatc ccaggcggct ctcacgtcaa gacgctggcc cagaacgggc   2040
agatccggta ctggatcacc gagaccttcg ggcacctgaa ggctctggcc gcgacgggcg   2100
aggctgtcga ccttgtcaag caggtgctga gcgtcgttcc cggtctgcag ttcgccactc   2160
caaacgagcc caacgtcgtc gagtcatacg gcgtcgtcac cgtgggcggg aagcagaagc   2220
ctgagagctt cagcgagggg ttcaagatcc tcaaggatgc gaaggacttt gtgggccagt   2280
tcttctacca gatctcacag catcggaact ttaagcgtga gctggaaggg ctgcatgcca   2340
ccgttgcgtt ttaa                                                    2354
```

<210> SEQ ID NO 2
<211> LENGTH: 746
<212> TYPE: PRT
<213> ORGANISM: Thermoascus aurantiacus

<400> SEQUENCE: 2

```
Met Ala Ala Thr Ile Ala Gly Gly Leu His Lys Ala Gln Asp Leu Ile
1               5                   10                  15

Lys Asn Thr Thr Ser Arg Asp Lys Lys Leu Val Asp Leu Glu Arg Asp
            20                  25                  30

Thr Asp Asn Ile His Thr Lys Cys Pro Phe Thr Ser Asp His Gly Val
        35                  40                  45

Ala Ile Ser Asn Thr Asp Asn Trp Leu Lys Ala Val Asp Tyr Gln His
    50                  55                  60

Thr Gly Pro Ser Leu Leu Glu Asp Gln Phe Ala Arg Glu Lys Ile His
65                  70                  75                  80

Arg Phe Asp His Glu Arg Ile Pro Glu Arg Val Val His Ala Arg Gly
                85                  90                  95

Ala Gly Ala Phe Gly Asn Phe Arg Leu Lys Glu Ser Ala Ala Asp Val
```

```
                100             105              110
Thr His Ala Gly Val Leu Thr Asp Thr Ser Arg Asn Thr Pro Val Phe
            115             120             125

Val Arg Phe Ser Thr Val Gln Gly Ser Arg Gly Ser Ala Asp Thr Val
            130             135             140

Arg Asp Val Arg Gly Phe Ala Val Lys Phe Tyr Thr Asp Glu Gly Asn
145             150             155             160

Trp Asp Ile Val Gly Asn Asn Ile Pro Val Phe Phe Ile Gln Glu Ala
            165             170             175

Ile Lys Phe Pro Asp Val Val His Ala Val Lys Pro Glu Pro His Asn
            180             185             190

Glu Val Pro Thr Ala Gln Thr Ala His Asn Asn Phe Trp Asp Phe Val
            195             200             205

Tyr Met His Pro Glu Ala Thr His Met Phe Met Trp Ile Met Ser Asp
            210             215             220

Arg Ala Ile Pro Arg Ser Phe Arg Met Met Gln Gly Phe Ser Val Asn
225             230             235             240

Thr Phe Val Leu Val Asn Lys Glu Gly Lys Arg Ser Phe Val Lys Phe
            245             250             255

His Trp Ile Pro Lys Leu Gly Leu His Ser Leu Val Trp Asp Glu Ala
            260             265             270

Gln Lys Ile Ala Gly Gln Asp Pro Asp Phe His Arg Lys Asp Leu Trp
            275             280             285

Glu Ala Ile Ala Asn Lys Ile Tyr Pro Lys Trp Asp Phe Gly Ile Gln
            290             295             300

Val Ile Pro Glu Glu Lys Gln His Asp Phe Glu Phe Asp Leu Leu Asp
305             310             315             320

Ala Thr Lys Leu Trp Pro Glu Asp Leu Ile Pro Val Arg Ile Ile Gly
            325             330             335

Glu Leu Glu Leu Asn Arg Asn Pro Asp Glu Phe Phe Thr Gln Thr Glu
            340             345             350

Gln Val Ala Phe Cys Thr Ser His Ile Val Pro Gly Ile Glu Phe Ser
            355             360             365

Asp Asp Pro Leu Leu His Gly Arg Asn Phe Ser Tyr Phe Asp Thr Gln
            370             375             380

Ile Thr Arg Leu Gly Ile Asn Trp Glu Glu Leu Pro Ile Asn Arg Pro
385             390             395             400

Val Cys Pro Val Phe Asn His Asn Arg Asp Gly Gln Ser Arg His Arg
            405             410             415

Ile Thr Gln Gly Thr Val Asn Tyr Trp Pro Asn Arg Phe Glu Ala Cys
            420             425             430

Pro Pro Thr Lys Pro Glu Glu Gly Phe Val Thr Tyr Pro Ser Thr
            435             440             445

Phe His Gly Leu Lys Gln Arg Thr Leu Ser Tyr Lys Phe Arg Glu His
            450             455             460

His Asn Gln Ala Gln Met Phe Tyr Asn Ser Leu Ser Glu His Glu Lys
465             470             475             480

Leu His Leu Thr Lys Ala Phe Ser Phe Glu Leu Asp His Cys Asp Asp
            485             490             495

Pro Thr Val Tyr Ser Arg Leu Ala Gly Glu Arg Leu Ala Glu Ile Asp
            500             505             510

Leu Gly Leu Ala Gln Lys Val Ala Glu Met Val Gly Ala Pro Ile Pro
            515             520             525
```

```
Thr Arg Ala Leu Lys Glu Asn Lys Gly Gln Arg Ala Val Arg Leu Ser
        530                 535                 540

Phe Thr Glu Phe Tyr Pro Asn Pro Thr Ile Glu Ser Arg Arg Val
545                 550                 555                 560

Ala Ile Ile Ile Gly Asp Gly Tyr Asp Pro Ile Ala Phe Leu Gly Ile
                565                 570                 575

Lys Ala Ala Val Glu Ala Ala Asn Ala Leu Pro Phe Ile Ile Gly Thr
            580                 585                 590

Lys Arg Gln Pro Met Phe Ala Glu Gly Glu Asp Arg Thr Thr Ser Lys
        595                 600                 605

Gly Val Ile Pro Asp His Gln Tyr Asp Gly Gln Arg Ser Thr Leu Phe
    610                 615                 620

Asp Ala Thr Phe Ile Pro Gly Gly Ser His Val Lys Thr Leu Ala Gln
625                 630                 635                 640

Asn Gly Gln Ile Arg Tyr Trp Ile Thr Glu Thr Phe Gly His Leu Lys
                645                 650                 655

Ala Leu Ala Ala Thr Gly Glu Ala Val Asp Leu Val Lys Gln Val Leu
            660                 665                 670

Ser Val Val Pro Gly Leu Gln Phe Ala Thr Pro Asn Glu Pro Asn Val
        675                 680                 685

Val Glu Ser Tyr Gly Val Thr Val Gly Lys Gln Lys Pro Glu
    690                 695                 700

Ser Phe Ser Glu Gly Phe Lys Ile Leu Lys Asp Ala Lys Asp Phe Val
705                 710                 715                 720

Gly Gln Phe Phe Tyr Gln Ile Ser Gln His Arg Asn Phe Lys Arg Glu
                725                 730                 735

Leu Glu Gly Leu His Ala Thr Val Ala Phe
            740                 745

<210> SEQ ID NO 3
<211> LENGTH: 2452
<212> TYPE: DNA
<213> ORGANISM: Talaromyces stipitatus

<400> SEQUENCE: 3
atgcgagggg catactctct cggcgccttt gccagtctca tcgcggtagc ttcggctgcc      60
tgcccaatgc tgactggcga atcccagca ggcagcattg caaaccctca tcaccttgga     120
agccgcgctg actcgaatgc ttccgacgaa acagaagcct ttctgtccga attctacctt     180
aatgacaaca cagcttcct cactaccgat gtgggcggcc gatagaaga ccaaaacagt      240 ctcaaggccg gcattcgcgg atcaacgctc ttggaggatt tcatctttcg ccagaagatt     300
cagcgctttg atcacgagcg tgtaagttct gaaatcata tgactacttc gatgtgtact     360
tacgacttct aggtgcccga acgcgctgtg catgctcgag gtgctggtgc tcatggtgta     420
ttcacatcgt atgctgattg gtccaacatc accgctgctt cattcctagg agctgccgga     480
aaggaaacgc ccacctttgt acgcttctcg actgttgccg gcagtcgtgg tagtgccgat     540
accgctcgtg atgttcacgg ctttgctacc cgcttctata ctgacgaagg caactacggt     600
aagatctatc catggtcata gcagcctata catttgctaa ctcacagcag atatcgttgg     660
aaacaacatt cccgtcttct tcatccaaga cgctattcag ttccctgacc tcattcatgc     720
agtcaagcca cagccagcca gtgaaatccc acaggccgct actgcccacg acactgctta     780
tgatttcttc ggccagcagc ctagtacctt gcataccctc ttctgggcaa tggcaggtca     840
```

-continued

```
tggtatcccg cggtctttcc gccatgttga cggattcggc gttcacgctt accgatttgt    900
gactgacgac ggctcttcaa agctagtcaa attccactgg aagtccttac agggtcgtgc    960
aagcttagtc tgggaagaag ctcaagccac tgctggcaag aatgctgatt tcatgaggca   1020
agatctgttt gacaatattg cagctggccg gtacccagaa tgggaggtga gtataagttg   1080
cctgtcctcc gaagaatttc actaacatga atagctcggc gtgcaactta tcgaggaacc   1140
agaccagctc agctacggat ttgatctgct tgatcccacc aagatactcc cagttgaaca   1200
agttccaatc accccgctcg gaaaaatgca actcaaccgt aacccgctaa actactttgc   1260
tgagaccgag caagtaatgg tacgttaact tctcttctcc cctccccccc aaacaactcc   1320
gggtacagct catgctgatc attttagttc aacctggtc acattgttcg tggcattgat   1380
ttcacagagg accctcttct ccaaggccgt ctattttctt acctcgacac tcagcttaat   1440
cgcaacggtg gccccaactt tgagcagatt ccgatcaacc gtcctcgtgt tcctatccac   1500
aataacaacc gagacggttt tggccagatg tttattccac tcaacgatgc ggcatactcg   1560
ccaaacaccc taagcgatgg caaccctaag caggcaaatg agactgttgg aaatggtttc   1620
tttactactc caggacgcac tgccaatgga aacctcgtcc gcgccaaaag cccaacgttt   1680
gcggatgtgt ggtcccaacc tggcctcttt tacaactcct tgcagccac cgaacaacag   1740
tttgtcatca atgctctgcg gttcgagcta gccaatgtag caagtgagac tgtgaagaat   1800
aacttcatca cccagatcaa tcgcgtaaac aacaccttgg caacacttgt agccactgca   1860
attggtgtca atgctcctga acccgacccg acttactacc accacaacaa gacgtctgat   1920
gtgggaacat tcggtactcc tctgaagaag attgatggtc tcaaggtcgg agtccttgct   1980
tctgtcaacg atgaaaacag tatttccgag ggacagtctc tagcacgaag cttggcggat   2040
ttgaatgtgg acgtcgttat tgtcgctgaa cgacttgctg gtaatgtctc agctacatac   2100
tccgcatctg acgctatcaa cttcgatgct gttattgtca cttcaggggc taagggtctc   2160
tttgacctc aaaccttcac cgccgtatcc aacaccactc tttatcccgt gggccgtccc   2220
acgcagattt tggtcgacgc tttccgctac ggcaagccgg ttggagcagt gggtagtgca   2280
agcgaagcgc tgactgtttc ggacattgat actgaccgca gtggtgtgat tactggtgat   2340
ttgaacgacg agtttgtgaa gcaactgtcg gaggaccttg caacattcaa gttcttggac   2400
cgcttcaccg tcgacgagta gacgtttcca cgattaacac gagtaacttg tt           2452
```

<210> SEQ ID NO 4
<211> LENGTH: 733
<212> TYPE: PRT
<213> ORGANISM: Talaromyces stipitatus

<400> SEQUENCE: 4

```
Met Arg Gly Ala Tyr Ser Leu Gly Ala Phe Ala Ser Leu Ile Ala Val
1               5                   10                  15

Ala Ser Ala Ala Cys Pro Met Leu Thr Gly Glu Ile Pro Ala Gly Ser
            20                  25                  30

Ile Ala Asn Pro His His Leu Gly Ser Arg Ala Asp Ser Asn Ala Ser
        35                  40                  45

Asp Glu Thr Glu Ala Phe Leu Ser Glu Phe Tyr Leu Asn Asp Asn Asn
    50                  55                  60

Ser Phe Leu Thr Thr Asp Val Gly Gly Pro Ile Glu Asp Gln Asn Ser
65                  70                  75                  80

Leu Lys Ala Gly Ile Arg Gly Ser Thr Leu Leu Glu Asp Phe Ile Phe
                85                  90                  95
```

```
Arg Gln Lys Ile Gln Arg Phe Asp His Glu Arg Val Pro Glu Arg Ala
            100                 105                 110

Val His Ala Arg Gly Ala Gly Ala His Gly Val Phe Thr Ser Tyr Ala
            115                 120                 125

Asp Trp Ser Asn Ile Thr Ala Ala Ser Phe Leu Gly Ala Ala Gly Lys
130                 135                 140

Glu Thr Pro Thr Phe Val Arg Phe Ser Thr Val Ala Gly Ser Arg Gly
145                 150                 155                 160

Ser Ala Asp Thr Ala Arg Asp Val His Gly Phe Ala Thr Arg Phe Tyr
                165                 170                 175

Thr Asp Glu Gly Asn Tyr Asp Ile Val Gly Asn Asn Ile Pro Val Phe
            180                 185                 190

Phe Ile Gln Asp Ala Ile Gln Phe Pro Asp Leu Ile His Ala Val Lys
            195                 200                 205

Pro Gln Pro Ala Ser Glu Ile Pro Gln Ala Ala Thr Ala His Asp Thr
            210                 215                 220

Ala Tyr Asp Phe Phe Gly Gln Gln Pro Ser Thr Leu His Thr Leu Phe
225                 230                 235                 240

Trp Ala Met Ala Gly His Gly Ile Pro Arg Ser Phe Arg His Val Asp
                245                 250                 255

Gly Phe Gly Val His Ala Tyr Arg Phe Val Thr Asp Asp Gly Ser Ser
            260                 265                 270

Lys Leu Val Lys Phe His Trp Lys Ser Leu Gln Gly Arg Ala Ser Leu
            275                 280                 285

Val Trp Glu Glu Ala Gln Ala Thr Ala Gly Lys Asn Ala Asp Phe Met
            290                 295                 300

Arg Gln Asp Leu Phe Asp Asn Ile Ala Ala Gly Arg Tyr Pro Glu Trp
305                 310                 315                 320

Glu Leu Gly Val Gln Leu Ile Glu Glu Pro Asp Gln Leu Ser Tyr Gly
                325                 330                 335

Phe Asp Leu Leu Asp Pro Thr Lys Ile Leu Pro Val Glu Gln Val Pro
            340                 345                 350

Ile Thr Pro Leu Gly Lys Met Gln Leu Asn Arg Asn Pro Leu Asn Tyr
            355                 360                 365

Phe Ala Glu Thr Glu Gln Val Met Phe Gln Pro Gly His Ile Val Arg
            370                 375                 380

Gly Ile Asp Phe Thr Glu Asp Pro Leu Leu Gln Gly Arg Leu Phe Ser
385                 390                 395                 400

Tyr Leu Asp Thr Gln Leu Asn Arg Asn Gly Pro Asn Phe Glu Gln
                405                 410                 415

Ile Pro Ile Asn Arg Pro Arg Val Pro Ile His Asn Asn Asn Arg Asp
            420                 425                 430

Gly Phe Gly Gln Met Phe Ile Pro Leu Asn Asp Ala Ala Tyr Ser Pro
            435                 440                 445

Asn Thr Leu Ser Asp Gly Asn Pro Lys Gln Ala Asn Glu Thr Val Gly
            450                 455                 460

Asn Gly Phe Phe Thr Thr Pro Gly Arg Thr Ala Asn Gly Asn Leu Val
465                 470                 475                 480

Arg Ala Lys Ser Pro Thr Phe Ala Asp Val Trp Ser Gln Pro Gly Leu
                485                 490                 495

Phe Tyr Asn Ser Leu Thr Ala Thr Glu Gln Gln Phe Val Ile Asn Ala
            500                 505                 510
```

```
Leu Arg Phe Glu Leu Ala Asn Val Ala Ser Glu Thr Val Lys Asn Asn
            515                 520                 525

Phe Ile Thr Gln Ile Asn Arg Val Asn Asn Thr Leu Ala Thr Leu Val
        530                 535                 540

Ala Thr Ala Ile Gly Val Asn Ala Pro Glu Pro Asp Pro Thr Tyr Tyr
545                 550                 555                 560

His His Asn Lys Thr Ser Asp Val Gly Thr Phe Gly Thr Pro Leu Lys
                565                 570                 575

Lys Ile Asp Gly Leu Lys Val Gly Val Leu Ala Ser Val Asn Asp Glu
            580                 585                 590

Asn Ser Ile Ser Glu Gly Gln Ser Leu Ala Arg Ser Leu Ala Asp Leu
        595                 600                 605

Asn Val Asp Val Val Ile Val Ala Glu Arg Leu Ala Gly Asn Val Ser
610                 615                 620

Ala Thr Tyr Ser Ala Ser Asp Ala Ile Asn Phe Asp Ala Val Ile Val
625                 630                 635                 640

Thr Ser Gly Ala Lys Gly Leu Phe Gly Pro Gln Thr Phe Thr Ala Val
                645                 650                 655

Ser Asn Thr Thr Leu Tyr Pro Val Gly Arg Pro Thr Gln Ile Leu Val
                660                 665                 670

Asp Ala Phe Arg Tyr Gly Lys Pro Val Gly Ala Val Gly Ser Ala Ser
            675                 680                 685

Glu Ala Leu Thr Val Ser Asp Ile Asp Thr Asp Arg Ser Gly Val Ile
        690                 695                 700

Thr Gly Asp Leu Asn Asp Glu Phe Val Lys Gln Leu Ser Glu Asp Leu
705                 710                 715                 720

Ala Thr Phe Lys Phe Leu Asp Arg Phe Thr Val Asp Glu
                725                 730

<210> SEQ ID NO 5
<211> LENGTH: 3076
<212> TYPE: DNA
<213> ORGANISM: Humicola insolens

<400> SEQUENCE: 5
atgaacagag tcacgaatct cctcgcctgg gccggcgcga tagggctcgc ccaagcaaca      60
tgcccctttg cggaccctgc cgctctgtat aggcgtcaag atactaccag cggccagtcg     120
ccacttgcag catacgaggt ggatgacagc accggatacc tgacctccga tgttggcggg     180
cccattcagg accagaccag cctcaaggca ggcatcccgg gtccgaccct tcttgaggac     240
tttatgttcc gccagaagat ccagcacttc gaccatgaac gggtaaggac ataatgctca     300
cacgagcggc tgcgtaccta tttatttccg agacattggg ctggctggct ggctgtgact     360
gcctgagttt ggggacatac ggagtacctt actgacgcgc tgatccactc caggttcccg     420
aaagggcggt ccatgctcga ggcgctggag cacacgggac cttcacgagt tacgccgact     480
ggagtaacat cacagcggcg tcctttctga acgccacagg aaagcagacg ccggtgtttg     540
tccggttctc gaccgttgct gggtctcgag ggagcgcaga cacggcgaga cgttcatg      600 gtttcgcgac gcggttgtaa gttttgttgt gtttcattcg ttccggtctg tagaggaggg     660
ttaggatatg agctaatgtg tgtgtgtgtg tgtgtgtgtg tgtgaagtta cactgatgaa     720
ggcaactttg gtacgtccca tgcatggtcc tcaattctct tatctggcag cgatgtggtc     780
attgtcgacg ttgctaactt gcgtagatat cgtcggaaac aacatcccgg tattcttcat     840
tcaagatgca atccagttcc ctgaccttat ccactcggtc aagccgcgtc ccgacaacga     900
```

```
gattccccaa gcggcgacgg ctcatgattc agcttgggac ttcttcagcc agcagccaag    960
caccatggta agcaatggac caaggagccg cacctggggt gacatgccag ggagtacacg   1020
gagcgttccg atgactctcg tgtgaccaag gcagtacaac actccacgga ggactcgaag   1080
agattcggaa atatgaaaca cagaactgac aggatggtag cacacgttgt tctgggccat   1140
gtctggccac ggaatccctc gcagctatcg ccatatggta cgtttgcctg gctgagatga   1200
ccgtgaatcc atttctaacc tcaagtccag gatggcttcg cgtccacac gttccggttt    1260
gtcaaagatg acggctcgtc caagttgatc aagtggcatt tcaagtcacg ccagggaaag   1320
gcgagtctag tctgggaaga ggcgcaggtt ctgtctggca agaatgccga cttccaccgt   1380
caggacctct gggatgctat tgagtccggg aacggaccag aatgggatgt ctgcgtccag   1440
attgtcgatg agtcccaggc gcaagccttt ggcttcgact tgctggaccc gacaaagatc   1500
atccccgagg agtacgcccc cttgacgaag ctgggcctct tgaaactgga tcgcaatccg   1560
accaactact tcgccgagac ggagcaggtc atgttccaac ccggtcatat cgtccgcggc   1620
atcgacttca cggaggatcc cctgctacag ggacgtctct tctcgtacct tgacacgcag   1680
ctgaaccgga atggcgggcc caactttgag cagctgccca tcaacatgcc gcgggtgccg   1740
attcacaaca ataatcgcga cggcgccggc cagatgttca tccacaggaa caagtatcct   1800
tgtaagtacc tcttttgcct cgatcgttgt ggtgccggct tgctgacaga cgcagacact   1860
cccaacaccc tgaacagtgg ttatccgcgg caagccaacc aaaatgccgg acgcggattc   1920
ttcacagcgc ctggccgtac cgtcagcggt gccctcgtcc gtgaggtgtc gccaacattc   1980
aacgaccact ggtcgcagcc ccgtctcttc ttcaactccc tcactcccgt cgaacagcag   2040
ttcctcgtca acgccatgcg cttcgaaatc agccttgtga agtcggaaga agtcaggaag   2100
aacgtgctca cccagctcaa ccgcgtcagc catgatgtgg ccgggcgcgt ggccgccgct   2160
atcggcctcg ccgcgcccga cgcggacgac acatactacc acaacaacaa gacggctggc   2220
gtctcgatcc ttggaagcgg gccccttgcct accatcaaga ctctccgcgt cggcatcctg   2280
gctaccacga gcgagtcgag cgcgctggat caggcagccc agctccgcac ccgtctggaa   2340
aaggacgggc ttgtggtcac ggttgtggct gaaacgctgc gcgagggggt agaccagaca   2400
tactcgacgg cggatgccac gggttttcgac ggcgttgttg ttgtggacgg ggcggcggcg   2460
ctgtttgcca gcaccgcgtc gtcgccgttg ttcccgacgg gcaggccgtt gcagatcttt   2520
gtggacgcgt atcggtgggg aaagccggtc ggtgtgtgtg gtgggaagtc gagcgaggtg   2580
ttggatgcgg cggatgttcc ggaaaatggg acggggtgt attcggagga gtcggtggac    2640
aagtttgtgg aggagtttga aagggggttg gctactttca gggtgagtct tggtgccttt   2700
gttttttgag atgttattgt tttgtttcgt ctcggacttt gtgaaagaat gacggactga   2760
cgtcttttggt atctagttta ccgatcggtt tgctctcgac tcttaggagg acgaatggac   2820
agaaagtgag accgagagtg actcagagac tgagttggac tcggaatagg aatcggaatt   2880
ggaatcggag tcagggtcgg agtcaggatc agagaatgaa ttttgtatcc aggaagtcga   2940
tggggtgtat cagatttgta atcaccagga ggatgaggat tctgaggata gcacttcgga   3000
agaggaggga gatgaagttg agcctgtcat ttcatgggga tgaggagggg agaaggaata   3060
gggtgggagt tgtacc                                                  3076
```

<210> SEQ ID NO 6
<211> LENGTH: 765
<212> TYPE: PRT

<213> ORGANISM: Humicola insolens

<400> SEQUENCE: 6

| Met | Asn | Arg | Val | Thr | Asn | Leu | Leu | Ala | Trp | Ala | Gly | Ala | Ile | Gly | Leu |
|---|---|---|---|---|---|---|---|---|---|---|---|---|---|---|---|
| 1 | | | | 5 | | | | | 10 | | | | | 15 | |

| Ala | Gln | Ala | Thr | Cys | Pro | Phe | Ala | Asp | Pro | Ala | Ala | Leu | Tyr | Arg | Arg |
|---|---|---|---|---|---|---|---|---|---|---|---|---|---|---|---|
| | | | 20 | | | | | 25 | | | | | 30 | | |

| Gln | Asp | Thr | Thr | Ser | Gly | Gln | Ser | Pro | Leu | Ala | Ala | Tyr | Glu | Val | Asp |
|---|---|---|---|---|---|---|---|---|---|---|---|---|---|---|---|
| | | | 35 | | | | | 40 | | | | | 45 | | |

| Asp | Ser | Thr | Gly | Tyr | Leu | Thr | Ser | Asp | Val | Gly | Gly | Pro | Ile | Gln | Asp |
|---|---|---|---|---|---|---|---|---|---|---|---|---|---|---|---|
| | 50 | | | | | 55 | | | | | 60 | | | | |

| Gln | Thr | Ser | Leu | Lys | Ala | Gly | Ile | Arg | Gly | Pro | Thr | Leu | Leu | Glu | Asp |
|---|---|---|---|---|---|---|---|---|---|---|---|---|---|---|---|
| 65 | | | | | 70 | | | | | 75 | | | | | 80 |

| Phe | Met | Phe | Arg | Gln | Lys | Ile | Gln | His | Phe | Asp | His | Glu | Arg | Val | Pro |
|---|---|---|---|---|---|---|---|---|---|---|---|---|---|---|---|
| | | | | 85 | | | | | 90 | | | | | 95 | |

| Glu | Arg | Ala | Val | His | Ala | Arg | Gly | Ala | Gly | Ala | His | Gly | Thr | Phe | Thr |
|---|---|---|---|---|---|---|---|---|---|---|---|---|---|---|---|
| | | | 100 | | | | | 105 | | | | | 110 | | |

| Ser | Tyr | Ala | Asp | Trp | Ser | Asn | Ile | Thr | Ala | Ala | Ser | Phe | Leu | Asn | Ala |
|---|---|---|---|---|---|---|---|---|---|---|---|---|---|---|---|
| | | | 115 | | | | | 120 | | | | | 125 | | |

| Thr | Gly | Lys | Gln | Thr | Pro | Val | Phe | Val | Arg | Phe | Ser | Thr | Val | Ala | Gly |
|---|---|---|---|---|---|---|---|---|---|---|---|---|---|---|---|
| | 130 | | | | | 135 | | | | | 140 | | | | |

| Ser | Arg | Gly | Ser | Ala | Asp | Thr | Ala | Arg | Asp | Val | His | Gly | Phe | Ala | Thr |
|---|---|---|---|---|---|---|---|---|---|---|---|---|---|---|---|
| 145 | | | | | 150 | | | | | 155 | | | | | 160 |

| Arg | Phe | Tyr | Thr | Asp | Glu | Gly | Asn | Phe | Asp | Ile | Val | Gly | Asn | Asn | Ile |
|---|---|---|---|---|---|---|---|---|---|---|---|---|---|---|---|
| | | | | 165 | | | | | 170 | | | | | 175 | |

| Pro | Val | Phe | Phe | Ile | Gln | Asp | Ala | Ile | Gln | Phe | Pro | Asp | Leu | Ile | His |
|---|---|---|---|---|---|---|---|---|---|---|---|---|---|---|---|
| | | | | 180 | | | | | 185 | | | | | 190 | |

| Ser | Val | Lys | Pro | Arg | Pro | Asp | Asn | Glu | Ile | Pro | Gln | Ala | Ala | Thr | Ala |
|---|---|---|---|---|---|---|---|---|---|---|---|---|---|---|---|
| | | | 195 | | | | | 200 | | | | | 205 | | |

| His | Asp | Ser | Ala | Trp | Asp | Phe | Phe | Ser | Gln | Gln | Pro | Ser | Thr | Met | His |
|---|---|---|---|---|---|---|---|---|---|---|---|---|---|---|---|
| | 210 | | | | | 215 | | | | | 220 | | | | |

| Thr | Leu | Phe | Trp | Ala | Met | Ser | Gly | His | Gly | Ile | Pro | Arg | Ser | Tyr | Arg |
|---|---|---|---|---|---|---|---|---|---|---|---|---|---|---|---|
| 225 | | | | | 230 | | | | | 235 | | | | | 240 |

| His | Met | Asp | Gly | Phe | Gly | Val | His | Thr | Phe | Arg | Phe | Val | Lys | Asp | Asp |
|---|---|---|---|---|---|---|---|---|---|---|---|---|---|---|---|
| | | | | 245 | | | | | 250 | | | | | 255 | |

| Gly | Ser | Ser | Lys | Leu | Ile | Lys | Trp | His | Phe | Lys | Ser | Arg | Gln | Gly | Lys |
|---|---|---|---|---|---|---|---|---|---|---|---|---|---|---|---|
| | | | 260 | | | | | 265 | | | | | 270 | | |

| Ala | Ser | Leu | Val | Trp | Glu | Glu | Ala | Gln | Val | Leu | Ser | Gly | Lys | Asn | Ala |
|---|---|---|---|---|---|---|---|---|---|---|---|---|---|---|---|
| | | | 275 | | | | | 280 | | | | | 285 | | |

| Asp | Phe | His | Arg | Gln | Asp | Leu | Trp | Asp | Ala | Ile | Glu | Ser | Gly | Asn | Gly |
|---|---|---|---|---|---|---|---|---|---|---|---|---|---|---|---|
| | 290 | | | | | 295 | | | | | 300 | | | | |

| Pro | Glu | Trp | Asp | Val | Cys | Val | Gln | Ile | Val | Asp | Glu | Ser | Gln | Ala | Gln |
|---|---|---|---|---|---|---|---|---|---|---|---|---|---|---|---|
| 305 | | | | | 310 | | | | | 315 | | | | | 320 |

| Ala | Phe | Gly | Phe | Asp | Leu | Leu | Asp | Pro | Thr | Lys | Ile | Ile | Pro | Glu | Glu |
|---|---|---|---|---|---|---|---|---|---|---|---|---|---|---|---|
| | | | | 325 | | | | | 330 | | | | | 335 | |

| Tyr | Ala | Pro | Leu | Thr | Lys | Leu | Gly | Leu | Leu | Lys | Leu | Asp | Arg | Asn | Pro |
|---|---|---|---|---|---|---|---|---|---|---|---|---|---|---|---|
| | | | 340 | | | | | 345 | | | | | 350 | | |

| Thr | Asn | Tyr | Phe | Ala | Glu | Thr | Glu | Gln | Val | Met | Phe | Gln | Pro | Gly | His |
|---|---|---|---|---|---|---|---|---|---|---|---|---|---|---|---|
| | | | 355 | | | | | 360 | | | | | 365 | | |

| Ile | Val | Arg | Gly | Ile | Asp | Phe | Thr | Glu | Asp | Pro | Leu | Leu | Gln | Gly | Arg |
|---|---|---|---|---|---|---|---|---|---|---|---|---|---|---|---|
| | 370 | | | | | 375 | | | | | 380 | | | | |

| Leu | Phe | Ser | Tyr | Leu | Asp | Thr | Gln | Leu | Asn | Arg | Asn | Gly | Gly | Pro | Asn |
|---|---|---|---|---|---|---|---|---|---|---|---|---|---|---|---|
| 385 | | | | | 390 | | | | | 395 | | | | | 400 |

```
Phe Glu Gln Leu Pro Ile Asn Met Pro Arg Val Pro Ile His Asn Asn
                405                 410                 415

Asn Arg Asp Gly Ala Gly Gln Met Phe Ile His Arg Asn Lys Tyr Pro
            420                 425                 430

Tyr Thr Pro Asn Thr Leu Asn Ser Gly Tyr Pro Arg Gln Ala Asn Gln
        435                 440                 445

Asn Ala Gly Arg Gly Phe Phe Thr Ala Pro Gly Arg Thr Val Ser Gly
    450                 455                 460

Ala Leu Val Arg Glu Val Ser Pro Thr Phe Asn Asp His Trp Ser Gln
465                 470                 475                 480

Pro Arg Leu Phe Phe Asn Ser Leu Thr Pro Val Glu Gln Gln Phe Leu
                485                 490                 495

Val Asn Ala Met Arg Phe Glu Ile Ser Leu Val Lys Ser Glu Glu Val
            500                 505                 510

Arg Lys Asn Val Leu Thr Gln Leu Asn Arg Val Ser His Asp Val Ala
        515                 520                 525

Gly Arg Val Ala Ala Ile Gly Leu Ala Ala Pro Asp Ala Asp Asp
    530                 535                 540

Thr Tyr Tyr His Asn Asn Lys Thr Ala Gly Val Ser Ile Leu Gly Ser
545                 550                 555                 560

Gly Pro Leu Pro Thr Ile Lys Thr Leu Arg Val Gly Ile Leu Ala Thr
                565                 570                 575

Thr Ser Glu Ser Ser Ala Leu Asp Gln Ala Ala Gln Leu Arg Thr Arg
            580                 585                 590

Leu Glu Lys Asp Gly Leu Val Val Thr Val Val Ala Glu Thr Leu Arg
        595                 600                 605

Glu Gly Val Asp Gln Thr Tyr Ser Thr Ala Asp Ala Thr Gly Phe Asp
    610                 615                 620

Gly Val Val Val Asp Gly Ala Ala Ala Leu Phe Ala Ser Thr Ala
625                 630                 635                 640

Ser Ser Pro Leu Phe Pro Thr Gly Arg Pro Leu Gln Ile Phe Val Asp
                645                 650                 655

Ala Tyr Arg Trp Gly Lys Pro Val Gly Val Cys Gly Gly Lys Ser Ser
            660                 665                 670

Glu Val Leu Asp Ala Ala Asp Val Pro Glu Asn Gly Asp Gly Val Tyr
        675                 680                 685

Ser Glu Glu Ser Val Asp Lys Phe Val Glu Phe Glu Lys Gly Leu
    690                 695                 700

Ala Thr Phe Arg Glu Ser Glu Leu Glu Ser Glu Ser Gly Ser Glu Ser
705                 710                 715                 720

Gly Ser Glu Asn Glu Phe Cys Ile Gln Glu Val Asp Gly Val Tyr Gln
                725                 730                 735

Ile Cys Asn His Gln Glu Asp Glu Asp Ser Glu Asp Ser Thr Ser Glu
            740                 745                 750

Glu Glu Gly Asp Glu Val Glu Pro Val Ile Ser Trp Gly
        755                 760                 765

<210> SEQ ID NO 7
<211> LENGTH: 2479
<212> TYPE: DNA
<213> ORGANISM: Penicillium emersonii

<400> SEQUENCE: 7
atgcgcgcag tgcagcttct gcccagcctc gccggcctga ttggcgctgc ctctgccgtt    60
```

-continued

```
ggatgtccgt atctgacggg ccagctcgat gccagagacg tgcacaatcc gcacgagttc    120
cagcgtcgac aggatcccgg agatgcggct gcgtccacag agcagttcct gtcccagttc    180
tatctcaatg acagcaacag ctacatgacc actgatgtcg gcggcccat ctcggatcag     240 aacagtttga aggccggaga gcgcggtcca accctgttgg aggacttcat cttccgtcag    300
aagatccagc actttgatca cgagcgggta ggttgtacca tccatgcgag agagatcgat    360
cgatgttgac gtggtggcag gtcccagaac gcgcagtcca tgctcgagga gccggcgccc    420
acggaacgtt cacttcctac ggaaactggt ccaacatcac tgcggcctcc ttcctgagcg    480
ctgaagggaa ggagaccccc gtgtttgtgc gcttctccac cgtggccgga agtcgaggca    540
gtgcggacac ggcgcgcgat gtgcatggct ttgccaccag gttctacact gacgagggca    600
actttggtac gtcgtctcac aatcctctcg actggcatcg tctgaccgct gagcagatat    660
cgtcggcaac aacattccag tcttcttcat ccaggacgcc attctcttcc ctgatctgat    720
ccatgctgtc aagcccagcc ccgacaacga gatcccccag gctgcgactg ctcatgacac    780
ggcctgggac ttcttcagcc agcagcccag tgcgttcaca cgctcttct gggctatgtc     840 cggccatgga atccctcgct cttttcgcca catggacggc tttggcgtcc acactttccg    900
attcgtgact gacgacggcg cctccaagct ggtcaaattc cactggacct cgctgcaggg    960
ccgggccagc ctggtctggg aggaggcgca agcggcagcg ggaaagaacc tggactatat   1020
gcgccaggac ctctatgaca acatcgaagc cggtcgatat cctgaatggg aggtaggtgg   1080
ccgcattttc tcggcatata tatgtccatg ctgacgttcc tagctgggca ttcaaatcgt   1140
cgacgaggag gatcagctca gtttggatt tgatctgctg gatccaacca agatcattcc    1200
tgttgaatat gtccccatca cgccgcttgg gaagctgcag ctcaaccgga atccgctcaa   1260
ctatttcgcc gagacggagc agataatggt atgtaaacag tttgttgttc gattctttgc   1320
agtagactga cgatacatag ttccaacccg gccatattgt gcgcggaatt gactttaccg   1380
aagaccccct ctccaggga cggctcttct cctatctcga cacgcagttg aatcggaatg    1440
gaggccccaa tttcgagcag cttcccatca atcgtcctag ggtgccatgg cataacaaca   1500
accgtgatgg attcagtaag tttaccccc tgcgctgact ctctgcatgc taactccacc    1560
aggccaagcg tttatccccc tgaacaaggc ggcctacagc ccgaacacgc tcaacaatgg   1620
caaccccaag caggcgaacc agactgtggg cgatggattc ttccaccactc ccggacgtac   1680 gaccagtggc cggctcatgc gcaccgtcag ttcgaccttc tccgacgtct ggtcgcagcc   1740
tcggctgttc tacaactcgc tggtgccggc cgagcagcag ttcctcgtca cgccatccg    1800 tttcgagaac tccaacgtca agagcgaagt ggtccggaac aatgtcatca tccagctcaa   1860
ccgcgtcgat aacgacctcg cccgccgggt tgctcgggtc attggcgttg cagaacccga   1920
gcccgatcca acctattatc acaacaacaa gacggccaac gtgggtacgt ttggcacgcc   1980
gctcaagcgg atcgacggtc tcaaagtcgg tgtgcttgcc acagttggcg acccagacag   2040
tatcagtcag ggccagagcc tcagtgacgc gctctcggac tccaaggtcg atgtcactgt   2100
cgttgctgag tctttcacgg acggggtcga tgcgctctac accaactcgg acgcgaccgg   2160
cttcgacgcc gttatcgtgg ctgatggcgc cgaagggctt tttacccga gtagcttcac    2220 agccaaaccg acgaactcat tctcgacgac aacgctttat ccggccggtc gtccgctgca   2280
gatcctggtc gacgccttcc ggttcggcaa gccgtcggc gctctgggca gcggagctaa     2340
ggcgcttgat gcggcaggta tctcgactag ccggcctggt gtgtacgtcg ccaactcgac   2400
cagcgaggcg ttcacggacg atatcgagga tggtttgcga acgttcaagt tcctcgaccg   2460
```
gtttgcgctg gatgagtga                                                              2479

<210> SEQ ID NO 8
<211> LENGTH: 741
<212> TYPE: PRT
<213> ORGANISM: Penicillium emersonii

<400> SEQUENCE: 8

| | | | | | | | | | | | | | | |
|---|---|---|---|---|---|---|---|---|---|---|---|---|---|---|
| Met | Arg | Ala | Val | Gln | Leu | Leu | Pro | Ser | Leu | Ala | Gly | Leu | Ile | Gly | Ala |
| 1 | | | | 5 | | | | | 10 | | | | | 15 | |
| Ala | Ser | Ala | Val | Gly | Cys | Pro | Tyr | Leu | Thr | Gly | Gln | Leu | Asp | Ala | Arg |
| | | | 20 | | | | | 25 | | | | | 30 | | |
| Asp | Val | His | Asn | Pro | His | Glu | Phe | Gln | Arg | Arg | Gln | Asp | Pro | Gly | Asp |
| | | | 35 | | | | | 40 | | | | | 45 | | |
| Ala | Ala | Ala | Ser | Thr | Glu | Gln | Phe | Leu | Ser | Gln | Phe | Tyr | Leu | Asn | Asp |
| | 50 | | | | | 55 | | | | | 60 | | | | |
| Ser | Asn | Ser | Tyr | Met | Thr | Thr | Asp | Val | Gly | Pro | Ile | Ser | Asp | Gln |
| 65 | | | | | 70 | | | | 75 | | | | | 80 |
| Asn | Ser | Leu | Lys | Ala | Gly | Glu | Arg | Gly | Pro | Thr | Leu | Leu | Glu | Asp | Phe |
| | | | | 85 | | | | | 90 | | | | | 95 | |
| Ile | Phe | Arg | Gln | Lys | Ile | Gln | His | Phe | Asp | His | Glu | Arg | Val | Pro | Glu |
| | | | 100 | | | | | 105 | | | | | 110 | | |
| Arg | Ala | Val | His | Ala | Arg | Gly | Ala | Gly | Ala | His | Gly | Thr | Phe | Thr | Ser |
| | | | 115 | | | | | 120 | | | | | 125 | | |
| Tyr | Gly | Asn | Trp | Ser | Asn | Ile | Thr | Ala | Ala | Ser | Phe | Leu | Ser | Ala | Glu |
| | 130 | | | | | 135 | | | | | 140 | | | | |
| Gly | Lys | Glu | Thr | Pro | Val | Phe | Val | Arg | Phe | Ser | Thr | Val | Ala | Gly | Ser |
| 145 | | | | | 150 | | | | | 155 | | | | | 160 |
| Arg | Gly | Ser | Ala | Asp | Thr | Ala | Arg | Asp | Val | His | Gly | Phe | Ala | Thr | Arg |
| | | | | 165 | | | | | 170 | | | | | 175 | |
| Phe | Tyr | Thr | Asp | Glu | Gly | Asn | Phe | Asp | Ile | Val | Gly | Asn | Asn | Ile | Pro |
| | | | 180 | | | | | 185 | | | | | 190 | | |
| Val | Phe | Phe | Ile | Gln | Asp | Ala | Ile | Leu | Phe | Pro | Asp | Leu | Ile | His | Ala |
| | | | 195 | | | | | 200 | | | | | 205 | | |
| Val | Lys | Pro | Ser | Pro | Asp | Asn | Glu | Ile | Pro | Gln | Ala | Ala | Thr | Ala | His |
| | 210 | | | | | 215 | | | | | 220 | | | | |
| Asp | Thr | Ala | Trp | Asp | Phe | Phe | Ser | Gln | Gln | Pro | Ser | Ala | Leu | His | Thr |
| 225 | | | | | 230 | | | | | 235 | | | | | 240 |
| Leu | Phe | Trp | Ala | Met | Ser | Gly | His | Gly | Ile | Pro | Arg | Ser | Phe | Arg | His |
| | | | | 245 | | | | | 250 | | | | | 255 | |
| Met | Asp | Gly | Phe | Gly | Val | His | Thr | Phe | Arg | Phe | Val | Thr | Asp | Asp | Gly |
| | | | 260 | | | | | 265 | | | | | 270 | | |
| Ala | Ser | Lys | Leu | Val | Lys | Phe | His | Trp | Thr | Ser | Leu | Gln | Gly | Arg | Ala |
| | | | | 275 | | | | | 280 | | | | | 285 | |
| Ser | Leu | Val | Trp | Glu | Glu | Ala | Gln | Ala | Ala | Gly | Lys | Asn | Leu | Asp |
| | 290 | | | | | 295 | | | | | 300 | | | | |
| Tyr | Met | Arg | Gln | Asp | Leu | Tyr | Asp | Asn | Ile | Glu | Ala | Gly | Arg | Tyr | Pro |
| 305 | | | | | 310 | | | | | 315 | | | | | 320 |
| Glu | Trp | Glu | Leu | Gly | Ile | Gln | Ile | Val | Asp | Glu | Asp | Gln | Leu | Lys |
| | | | | 325 | | | | | 330 | | | | | 335 | |
| Phe | Gly | Phe | Asp | Leu | Leu | Asp | Pro | Thr | Lys | Ile | Ile | Pro | Val | Glu | Tyr |
| | | | 340 | | | | | 345 | | | | | 350 | | |
| Val | Pro | Ile | Thr | Pro | Leu | Gly | Lys | Leu | Gln | Leu | Asn | Arg | Asn | Pro | Leu |
| | | | | 355 | | | | | 360 | | | | | 365 | |

-continued

Asn Tyr Phe Ala Glu Thr Glu Gln Ile Met Phe Gln Pro Gly His Ile
        370                 375                 380

Val Arg Gly Ile Asp Phe Thr Glu Asp Pro Leu Leu Gln Gly Arg Leu
385                 390                 395                 400

Phe Ser Tyr Leu Asp Thr Gln Leu Asn Arg Asn Gly Gly Pro Asn Phe
                405                 410                 415

Glu Gln Leu Pro Ile Asn Arg Pro Arg Val Pro Trp His Asn Asn Asn
            420                 425                 430

Arg Asp Gly Phe Ser Gln Ala Phe Ile Pro Leu Asn Lys Ala Ala Tyr
                435                 440                 445

Ser Pro Asn Thr Leu Asn Asn Gly Asn Pro Lys Gln Ala Asn Gln Thr
        450                 455                 460

Val Gly Asp Gly Phe Phe Thr Thr Pro Gly Arg Thr Thr Ser Gly Arg
465                 470                 475                 480

Leu Met Arg Thr Val Ser Ser Thr Phe Ser Asp Val Trp Ser Gln Pro
                485                 490                 495

Arg Leu Phe Tyr Asn Ser Leu Val Pro Ala Glu Gln Gln Phe Leu Val
            500                 505                 510

Asn Ala Ile Arg Phe Glu Asn Ser Asn Val Lys Ser Glu Val Val Arg
        515                 520                 525

Asn Asn Val Ile Ile Gln Leu Asn Arg Val Asp Asn Asp Leu Ala Arg
530                 535                 540

Arg Val Ala Arg Val Ile Gly Val Ala Glu Pro Glu Pro Asp Pro Thr
545                 550                 555                 560

Tyr Tyr His Asn Asn Lys Thr Ala Asn Val Gly Thr Phe Gly Thr Pro
                565                 570                 575

Leu Lys Arg Ile Asp Gly Leu Lys Val Gly Val Leu Ala Thr Val Gly
            580                 585                 590

Asp Pro Asp Ser Ile Ser Gln Gly Gln Ser Leu Ser Asp Ala Leu Ser
        595                 600                 605

Asp Ser Lys Val Asp Val Thr Val Val Ala Glu Ser Phe Thr Asp Gly
610                 615                 620

Val Asp Ala Leu Tyr Thr Asn Ser Asp Ala Thr Gly Phe Asp Ala Val
625                 630                 635                 640

Ile Val Ala Asp Gly Ala Glu Gly Leu Phe Thr Pro Ser Ser Phe Thr
                645                 650                 655

Ala Lys Pro Thr Asn Ser Phe Ser Thr Thr Thr Leu Tyr Pro Ala Gly
            660                 665                 670

Arg Pro Leu Gln Ile Leu Val Asp Ala Phe Arg Phe Lys Pro Val
        675                 680                 685

Gly Ala Leu Gly Ser Gly Ala Lys Ala Leu Asp Ala Ala Gly Ile Ser
690                 695                 700

Thr Ser Arg Pro Gly Val Tyr Val Ala Asn Ser Thr Ser Glu Ala Phe
705                 710                 715                 720

Thr Asp Asp Ile Glu Asp Gly Leu Arg Thr Phe Lys Phe Leu Asp Arg
                725                 730                 735

Phe Ala Leu Asp Glu
            740

<210> SEQ ID NO 9
<211> LENGTH: 860
<212> TYPE: DNA
<213> ORGANISM: Thermus Brockianus

<400> SEQUENCE: 9

```
tagaccgcct gcagattgag ttgcccatgc ccaaggagca ggaccccaac gccgccgccg      60
cggtgcaggc ccttctgggc ggtcgcttcg gggagatgtc caccctgatg aactacatgt     120
accagtcctt caacttccgg gggaagaagg cgcttaagcc ctactacgac ctcatcgcca     180
acatcgccac ggaggagctt ggcacattg agctcgtttc cgccaccatc aacagcctcc      240
tggccaaaaa ccccggaaag gacctggagg aagggggtaga ccccgtgagc gcccccttgg    300
gcttctccaa ggacgcccgc aacgccgccc acttcatcgc cgggggggcc aacaccctgg    360 tgatggggc catgggagag cactggcacg gggagtacgt cttcaccagc ggcaacctca     420
tcctggacct tctccacaac ttcttcctgg aggtggcggc ccgcacccac aagctccggg    480
tctacgagat gacggataac cccgtggccc gggagatgat cggctacctc ctggtgcggg    540
gtggggtcca cgccgccgcc tacggcaagg ccctggaaac ccttaccggg gtggagatga    600
ccaagatgct ccccatcccc cggattgaca acagcaagat ccccgaggcc aagaagtaca    660
tggacctggg cttccaccgc aacctctacc gctttagccc ctccgattac caggacctgg    720
gccttatctg gaatgggggct tcccccgagg acgggagcga ggtggtggtg gtggacggcc    780
cccccacggg cggcccgtg tttgacgccg ccacgacgc cgccgagttc gccccccgagt     840 tccaccccgc cgagctctac                                                 860
```

<210> SEQ ID NO 10
<211> LENGTH: 286
<212> TYPE: PRT
<213> ORGANISM: Thermus Brockianus

<400> SEQUENCE: 10

```
Asp Arg Leu Gln Ile Glu Leu Pro Met Pro Lys Glu Gln Asp Pro Asn
1               5                   10                  15

Ala Ala Ala Ala Val Gln Ala Leu Leu Gly Gly Arg Phe Gly Glu Met
                20                  25                  30

Ser Thr Leu Met Asn Tyr Met Tyr Gln Ser Phe Asn Phe Arg Gly Lys
            35                  40                  45

Lys Ala Leu Lys Pro Tyr Tyr Asp Leu Ile Ala Asn Ile Ala Thr Glu
50                  55                  60

Glu Leu Gly His Ile Glu Leu Val Ser Ala Thr Ile Asn Ser Leu Leu
65                  70                  75                  80

Ala Lys Asn Pro Gly Lys Asp Leu Glu Glu Gly Val Asp Pro Val Ser
                85                  90                  95

Ala Pro Leu Gly Phe Ser Lys Asp Ala Arg Asn Ala Ala His Phe Ile
            100                 105                 110

Ala Gly Gly Ala Asn Thr Leu Val Met Gly Ala Met Gly Glu His Trp
        115                 120                 125

His Gly Glu Tyr Val Phe Thr Ser Gly Asn Leu Ile Leu Asp Leu Leu
    130                 135                 140

His Asn Phe Phe Leu Glu Val Ala Ala Arg Thr His Lys Leu Arg Val
145                 150                 155                 160

Tyr Glu Met Thr Asp Asn Pro Val Ala Arg Glu Met Ile Gly Tyr Leu
                165                 170                 175

Leu Val Arg Gly Gly Val His Ala Ala Ala Tyr Gly Lys Ala Leu Glu
            180                 185                 190

Thr Leu Thr Gly Val Glu Met Thr Lys Met Leu Pro Ile Pro Arg Ile
        195                 200                 205
```

Asp Asn Ser Lys Ile Pro Glu Ala Lys Lys Tyr Met Asp Leu Gly Phe
    210                 215                 220

His Arg Asn Leu Tyr Arg Phe Ser Pro Ser Asp Tyr Gln Asp Leu Gly
225                 230                 235                 240

Leu Ile Trp Asn Gly Ala Ser Pro Glu Asp Gly Ser Glu Val Val Val
                245                 250                 255

Val Asp Gly Pro Pro Thr Gly Gly Pro Val Phe Asp Ala Gly His Asp
            260                 265                 270

Ala Ala Glu Phe Ala Pro Glu Phe His Pro Ala Glu Leu Tyr
            275                 280                 285

<210> SEQ ID NO 11
<211> LENGTH: 1542
<212> TYPE: DNA
<213> ORGANISM: Saccharomyces pastorianus

<400> SEQUENCE: 11

| | | | | |
|---|---|---|---|---|
| atgtcaggac | aagaggagaa | taaagtaaat | tcttctgacg | taagaaagga | tagagttgtg | 60 |
| acgaactcta | ctggtaatcc | catcaatgag | ccatttgtca | cccagcgtgt | tggggagcac | 120 |
| gggcctttgc | ttttacaaga | ttataaccta | ctcgattctt | tggcgcattt | taacagggag | 180 |
| aatattcctc | aaagaaatcc | tcacgcccac | ggttctgggg | ccttcggtta | ttttgaagtg | 240 |
| acagacgata | ttacagatgt | ttgtgggtct | gccatgttta | gcaagatcgg | taagagaacg | 300 |
| aagtgtctga | caagattctc | cactgtgggt | ggtgataaag | gtagtgccga | tactgttcgt | 360 |
| gacccaagag | ggtttgcaac | taaattctac | acagaagaag | gtaatttgga | ttgggtctac | 420 |
| aacaatacac | ctgtattttt | tatcagggat | ccttcgaaat | tcccccattt | tatccacacg | 480 |
| cagaagagaa | acccgcaaac | taatctaaga | gacgctgata | tgttttggga | tttccttacg | 540 |
| actccagaga | atcaagtggc | catccatcaa | gtcatgattc | tcttttcaga | ccgtggtact | 600 |
| cctgcgagct | atcgtaacat | gcacggatat | tctggtcata | cttataaatg | gtcaagtaaa | 660 |
| aacggcgatt | ggcgttatgt | gcaagtccat | attaaaacca | atcaagggt | caagaatttg | 720 |
| actatagacg | aagccactaa | aatcgcaggg | tccaacccag | attactgcca | aaaagacttg | 780 |
| tttgaatcta | tccaaagcgg | taactatcca | tcgtggactg | tttatattca | aacaatgact | 840 |
| gaacaggagg | ccaagaattt | accatttccg | gtctttgact | tgaccaaggt | atggcctcaa | 900 |
| aagcaattcc | cattacgtcg | tgtaggcaaa | cttgttctga | tgaaaatcc | actgaatttc | 960 |
| ttcgcacaag | tggaacaagc | agcgtttgcc | cctagtacta | ctgtcccata | ccaagaagcc | 1020 |
| agtgctgatc | cggtgctaca | agctcgatta | ttttcttatg | cagatgctca | cagatacaga | 1080 |
| ctgggccca | atttccatca | aatacccgtc | aactgtccct | atgcctccaa | gttttttaac | 1140 |
| cctgccatca | gagatggccc | aatgaacgta | aatggaaatt | ttggttcaga | acctacctat | 1200 |
| ttagccaacg | acaaatcata | ctcgtatatt | cagcaagaaa | gacctattca | acaacatcaa | 1260 |
| gaagtatgga | acggacccgc | tatcccttac | cactgggcaa | catctccagg | tgatgtcgat | 1320 |
| tatgttcaag | ctaggaattt | gtaccgcgtc | ttagggaagc | aacctggaca | caaaagaac | 1380 |
| ctagctcaca | catcggtat | ccatgtagag | ggcgcctgcc | ctggaatcca | gcaacgggtt | 1440 |
| tacgatatgt | tgcccgcgt | agataaggga | ctatctgatg | cgatcaagaa | agaagcagag | 1500 |
| gcaaaacacg | ctgctgaact | ttcaaataac | tctaagtttt | ga | | 1542 |

<210> SEQ ID NO 12
<211> LENGTH: 513
<212> TYPE: PRT

<213> ORGANISM: Saccharomyces pastorianus

<400> SEQUENCE: 12

```
Met Ser Gly Gln Glu Asn Lys Val Asn Ser Asp Val Arg Lys
1               5                   10                  15

Asp Arg Val Val Thr Asn Ser Thr Gly Asn Pro Ile Asn Glu Pro Phe
            20                  25                  30

Val Thr Gln Arg Val Gly Glu His Gly Pro Leu Leu Leu Gln Asp Tyr
            35                  40                  45

Asn Leu Leu Asp Ser Leu Ala His Phe Asn Arg Glu Asn Ile Pro Gln
    50                  55                  60

Arg Asn Pro His Ala His Gly Ser Gly Ala Phe Gly Tyr Phe Glu Val
65                  70                  75                  80

Thr Asp Asp Ile Thr Asp Val Cys Gly Ser Ala Met Phe Ser Lys Ile
                85                  90                  95

Gly Lys Arg Thr Lys Cys Leu Thr Arg Phe Ser Thr Val Gly Gly Asp
                100                 105                 110

Lys Gly Ser Ala Asp Thr Val Arg Asp Pro Arg Gly Phe Ala Thr Lys
            115                 120                 125

Phe Tyr Thr Glu Glu Gly Asn Leu Asp Trp Val Tyr Asn Asn Thr Pro
    130                 135                 140

Val Phe Phe Ile Arg Asp Pro Ser Lys Phe Pro His Phe Ile His Thr
145                 150                 155                 160

Gln Lys Arg Asn Pro Gln Thr Asn Leu Arg Asp Ala Asp Met Phe Trp
                165                 170                 175

Asp Phe Leu Thr Thr Pro Glu Asn Gln Val Ala Ile His Gln Val Met
                180                 185                 190

Ile Leu Phe Ser Asp Arg Gly Thr Pro Ala Ser Tyr Arg Asn Met His
            195                 200                 205

Gly Tyr Ser Gly His Thr Tyr Lys Trp Ser Ser Lys Asn Gly Asp Trp
    210                 215                 220

Arg Tyr Val Gln Val His Ile Lys Thr Asn Gln Gly Val Lys Asn Leu
225                 230                 235                 240

Thr Ile Asp Glu Ala Thr Lys Ile Ala Gly Ser Asn Pro Asp Tyr Cys
                245                 250                 255

Gln Lys Asp Leu Phe Glu Ser Ile Gln Ser Gly Asn Tyr Pro Ser Trp
                260                 265                 270

Thr Val Tyr Ile Gln Thr Met Thr Glu Gln Glu Ala Lys Asn Leu Pro
            275                 280                 285

Phe Ser Val Phe Asp Leu Thr Lys Val Trp Pro Gln Lys Gln Phe Pro
    290                 295                 300

Leu Arg Arg Val Gly Lys Leu Val Leu Asn Glu Asn Pro Leu Asn Phe
305                 310                 315                 320

Phe Ala Gln Val Glu Gln Ala Ala Phe Ala Pro Ser Thr Thr Val Pro
                325                 330                 335

Tyr Gln Glu Ala Ser Ala Asp Pro Val Leu Gln Ala Arg Leu Phe Ser
                340                 345                 350

Tyr Ala Asp Ala His Arg Tyr Arg Leu Gly Pro Asn Phe His Gln Ile
            355                 360                 365

Pro Val Asn Cys Pro Tyr Ala Ser Lys Phe Asn Pro Ala Ile Arg
    370                 375                 380

Asp Gly Pro Met Asn Val Asn Gly Asn Phe Gly Ser Glu Pro Thr Tyr
385                 390                 395                 400
```

```
Leu Ala Asn Asp Lys Ser Tyr Ser Tyr Ile Gln Gln Glu Arg Pro Ile
            405                 410                 415

Gln Gln His Gln Glu Val Trp Asn Gly Pro Ala Ile Pro Tyr His Trp
        420                 425                 430

Ala Thr Ser Pro Gly Asp Val Asp Tyr Val Gln Ala Arg Asn Leu Tyr
    435                 440                 445

Arg Val Leu Gly Lys Gln Pro Gly Gln Gln Lys Asn Leu Ala His Asn
450                 455                 460

Ile Gly Ile His Val Glu Gly Ala Cys Pro Gly Ile Gln Gln Arg Val
465                 470                 475                 480

Tyr Asp Met Phe Ala Arg Val Asp Lys Gly Leu Ser Asp Ala Ile Lys
                485                 490                 495

Lys Glu Ala Glu Ala Lys His Ala Ala Glu Leu Ser Asn Asn Ser Lys
            500                 505                 510

Phe

<210> SEQ ID NO 13
<211> LENGTH: 1548
<212> TYPE: DNA
<213> ORGANISM: Saccharomyces pastorianus

<400> SEQUENCE: 13
atgtcgaaat tgggacaaga aaaaaatgaa gtaaattcct ctgatgtaag agaggataga      60
gttgtgacaa actccactgg taatccaatc aatgaaccat ttgtcaccca acgtattgga     120
gaacatggcc ctttgctttt gcaagattat aacttaattg attctttggc tcatttcaac     180
agggaaaata ttcctcaaag gaatccacat gctcatggtt ctggtgcctt cggctatttt     240
gaagtaaccg atgacattac tgatatctgc gggtctgcta tgtttagtaa aattgggaaa     300
agaacgaaat gtctaacaag atttcgact gtgggtggtg ataaaggtag tgccgacacg      360
gttcgtgatc caaggggggtt tgccaccaaa ttctacactg aagaaggtaa tttagattgg     420
gtctacaata atacaccggt attctttatc agagacccct ccaagttccc tcactttatc     480
cacacacaga agagaaaccc acaaaccaac ctaagggatg ctgacatgtt ttgggatttc     540
ctcaccactc ctgaaaatca ggtggccatt catcaagtaa tgatcctttt ttcagaccgt     600 ggtaccctg ccaactaccg tagtatgcat ggttattctg gtcatacct aaatggtcc       660 aataaaaacg gagattggca ttatgtgcaa gttcatatca aaaccgatca aggaataaag     720
aatttgacca tagaagaggc taccaaaatt gcgggatcca atccagatta ctgccagcag     780
gatttatttg aggctattca gaatggaaac tatccttcct ggacagttta tattcaaaca     840
atgaccgaac gcgatgccaa aaaattacca ttttcagtct ttgatttgac taaagtatgg     900
cctcaggggc aattcccttt acggcgtgtg ggtaagattg ttttgaacga gaatccactg     960
aacttcttcg cacaggtgga acaagctgcc ttcgcccca gtaccacggt tccttaccaa    1020
gaagcaagcg ctgatccagt attacaggcc cgtttgtttt catatgcgga tgctcataga    1080
tacaggctag gtcctaactt ccatcaaata cccgtaaact gtccatatgc atctaaattt    1140
ttcaatcccg ctatcagaga tggaccgatg aatgttaacg gcaacttcgg ctcagaacct    1200
acatatttgg ccaatgataa atcgtacacg tatatccaac aggacagacc cattcaacaa    1260
caccaagagg tatggaatgg gccagctatc ccttatcatt gggcaacatc cccaggtgat    1320
gtagatttcg tgcaagcaag aaatctctat cgcgttttgg gtaaacaacc tggacagcaa    1380
aagaacttgg catataacat cggcattcat gtagaaggcg cctgtcctca aatacagcag    1440
```

```
cgcgtttatg atatgtttgc tcgtgttgat aagggactat ctgaggcaat taaaaaagta      1500
gctgaggcaa aacatgcttc tgagctttcg agtaactcca aattttga                   1548

<210> SEQ ID NO 14
<211> LENGTH: 515
<212> TYPE: PRT
<213> ORGANISM: Saccharomyces pastorianus

<400> SEQUENCE: 14

Met Ser Lys Leu Gly Gln Glu Lys Asn Glu Val Asn Ser Ser Asp Val
1               5                   10                  15

Arg Glu Asp Arg Val Val Thr Asn Ser Thr Gly Asn Pro Ile Asn Glu
            20                  25                  30

Pro Phe Val Thr Gln Arg Ile Gly Glu His Gly Pro Leu Leu Leu Gln
        35                  40                  45

Asp Tyr Asn Leu Ile Asp Ser Leu Ala His Phe Asn Arg Glu Asn Ile
    50                  55                  60

Pro Gln Arg Asn Pro His Ala His Gly Ser Gly Ala Phe Gly Tyr Phe
65                  70                  75                  80

Glu Val Thr Asp Asp Ile Thr Asp Ile Cys Gly Ser Ala Met Phe Ser
                85                  90                  95

Lys Ile Gly Lys Arg Thr Lys Cys Leu Thr Arg Phe Ser Thr Val Gly
            100                 105                 110

Gly Asp Lys Gly Ser Ala Asp Thr Val Arg Asp Pro Arg Gly Phe Ala
        115                 120                 125

Thr Lys Phe Tyr Thr Glu Glu Gly Asn Leu Asp Trp Val Tyr Asn Asn
    130                 135                 140

Thr Pro Val Phe Phe Ile Arg Asp Pro Ser Lys Phe Pro His Phe Ile
145                 150                 155                 160

His Thr Gln Lys Arg Asn Pro Gln Thr Asn Leu Arg Asp Ala Asp Met
                165                 170                 175

Phe Trp Asp Phe Leu Thr Thr Pro Glu Asn Gln Val Ala Ile His Gln
            180                 185                 190

Val Met Ile Leu Phe Ser Asp Arg Gly Thr Pro Ala Asn Tyr Arg Ser
        195                 200                 205

Met His Gly Tyr Ser Gly His Thr Tyr Lys Trp Ser Asn Lys Asn Gly
    210                 215                 220

Asp Trp His Tyr Val Gln Val His Ile Lys Thr Asp Gln Gly Ile Lys
225                 230                 235                 240

Asn Leu Thr Ile Glu Glu Ala Thr Lys Ile Ala Gly Ser Asn Pro Asp
                245                 250                 255

Tyr Cys Gln Gln Asp Leu Phe Glu Ala Ile Gln Asn Gly Asn Tyr Pro
            260                 265                 270

Ser Trp Thr Val Tyr Ile Gln Thr Met Thr Glu Arg Asp Ala Lys Lys
        275                 280                 285

Leu Pro Phe Ser Val Phe Asp Leu Thr Lys Val Trp Pro Gln Gly Gln
    290                 295                 300

Phe Pro Leu Arg Arg Val Gly Lys Ile Val Leu Asn Glu Asn Pro Leu
305                 310                 315                 320

Asn Phe Phe Ala Gln Val Glu Gln Ala Ala Phe Ala Pro Ser Thr Thr
                325                 330                 335

Val Pro Tyr Gln Glu Ala Ser Ala Asp Pro Val Leu Gln Ala Arg Leu
            340                 345                 350

Phe Ser Tyr Ala Asp Ala His Arg Tyr Arg Leu Gly Pro Asn Phe His
```

```
                355                 360                 365
Gln Ile Pro Val Asn Cys Pro Tyr Ala Ser Lys Phe Phe Asn Pro Ala
        370                 375                 380

Ile Arg Asp Gly Pro Met Asn Val Asn Gly Asn Phe Gly Ser Glu Pro
385                 390                 395                 400

Thr Tyr Leu Ala Asn Asp Lys Ser Tyr Thr Tyr Ile Gln Gln Asp Arg
                405                 410                 415

Pro Ile Gln Gln His Gln Glu Val Trp Asn Gly Pro Ala Ile Pro Tyr
            420                 425                 430

His Trp Ala Thr Ser Pro Gly Asp Val Asp Phe Val Gln Ala Arg Asn
        435                 440                 445

Leu Tyr Arg Val Leu Gly Lys Gln Pro Gly Gln Gln Lys Asn Leu Ala
    450                 455                 460

Tyr Asn Ile Gly Ile His Val Glu Gly Ala Cys Pro Gln Ile Gln Gln
465                 470                 475                 480

Arg Val Tyr Asp Met Phe Ala Arg Val Asp Lys Gly Leu Ser Glu Ala
                485                 490                 495

Ile Lys Lys Val Ala Glu Ala Lys His Ala Ser Glu Leu Ser Ser Asn
            500                 505                 510

Ser Lys Phe
        515

<210> SEQ ID NO 15
<211> LENGTH: 2403
<212> TYPE: DNA
<213> ORGANISM: Penicillium pinophilum

<400> SEQUENCE: 15
atgcgaggat tatactccct cggcgccttc gccagtctca ttgcggcggc ttcggctgca      60
tgcccaatgc tgactggcga atcccagct ggtagtgttg ccaatcctca tcatcacgga     120
aagcgtgacg attcaaatgc ttcctccgaa acagaagcct ttctgtccga gttctacctc    180
aacgacaacg atgcctatct caccaccgat gtaggcggtc cgatcgagga tcaaaacagt    240
ttgaaggccg gcattcgtgg atcgaccctc ttggaagact tcatcttccg tcagaaaatc    300
cagcattttg atcatgagcg tgtaggttat ccattctatc acgtacttca ggggtagttc    360
tgacatgccc aggtcccgga acgtgccgtg catgctcgag gtgcaggtgc tcatggtgta    420
tttacttcat atgccgactg gtccaacatc actgctgctt cattttggg agcttccgga     480 aaggaaacgc ccacatttgt ccgcttctcg actgttgcag gcagccgagg aagtgccgac    540
accgctcgtg acgttcacgg atttgctact cgcttctata ctgacgaggg aaactatggt    600
agcctttctc tttgactcgt ccatagatag ggatgtaact gacttcaaca gacattgttg    660
gaaacaacat tcctgtcttc ttcatccaag atgctatctt attcccagat ctcatccata    720
gcgttaagcc acagccagcc aatgaaatcc cacaggctgc tactgcacac gacacggcct    780
atgacttctt tggtcaacag ccaagcactc tgcataccct cttctgggca atggcaggcc    840
atggtatccc acggtctttc cgtcatgttg acggattcgg tgtccacacc tatcggttcg    900
tgacagatga tggctcgtcc aagttggtca aatttcactg acatcgctg caaggtcggg      960 ccagtctggt ctgggaggaa gctcaggcca ctgctggcaa aaatgccgac tttatgagac    1020
aggatctgta tgatagcatt gaggctggcc gttatccaga gtggaggta tgtaccaccg     1080 aattcatgga aagtactcga ctaacgtgaa cagctcggcg tgcaaataat tgaggagtcg    1140
gatgtcttaa gctacggatt tgacctgttg gatccaacca agattcttcc ggttgaaaaa    1200
```

```
gttccaatta ctgcgctcgg aaaaatgcaa ctcaaccgta atccattgaa ttactttgcc    1260
gagacagagc aagtcatggt aagtcgacct tccggcactc gagtcatttc ctactaacgt    1320
ggatagttcc aacctggcca cattgttcgt ggtatcgact tcacctatta tcctcttctc    1380
cagggtcgtt tattctccta cctcgatact cagctgaatc gcaatggtgg tcccaacttt    1440
gaacaaattc caatcaatcg tccgcgtgtt cctatccaca acaacaaccg cgatggattc    1500
gcccaaatgt ttattccttt gaaccaggca gcatattcac ccaacacctt gaataatggc    1560
tctcctcgac aagccaacga gactgtcgga atggcttct ttaccgcccc cgggcgctcc    1620
gcagatggac accttgttcg cgctacgagc ccaacatttg ccgacgtgtg gtctcagcct    1680
ggcttgtttt acaactcctt gacggctacc gaacaacagt tcgtgatcaa tgctttgcgt    1740
ttcgaattgt ctaatgtaaa gagcgaggat gttaaaagca atttcatcac acagataaat    1800
cgcgtaaaca cacgttagc aacacttgtg gcttctgcaa ttggagtctc cgcgcccgaa    1860
cccgactcta catactacca cagcaataag acgtctaatg tcggaacatt cggtactccg    1920
ttgaaaaagc ttgacggtct caaggtcgga gtccttgctt cggtgaacgg tgaaagtagt    1980
attgccgagg acaagcatt ggcacaaagc ctagcgggct cgaacgtgga cgtcgttatc    2040
gtcgccgagc atcttacttc gaacgtgtca gctacatact ctggatcaga cgcaacgaac    2100
tttgatgctg ttattgtcag ctcagggggct gaaggtctct ttggacctca aacctttaca    2160
gccgaatcca atacaacact ttatccggca ggccgtccta gccagatttt ggtcgatgcc    2220
ttccgctttg gcaagccggt tggagcagtt ggtggtgcca gtgcagctct gtcagcggtg    2280
gatatcagta ctgatcgtag tggtgtgatt actggtgatt ccgtcagtga cgactttgtc    2340
aagcagctaa cggaggacct tgccacattc aaattcttgg accgattcgc tgtggatgag    2400
tag                                                                  2403
```

<210> SEQ ID NO 16
<211> LENGTH: 692
<212> TYPE: PRT
<213> ORGANISM: Penicillium pinophilum

<400> SEQUENCE: 16

Met Arg Gly Leu Tyr Ser Leu Gly Ala Phe Ala Ser Leu Ile Ala Ala
1               5                   10                  15

Ala Ser Ala Ala Cys Pro Met Leu Thr Gly Glu Ile Pro Ala Gly Ser
                20                  25                  30

Val Ala Asn Pro His His Gly Lys Arg Asp Asp Ser Asn Ala Ser
        35                  40                  45

Ser Glu Thr Glu Ala Phe Leu Ser Glu Phe Tyr Leu Asn Asp Asn Asp
    50                  55                  60

Ala Tyr Leu Thr Thr Asp Val Gly Gly Pro Ile Glu Asp Gln Asn Ser
65                  70                  75                  80

Leu Lys Ala Gly Ile Arg Gly Ser Thr Leu Leu Glu Asp Phe Ile Phe
                85                  90                  95

Arg Gln Lys Ile Gln His Phe Asp His Glu Arg Val Pro Glu Arg Ala
                100                 105                 110

Val His Ala Arg Gly Ala Gly Ala His Gly Val Phe Thr Ser Tyr Ala
        115                 120                 125

Asp Trp Ser Asn Ile Thr Ala Ala Ser Phe Leu Gly Ala Ser Gly Lys
    130                 135                 140

Glu Thr Pro Thr Phe Val Arg Phe Ser Thr Val Ala Gly Ser Arg Gly

```
                145                 150                 155                 160
        Ser Ala Asp Thr Ala Arg Asp Val His Gly Phe Ala Thr Arg Phe Tyr
                        165                 170                 175

Thr Asp Glu Gly Asn Tyr Asp Ile Val Gly Asn Asn Ile Pro Val Phe
                        180                 185                 190

Phe Ile Gln Asp Ala Ile Leu Phe Pro Asp Leu Ile His Ser Val Lys
                        195                 200                 205

Pro Gln Pro Ala Asn Glu Ile Pro Gln Ala Ala Thr Ala His Asp Thr
                        210                 215                 220

Ala Tyr Asp Phe Phe Gly Gln Gln Pro Ser Thr Leu His Thr Leu Phe
        225                 230                 235                 240

Trp Ala Met Ala Gly His Gly Ile Pro Arg Ser Phe Arg His Val Asp
                        245                 250                 255

Gly Phe Gly Val His Thr Tyr Arg Phe Val Thr Asp Asp Gly Ser Ser
                        260                 265                 270

Lys Leu Val Lys Phe His Trp Thr Ser Leu Gln Gly Arg Ala Ser Leu
                        275                 280                 285

Val Trp Glu Glu Ala Gln Ala Thr Ala Gly Lys Asn Ala Asp Phe Met
                        290                 295                 300

Arg Gln Asp Leu Tyr Asp Ser Ile Glu Ala Gly Arg Tyr Pro Glu Trp
        305                 310                 315                 320

Glu Leu Gly Val Gln Ile Ile Glu Ser Asp Val Leu Ser Tyr Gly
                        325                 330                 335

Phe Asp Leu Leu Asp Pro Thr Lys Ile Leu Pro Val Glu Lys Val Pro
                        340                 345                 350

Ile Thr Ala Leu Gly Lys Met Gln Leu Asn Arg Asn Pro Leu Asn Tyr
                        355                 360                 365

Phe Ala Glu Thr Glu Gln Val Met Phe Gln Pro Gly His Ile Val Arg
                        370                 375                 380

Gly Ile Asp Phe Thr Tyr Tyr Pro Leu Leu Gln Gly Arg Leu Phe Ser
        385                 390                 395                 400

Tyr Leu Asp Thr Gln Leu Asn Arg Asn Gly Gly Pro Asn Phe Glu Gln
                        405                 410                 415

Ile Pro Ile Asn Arg Pro Arg Val Pro Ile His Asn Asn Arg Asp
                        420                 425                 430

Gly Phe Ala Gln Met Phe Ile Pro Leu Asn Gln Ala Ala Tyr Ser Pro
                        435                 440                 445

Asn Thr Leu Asn Asn Gly Ser Pro Arg Gln Ala Asn Glu Thr Val Gly
                        450                 455                 460

Asn Gly Phe Phe Thr Ala Pro Gly Arg Ser Ala Asp Gly His Leu Val
        465                 470                 475                 480

Arg Ala Thr Ser Pro Thr Phe Ala Asp Val Trp Ser Gln Pro Gly Leu
                        485                 490                 495

Phe Tyr Asn Ser Leu Thr Ala Thr Glu Gln Gln Phe Val Ile Asn Ala
                        500                 505                 510

Leu Arg Phe Glu Leu Ser Asn Val Lys Ser Glu Asp Val Lys Ser Asn
                        515                 520                 525

Phe Ile Thr Gln Ile Asn Arg Val Asn Asn Thr Leu Ala Thr Leu Val
                        530                 535                 540

Ala Ser Ala Ile Gly Val Ser Ala Pro Glu Pro Asp Ser Thr Tyr Tyr
        545                 550                 555                 560

His Ser Asn Lys Thr Ser Asn Val Gly Thr Phe Gly Thr Pro Leu Lys
                        565                 570                 575
```

```
Lys Leu Asp Gly Leu Lys Val Gly Val Leu Ala Ser Val Asn Gly Glu
            580                 585                 590

Ser Ser Ile Ala Glu Gly Gln Ala Leu Ala Gln Ser Leu Ala Gly Ser
            595                 600                 605

Asn Val Asp Val Val Ile Val Ala Glu His Leu Thr Ser Asn Val Ser
610                 615                 620

Ala Thr Tyr Ser Gly Ser Asp Ala Thr Asn Phe Asp Ala Val Ile Val
625                 630                 635                 640

Ser Ser Gly Ala Glu Gly Leu Phe Gly Pro Gln Thr Phe Thr Ala Glu
                645                 650                 655

Ser Asn Thr Thr Leu Tyr Pro Ala Gly Arg Pro Ser Gln Ile Leu Val
            660                 665                 670

Asp Ala Phe Arg Phe Gly Lys Pro Val Gly Ala Val Gly Gly Ala Ser
            675                 680                 685

Ala Ala Leu Ser
            690

<210> SEQ ID NO 17
<211> LENGTH: 2749
<212> TYPE: DNA
<213> ORGANISM: Humicola grisea

<400> SEQUENCE: 17
```

| | |
|---|---:|
| atgaacagag tcacgaatct cctcgcctgg gccggcgcga tagggctcgc ccaagcaaca | 60 |
| tgccccttcg cggaccctgc cgctctgtat aggcgtcagg atactaccag cggccagtcg | 120 |
| ccacttgcag catacgaggt ggatgacagc accggatacc tgacctccga tgttggcggg | 180 |
| cccattcagg accagaccag cctcaaggca ggcatccggg gtccgacccT tcttgaggac | 240 |
| tttatgttcc gccagaagat ccagcacttc gaccatgaac gggtaaggac ataatgctca | 300 |
| cacgagcggc tgcgtaccta tttattttga acgggtaagg acataatgct cacacgagcg | 360 |
| gctgcgtacc tatttatttc gagagatgg gctggctggc tggctgtgat gcctgagttt | 420 |
| ggggacatac ggagtacctt actgacgcgc taatccactc caggttcccg aaagggcggt | 480 |
| ccatgctcga ggcgctggag cacacgggac cttcacgagt tacgccgact ggagtaacat | 540 |
| caccgcggcg tcctttctga cgccacagg aaagcagacg ccggtgtttg tccggttctc | 600 |
| gaccgttgct gggtctcgag ggagcgcaga cacggcgaga cgttcatg gtttcgcgac | 660 |
| gcggttgtaa gttttgttgt gtttcattcg ttccggtctg tagaggaggg ttaggatatg | 720 |
| agctaacgtg tgtgtgtgtg tgtgaagtta cactgatgaa ggcaactttg gtacgtccca | 780 |
| cgcatggtcc tcaattctct tatctggcag cgatgtggtc attgtcgacg ttgctaactt | 840 |
| gcgtagatat cgtcggaaac aacatcccgg tattcttcat tcaagatgca atccagttcc | 900 |
| ctgaccttat ccactcggtc aagccgagtc agacaacga gattccccaa gcggcgacgg | 960 |
| ctcatgattc agcttgggac ttcttcagcc agcagccaag cgccatggta agcaatggac | 1020 |
| caaggagccg cacctggggt gacataccag ggagtacacg gggcgttccg atgaccctcg | 1080 |
| tgtgaccaag gcagtacaac actccacgga ggactcgaag agattcggaa atatggaaca | 1140 |
| cagaactgac aggatggtag cacacgttgt tctgggccat gtctggccac ggaatccctc | 1200 |
| gcagctatcg ccatatggta cgtttgcctg gctgagatga ccgtgaatcc atttctaacc | 1260 |
| tcaagtccag gatggcttcg gcgtccacac gttccggttt gtcaaagatg acggctcgtc | 1320 |
| caagttgatc aagtggcatt tcaagtcacg ccagggaaag gcgagtctag tctgggaaga | 1380 |

-continued

```
ggcgcaggtt ctttctggca agaatgccga cttccaccgt caggacctct gggatgctat    1440
tgagtccggg aacggaccag aatgggatgt ctgcgtccag attgtcgatg agtcccaggc    1500
gcaagccttt ggcttcgact tgctggaccc gacaaagatc atccccgagg agtacgcccc    1560
cttgacgaaa ctggggctct tgaagctgga tcgcaatccg accaactact cgccgagac    1620 ggagcaggtc atgttccaac ccggtcatat agtccgcggc gtcgacttca cggaggatcc    1680
cctgctacag ggacgtctct tctcgtacct tgacacgcag ctgaaccgga atggcgggcc    1740
caactttgag cagctgccca tcaacatgcc gcgggtgccg attcacaaca ataatcgcga    1800
cggcgccggc cagatgttca tccacaggaa caagtatcct tgtaagtacc tcttttgcct    1860
cgatcgttgt ggtgccggct tgctgacaga cgcagacact cccaacaccc tgaacagtgg    1920
ttatccgcgg caagccaacc aaaatgccgg acgcggattc ttcacagcgc ctggccgtac    1980
cgtcagcggt gccctcgtcc gtgaggtgtc gccaacattc aacgaccact ggtcgcagcc    2040
ccgtctcttc ttcaactccc tcactcccgt cgaacagcag ttcctcgtca acgccatgcg    2100
cttcgaaatc agccttgtga agtcggaaga atgcaggaag aacgtgctca cccagctcaa    2160
ccgcgtcagc catgatgtgg ccgtgcgcgt ggccgccgct atcggcctcg ccgcgcccga    2220
cgcggacgac acatactacc acaacaacaa gacggctggc gtctcgatcc ttggaagcgg    2280
gcccttgcct accatcaaga ctctccgcgt cggcatcctg gctaccacga gcgagtcgag    2340
cgcgctggat caggcagccc agctccgcac ccgtctggaa aaggacgggc ttgtggtcac    2400
ggttgtggct gaaacgctgc gcgagggggt agaccagaca tactcgacgg cggatgccac    2460
gggtttcgac ggcgttgttg ttgtggacgg ggcggcggcg ctgtttgcca gcaccgcgtc    2520
gtcgccgttg ttcccgacgg gcaggccgtt gcagatcttt gtggacgcgt atcggtgggg    2580
aaagccggtc ggtgtgtgtg gtgggaagtc gagcgaggtg ttggatgcgg cggatgttcc    2640
ggaaaatggg gacggggtgt attcggagga gtcggtggac aagtttgtgg aggagtttga    2700 gaagggggttg gctactttca gggtgagtct tggtgccttt gttttttga              2749
```

<210> SEQ ID NO 18
<211> LENGTH: 684
<212> TYPE: PRT
<213> ORGANISM: Humicola grisea

<400> SEQUENCE: 18

```
Met Asn Arg Val Thr Asn Leu Leu Ala Trp Ala Gly Ala Ile Gly Leu
1               5                  10                  15

Ala Gln Ala Thr Cys Pro Phe Asp Pro Ala Leu Tyr Arg Arg
            20                  25                  30

Gln Asp Thr Thr Ser Gly Gln Ser Pro Leu Ala Ala Tyr Glu Val Asp
        35                  40                  45

Asp Ser Thr Gly Tyr Leu Thr Ser Asp Val Gly Pro Ile Gln Asp
    50                  55                  60

Gln Thr Ser Leu Lys Ala Gly Ile Arg Gly Pro Thr Leu Leu Glu Asp
65                  70                  75                  80

Phe Met Phe Arg Gln Lys Ile Gln His Phe Asp His Glu Arg Val Pro
                85                  90                  95

Glu Arg Ala Val His Ala Arg Gly Ala Gly Ala His Gly Thr Phe Thr
            100                 105                 110

Ser Tyr Ala Asp Trp Ser Asn Ile Thr Ala Ala Ser Phe Leu Asn Ala
        115                 120                 125

Thr Gly Lys Gln Thr Pro Val Phe Val Arg Phe Ser Thr Val Ala Gly
```

```
                130                 135                 140
Ser Arg Gly Ser Ala Asp Thr Ala Arg Asp Val His Gly Phe Ala Thr
145                 150                 155                 160

Arg Phe Tyr Thr Asp Glu Gly Asn Phe Asp Ile Val Gly Asn Asn Ile
                165                 170                 175

Pro Val Phe Phe Ile Gln Asp Ala Ile Gln Phe Pro Asp Leu Ile His
                180                 185                 190

Ser Val Lys Pro Ser Pro Asp Asn Glu Ile Pro Gln Ala Ala Thr Ala
                195                 200                 205

His Asp Ser Ala Trp Asp Phe Phe Ser Gln Gln Pro Ser Ala Met His
210                 215                 220

Thr Leu Phe Trp Ala Met Ser Gly His Gly Ile Pro Arg Ser Tyr Arg
225                 230                 235                 240

His Met Asp Gly Phe Gly Val His Thr Phe Arg Phe Val Lys Asp Asp
                245                 250                 255

Gly Ser Ser Lys Leu Ile Lys Trp His Phe Lys Ser Arg Gln Gly Lys
                260                 265                 270

Ala Ser Leu Val Trp Glu Ala Gln Val Leu Ser Gly Lys Asn Ala
                275                 280                 285

Asp Phe His Arg Gln Asp Leu Trp Asp Ala Ile Glu Ser Gly Asn Gly
                290                 295                 300

Pro Glu Trp Asp Val Cys Val Gln Ile Val Asp Glu Ser Gln Ala Gln
305                 310                 315                 320

Ala Phe Gly Phe Asp Leu Leu Asp Pro Thr Lys Ile Ile Pro Glu Glu
                325                 330                 335

Tyr Ala Pro Leu Thr Lys Leu Gly Leu Leu Lys Leu Asp Arg Asn Pro
                340                 345                 350

Thr Asn Tyr Phe Ala Glu Thr Glu Gln Val Met Phe Gln Pro Gly His
                355                 360                 365

Ile Val Arg Gly Val Asp Phe Thr Glu Asp Pro Leu Leu Gln Gly Arg
                370                 375                 380

Leu Phe Ser Tyr Leu Asp Thr Gln Leu Asn Arg Asn Gly Gly Pro Asn
385                 390                 395                 400

Phe Glu Gln Leu Pro Ile Asn Met Pro Arg Val Pro Ile His Asn Asn
                405                 410                 415

Asn Arg Asp Gly Ala Gly Gln Met Phe Ile His Arg Asn Lys Tyr Pro
                420                 425                 430

Tyr Thr Pro Asn Thr Leu Asn Ser Gly Tyr Pro Arg Gln Ala Asn Gln
                435                 440                 445

Asn Ala Gly Arg Gly Phe Phe Thr Ala Pro Gly Arg Thr Val Ser Gly
                450                 455                 460

Ala Leu Val Arg Glu Val Ser Pro Thr Phe Asn Asp His Trp Ser Gln
465                 470                 475                 480

Pro Arg Leu Phe Phe Asn Ser Leu Thr Pro Val Glu Gln Gln Phe Leu
                485                 490                 495

Val Asn Ala Met Arg Phe Glu Ile Ser Leu Val Lys Ser Glu Glu Cys
                500                 505                 510

Arg Lys Asn Val Leu Thr Gln Leu Asn Arg Val Ser His Asp Val Ala
                515                 520                 525

Val Arg Val Ala Ala Ile Gly Leu Ala Ala Pro Asp Ala Asp
                530                 535                 540

Thr Tyr Tyr His Asn Asn Lys Thr Ala Gly Val Ser Ile Leu Gly Ser
545                 550                 555                 560
```

```
Gly Pro Leu Pro Thr Ile Lys Thr Leu Arg Val Gly Ile Leu Ala Thr
                565                 570                 575

Thr Ser Glu Ser Ser Ala Leu Asp Gln Ala Ala Gln Leu Arg Thr Arg
            580                 585                 590

Leu Glu Lys Asp Gly Leu Val Val Thr Val Val Ala Glu Thr Leu Arg
        595                 600                 605

Glu Gly Val Asp Gln Thr Tyr Ser Thr Ala Asp Ala Thr Gly Phe Asp
    610                 615                 620

Gly Val Val Val Asp Gly Ala Ala Leu Phe Ala Ser Thr Ala
625                 630                 635                 640

Ser Ser Pro Leu Phe Pro Thr Gly Arg Pro Leu Gln Ile Phe Val Asp
                645                 650                 655

Ala Tyr Arg Trp Gly Lys Pro Val Gly Val Cys Gly Gly Lys Ser Ser
                660                 665                 670

Glu Val Leu Asp Ala Ala Asp Val Pro Glu Asn Gly
            675                 680

<210> SEQ ID NO 19
<211> LENGTH: 2362
<212> TYPE: DNA
<213> ORGANISM: Thielavia terrestris

<400> SEQUENCE: 19
cgcaagatcg aagcggtcca gattcatgac cttgtcccac gcggccacga agtccttgac      60
gaacttttcc tgaccccctg cgctggcata caccctcggcg atggcgcgca gctcggcatg     120
cgagccaaac acgagatcgg cccgcgtggc cgtccacttc ttggcgcccg tcgcacggtc     180
ggtgccctcg aacagctcgc cgtcgaccga cttccacgcc gtgcgcatgt ccaggaggtt     240
cacgaagaag tcgttggtca gcttgccggg ccgggtggtg aagacgccgt gcgaggagcc     300
gtcgtagttg cgcgcccagga cgcgcagccc gcccacgagc accgtcagct ccggcggcgt     360
cagcgtcagc agctgcgccc ggtcgacgag gaggtgctcc gtcggcacgc cgcgccgtgcc    420
gcggccgtag ttgcggaagc cgtcggcata cggctcgagg tgcgcgaacg acgccacgtc     480
ggtctgctcc tgcgacgcgt cggtgcggcc gggccggaag gcaccggca cgccggccgc      540
ctgctcgagc gccgccacgc cgcccagcac gatcaggtcc gccagcgaca ccttcttgcc     600
gccgccgcc gacgcgttga acttggcctg cacgccctcg agcgcctgca gcacctcggc      660
cagctgcggc gggttgttga ccttccagtc cttctgcggc gccagccgga tgcgcgcgcc    720
gttggcgccg ccgcgcttgt cgctgccgcg gaacgtcgac gccgacgccc acgccaccga    780
gatgagcttg gccggggcca cgcccgtggc caggatgtcg cgcttcagcg cggcgatgtc    840
gctgtcgtcg acgagcgggt ggtcgaccgg cggcacgtag tcctcccaga ggagcacctc    900
ggacgggatc tccgggccga ccagcgcga acgcgggccc atgtcgcggt gcagcagctt      960
gaaccaggcg cgcgcgaacg cgtcggcgaa ctggtctggg tgctcgaggt agtggcgcgc  1020
gatcttctcg tacaccgggt cgaagcgcag cgccaggtcc gtcgtgagca tgcgcggccg    1080
gtgcttcttg ctcgggtcgt acgcgtccgg aatgaaagcg tcggcgttct tggccaccca    1140
ctggttggcg ccggcgggc tcttggtgag ctcccactcg aacttgaaga ggtactccaa     1200
gaagttggtg ctccaccggg tcggcgtctt ggtccagatg acctcgagcc cactggtgat  1260
ggtatcaggg cccttgccgg agccgtgctt gttggcccag ccgagaccct gctgctccag  1320
gccggccccc tcgggctcct tgccgacgtt gtccgagggg gccgcgccgt gcgtcttgcc  1380
```

```
gaacgtgtgg ccgccggcga tcagggccac cgtctcctcg tcgttcatgg ccatgcggct    1440
gaaggtcgtg cggatgtccc gcgcggccgc cacggggtcg gggatgccgt ccggacccctc   1500 ggggttgacg tagatcaggc ccatgtgggc ggccgccaag ggcgactcga gatcgcgcga    1560
gtggatgtcc ttgttgacct tcttggactc gtcgccgccc gtgacgccgt cgccggcgat    1620
gcccgcctgg ccgtccgagt agcggacatc gttgccgagc acgtcgtcct cgccgcccca    1680
gtaggtcgac tcgtcagcct cccacgtgtc cggacggccg ccggcaaagc cgaacgtctt    1740
gaggcccatg gactcgaggg cgacgttgcc agtcagcagc agcaggtcgg cccacgagat    1800
cttgtcgccg tacttctgct tgatgggcca cagcaggcgg cgggccttgt cgagactgac    1860
gttgtcgggc cagctgttga gtggcgcaaa ccgctgctgg ccctggccgc cgccgccgcg    1920
gccgtcgaag acgcggtagg tgccggcgct gtgccaggcc atgcggatga acagaccgcc    1980
gtagtggccg aagtcggccg gccaccagtc ctgcgagtcg gtcatgagcg cccgcaggtc    2040
ctgcttcagc gcgtcatagt caagcgactt gaaggcggcc ctatagtcga agtccttgta    2100
cgggctcgac gccggctggt gctggcggag gatgtggagc ggcagccggt tcggccacca    2160
gtcggtgttt cgagtaccgc cgccggcggc gttggcgaac ctgttcgggc actcacccat    2220
cttctcgctt gttcaatctt ccgtcgctgt ggctgctggg tgcttgtgcg tgtgtgtgtg    2280
tgtgtgtgtg agtcggagtg tgtatgtgtc tgtttgtttg tgtgggttgc agaacgtaa     2340 gctgcgaaac aaaccgccac tg                                             2362
```

<210> SEQ ID NO 20
<211> LENGTH: 740
<212> TYPE: PRT
<213> ORGANISM: Thielavia terrestris

<400> SEQUENCE: 20

Met Arg Ala Lys His Glu Ile Gly Pro Arg Gly Arg Pro Leu Leu Gly
1               5                   10                  15

Ala Arg Arg Thr Val Gly Ala Leu Glu Gln Leu Ala Val Asp Arg Leu
            20                  25                  30

Pro Arg Arg Ala His Val Gln Glu Val His Glu Val Val Gly Gln
        35                  40                  45

Leu Ala Gly Pro Gly Gly Glu Asp Ala Val Arg Gly Ala Val Val Val
    50                  55                  60

Gly Ala Gln Asp Ala Gln Pro Ala His Glu His Arg Gln Leu Arg Arg
65                  70                  75                  80

Arg Gln Arg Gln Gln Leu Arg Pro Val Asp Glu Val Leu Arg Arg
                85                  90                  95

His Ala Arg Arg Ala Ala Ala Val Val Ala Glu Ala Val Gly Ile Arg
            100                 105                 110

Leu Glu Val Arg Glu Arg Arg His Val Gly Leu Leu Leu Arg Arg Val
        115                 120                 125

Gly Ala Ala Gly Pro Glu Gly His Arg His Ala Gly Arg Leu Leu Glu
    130                 135                 140

Arg Arg His Ala Ala Gln His Asp Gln Val Arg Gln Arg His Leu Leu
145                 150                 155                 160

Ala Ala Arg Arg Arg Val Glu Leu Gly Leu His Ala Leu Glu Arg
                165                 170                 175

Leu Gln His Leu Gly Gln Leu Arg Arg Val Val Asp Leu Pro Val Leu
            180                 185                 190

Leu Arg Arg Gln Pro Asp Ala Arg Ala Val Gly Ala Ala Ala Leu Val

-continued

```
           195                 200                 205
Ala Ala Ala Glu Arg Arg Arg Arg Pro Arg His Arg Asp Glu Leu
210                 215                 220

Gly Arg Gly His Ala Arg Gly Gln Asp Val Ala Leu Gln Arg Gly Asp
225                 230                 235                 240

Val Ala Val Val Asp Glu Arg Val Val Asp Arg Arg His Val Val Leu
                245                 250                 255

Pro Glu Glu His Leu Gly Arg Asp Leu Arg Ala Glu Pro Ala Arg Thr
            260                 265                 270

Arg Ala His Val Ala Val Gln Gln Leu Glu Pro Gly Ala Arg Glu Arg
        275                 280                 285

Val Gly Glu Leu Val Trp Val Leu Glu Val Val Ala Arg Asp Leu Leu
    290                 295                 300

Val His Arg Val Glu Ala Gln Arg Gln Val Arg Arg Glu His Ala Arg
305                 310                 315                 320

Pro Val Leu Leu Ala Arg Val Val Arg Val Arg Asn Glu Ser Val Gly
                325                 330                 335

Val Leu Gly His Pro Leu Val Gly Ala Gly Ala Leu Gly Glu Leu
            340                 345                 350

Pro Leu Glu Leu Glu Val Leu Gln Glu Val Gly Ala Pro Pro Gly
        355                 360                 365

Arg Arg Leu Gly Pro Asp Asp Leu Glu Pro Thr Gly Asp Gly Ile Arg
370                 375                 380

Ala Leu Ala Gly Ala Val Leu Val Gly Pro Ala Glu Thr Leu Leu Leu
385                 390                 395                 400

Gln Ala Gly Pro Leu Gly Leu Ala Asp Val Val Arg Gly Arg
                405                 410                 415

Ala Val Arg Leu Ala Glu Arg Val Ala Ala Gly Asp Gln Gly His Arg
            420                 425                 430

Leu Leu Val Val His Gly His Ala Ala Glu Gly Arg Ala Asp Val Pro
        435                 440                 445

Arg Gly Arg His Gly Val Gly Asp Ala Val Arg Thr Leu Gly Val Asp
    450                 455                 460

Val Asp Gln Ala His Val Gly Gly Arg Gln Gly Arg Leu Glu Ile Ala
465                 470                 475                 480

Arg Val Asp Val Leu Val Asp Leu Leu Gly Leu Val Ala Ala Arg Asp
                485                 490                 495

Ala Val Ala Gly Asp Ala Arg Leu Ala Val Arg Val Ala Asp Ile Val
            500                 505                 510

Ala Glu Pro Arg Arg Leu Ala Ala Pro Val Gly Arg Leu Val Ser Leu
        515                 520                 525

Pro Arg Val Arg Thr Ala Ala Gly Lys Ala Glu Arg Leu Glu Ala His
    530                 535                 540

Gly Leu Glu Gly Asp Val Ala Ser Gln Gln Gln Val Gly Pro Arg
545                 550                 555                 560

Asp Leu Val Ala Val Leu Leu Leu Asp Gly Pro Gln Gln Ala Gly
                565                 570                 575

Leu Val Glu Thr Asp Val Gly Pro Ala Val Glu Trp Arg Lys Pro
            580                 585                 590

Leu Leu Ala Leu Ala Ala Ala Ala Val Glu Asp Ala Val Gly
        595                 600                 605

Ala Gly Ala Val Pro Gly His Ala Asp Glu Gln Thr Ala Val Val Ala
    610                 615                 620
```

```
Glu Val Gly Arg Pro Pro Val Leu Arg Val Gly His Glu Arg Pro Gln
625                 630                 635                 640

Val Leu Leu Gln Arg Val Ile Val Lys Arg Leu Glu Gly Gly Pro Ile
            645                 650                 655

Val Glu Val Leu Val Arg Ala Arg Arg Leu Val Leu Ala Glu Asp
        660                 665                 670

Val Glu Arg Gln Pro Val Arg Pro Val Gly Val Ser Ser Thr Ala
        675                 680                 685

Ala Gly Gly Val Gly Glu Pro Val Arg Ala Leu Thr His Leu Leu Ala
    690                 695                 700

Cys Ser Ile Phe Arg Arg Cys Gly Cys Trp Val Leu Val Arg Val Cys
705                 710                 715                 720

Val Cys Val Cys Glu Ser Glu Cys Val Cys Val Cys Leu Phe Val Trp
            725                 730                 735

Val Ala Arg Thr
            740

<210> SEQ ID NO 21
<211> LENGTH: 1449
<212> TYPE: DNA
<213> ORGANISM: Bacillus thermoglucosidasius

<400> SEQUENCE: 21
atgagttcaa ataaactgac aactagctgg ggagcacctg ttggcgataa ccaaaactcg      60
ataacggccg gcaatcctgg cccgacatta atccaagacg tacatcttat cgaaaaatta    120
gcacacttca atagagaacg tgtcccagaa cgtgttgtcc atgcgaaagg cgctggtgcg    180
cacggctatt tcgaagtaac aaacgatatg tcgaaataca caaaagcgaa agtgtttaac    240
ggtgttggca acgcacgcc tgtattcgtc cgcttctcta ctgtcgccgg tgaattggga    300
tctgcggata cagtccgcga cccgcgcggt tttgccgtca aattttatac cgaagaagga    360
aactatgaca tcgttggcaa caacacaccg attttcttca ttcgtgatgc gattaaattc    420
tcggatttta tccatacaca aaaacgcgac ccgcgcaccc atttgattta tccgacagca    480
atgtgggatt tcttgtcttt atctccggaa tctttgcacc aagtcactta tttattcggg    540
gatcgcggca tcccattgac ataccgccat atgaacggat acggaagcca tacattcaaa    600
tgggtgaatg aaaaggcga agcggtatgg gtaaatacc actttaaaac aaaccaaggc    660
gtgaaaaaca tggatccgga actagcggtt aaaatcgccg agaaaatcc ggattaccat    720 acggaagatt tatataacgc catcgaaaaa ggcgactatc catcttggac attatatgtg    780
caaattatgc cgttagaaga cgcaaaaaca taccgtttca atccatttga tgtcacaaaa    840
gtttggtcac ataaagatta tccgttaatt gaagtcggcc gtatggtatt aaaccgcaat    900
ccagaaaatt attttgccga agtcgaacaa gcgacattct ctcctggaaa ccttgttcct    960
ggcgttgaac atcgccgga taaatcttg caagcccgtt tgttcgctta tgcggatgcg   1020
caccgttacc gcgtcggcgt gaaccataac ttgcttccga tcaaccgccc gcgcgtggaa   1080
gtaaacaatt atcaacgtga cggcttcatg cgctttgaca taatggcgg cggttcggtc   1140 aactacgaac caaacagctt cggcggaccg acagaagtgc cagaacataa aacgacccca   1200
ttcccggtat ccggcgtggc agaaagcgtg ccatatgacg acgatgatca ttatacgcaa   1260
gcaggcgact tataccgtct catgagcgaa gaagaaaaag cgcgccttgt gaaaaacatt   1320
gtcgaatcat tgaaacaagt aacaaaagaa gaaattaaac ttcgccaaat ccgccacttc   1380
```

```
tacaaagcag accctgacta cggccgccgc gttgccgaag gtcttggatt gccgattaaa       1440
aaagattct                                                              1449
```

<210> SEQ ID NO 22
<211> LENGTH: 483
<212> TYPE: PRT
<213> ORGANISM: Bacillus thermoglucosidasius

<400> SEQUENCE: 22

```
Met Ser Ser Asn Lys Leu Thr Thr Ser Trp Gly Ala Pro Val Gly Asp
1               5                   10                  15

Asn Gln Asn Ser Ile Thr Ala Gly Asn Pro Gly Pro Thr Leu Ile Gln
            20                  25                  30

Asp Val His Leu Ile Glu Lys Leu Ala His Phe Asn Arg Glu Arg Val
        35                  40                  45

Pro Glu Arg Val Val His Ala Lys Gly Ala Gly Ala His Gly Tyr Phe
    50                  55                  60

Glu Val Thr Asn Asp Met Ser Tyr Thr Lys Ala Lys Val Phe Asn
65                  70                  75                  80

Gly Val Gly Lys Arg Thr Pro Val Phe Val Arg Phe Ser Thr Val Ala
                85                  90                  95

Gly Glu Leu Gly Ser Ala Asp Thr Val Arg Asp Pro Arg Gly Phe Ala
            100                 105                 110

Val Lys Phe Tyr Thr Glu Glu Gly Lys Tyr Asp Ile Val Gly Asn Asn
        115                 120                 125

Thr Pro Ile Phe Phe Ile Arg Asp Ala Ile Lys Phe Ser Asp Phe Ile
130                 135                 140

His Thr Gln Lys Arg Asp Pro Arg Thr His Leu Ile Tyr Pro Thr Ala
145                 150                 155                 160

Met Trp Asp Phe Leu Ser Leu Ser Pro Glu Ser Leu His Gln Val Thr
                165                 170                 175

Tyr Leu Phe Gly Asp Arg Gly Ile Pro Leu Thr Tyr Arg His Met Asn
            180                 185                 190

Gly Tyr Gly Ser His Thr Phe Lys Trp Val Asn Glu Lys Gly Glu Ala
        195                 200                 205

Val Trp Val Lys Tyr His Phe Lys Thr Asn Gln Gly Val Lys Asn Met
    210                 215                 220

Asp Pro Glu Leu Ala Val Lys Ile Ala Gly Glu Asn Pro Asp Tyr His
225                 230                 235                 240

Thr Glu Asp Leu Tyr Asn Ala Ile Glu Lys Gly Asp Tyr Pro Ser Trp
                245                 250                 255

Thr Leu Tyr Val Gln Ile Met Pro Leu Glu Asp Ala Lys Thr Tyr Arg
            260                 265                 270

Phe Asn Pro Glu Asp Val Thr Lys Val Trp Ser His Lys Asp Tyr Pro
        275                 280                 285

Leu Ile Glu Val Gly Arg Met Val Leu Asn Arg Asn Pro Glu Asn Tyr
    290                 295                 300

Phe Ala Glu Val Glu Gln Ala Thr Phe Ser Pro Gly Asn Leu Val Pro
305                 310                 315                 320

Gly Val Glu Pro Ser Pro Asp Lys Ile Leu Gln Ala Arg Leu Phe Ala
                325                 330                 335

Tyr Ala Asp Ala His Arg Tyr Arg Val Gly Val Asn His Asn Leu Leu
            340                 345                 350

Pro Ile Asn Arg Pro Arg Val Glu Val Asn Asn Tyr Gln Arg Asp Gly
```

```
                 355                 360                 365
Phe Met Arg Phe Asp Asn Asn Gly Gly Gly Ser Val Asn Tyr Glu Pro
    370                 375                 380

Asn Ser Phe Gly Gly Pro Thr Glu Val Pro Glu His Lys Thr Thr Pro
385                 390                 395                 400

Phe Pro Val Ser Gly Val Ala Glu Ser Val Pro Tyr Asp Asp Asp Asp
                405                 410                 415

His Tyr Thr Gln Ala Gly Asp Leu Tyr Arg Leu Met Ser Glu Glu Glu
            420                 425                 430

Lys Ala Arg Leu Val Lys Asn Ile Val Glu Ser Leu Lys Gln Val Thr
        435                 440                 445

Lys Glu Glu Ile Lys Leu Arg Gln Ile Arg His Phe Tyr Lys Ala Asp
    450                 455                 460

Pro Asp Tyr Gly Arg Arg Val Ala Glu Gly Leu Gly Leu Pro Ile Lys
465                 470                 475                 480

Lys Asp Ser
```

<210> SEQ ID NO 23
<211> LENGTH: 3210
<212> TYPE: DNA
<213> ORGANISM: Aspergillus oryzae

<400> SEQUENCE: 23

```
cccccccagaa gggtccaaag gcccagtccc ttcccctttcg gtcttaacaa aagacggacc      60
tttacgacgg aatttcgaag taaggggcca gggcattcgt tccctggaaa gaagagcgag     120
cttctggtgg agactctcga taagcccgat aagaaaagca ctcgactctc cttcccgatg     180
acgaagttca taaacaagga acataatcag taagaagata ttctgaccaa taccaatgga     240
ttcgaataat cattactcat catcttgtat tcttcataag agaaacagt atcagaaaaa      300
gaaaaaaaac cagttcgatg tcaacgtgac gttcatcaac cctgcgacgt cattttgacg     360
tgcgggaccc atcacaacat ccattcagaa gttttttcatt actggaaaag ctataagaag     420
ctgaagaata tacatttct tgttctcatg caagtaatga ccgtttcatg aacatagcct      480
cgatcccacc ttaatctatc tccgactatc ttatcgtccc cataatcatc atatccatca     540
gaccccaatc atggccaata ttgtggctgg gggcctccac aaggttcaag aagcagtgca     600
gggcgctgct tccaaggata agaagctagt tgacctagca cccgacaccc ataatgtaca     660
gtccagcaag gagccactga ccaccgacca tggtgtgcgt atcagcgata cggaccactg     720
gctgaaggag gtgaatgaca accacaccgg tcctatgatg cttgaggacc agattgcacg     780
agagaaggta tgattccccg aatcggtatg ggtcagaacc atagattgaa cgaatcgcaa     840
cccagattca tcgtttcgat catgagcgca ttcccgagag agtcgtccat gcgcgtggca     900
ccgctgcatt cggaaacttc aagctccatg agagcgctga agatgtatcc tacgctggta     960
tcttgacgga tacctcaagg aacactccgg ttttccttcg tttctccacg gtccagggca    1020
gtaaaggaag tgccgacacc gtccgtgacg ttcgtgggtt tgccgtgaaa ttctacaccg    1080
acgaaggaaa tgggatctg gttggaaaca acatccccgt ttctcttatc caagatgcga    1140
ttaagttccc ggattttggt acgtacctcc tcccaactat gagtccaaaa ctctagagct    1200
aacgagtgta gtccatgctg ttaagcccga gccgcacaac gaggtaccac aggcccaaac    1260
tgctcacaac aacttctggg actttgtcta tcttcacccg gaagccaccc atatgttcat    1320
gtgggccatg tctgatcggg ccattcctcg gtcataccgt atgatgcagg gttttcggtgt   1380
```

-continued

| | |
|---|---|
| caacacattc agtctcatca acaaggaagg aaagcgccat tttgtcaagt tccatttcat | 1440 |
| cccccacctg ggagtgcact ctttggtgtg ggacgaggct ctgaaactgg ctggccagga | 1500 |
| ccccgatttc catcgcaagg atctcatgga ggccattgat aacggcgcat acccgaaatg | 1560 |
| ggacttcgcc atccaggtca tccctgagga gaaacaggat gacttcgaat ttgacatttt | 1620 |
| cgacgcgacg aagatctggc ccgaggagct cgtgcctctg cgcgtgatcg gcgaactgga | 1680 |
| actgaaccgc aacgtcgacg agttcttccc tcaaaccgag caagtcgcct tctgcaccag | 1740 |
| ccacatcgtc cccggcattg acttcagtga cgacccgctt ctccagggcc gtaacttctc | 1800 |
| ctacttcgac actcagatca gtcgactggg catcaactgg gaagaaatcc ccatcaaccg | 1860 |
| ccccgtctgc cccgttctga accacaaccg agacggcgcc aaacgccacc gcatcgccca | 1920 |
| gggcactgtc actacttggt cgaaccggtc cgaggccgga ccacccgcac cagtagaaca | 1980 |
| tggtggcttc gcgtcctacc ctgcgaaact gaacggtatc aagaagcgcg gcctgagccc | 2040 |
| caagttccgc gagcaccaca accaggctca actcttctac aactctctct ccgagcacga | 2100 |
| gaaggtccac gtcaagaagg ccttcggctt cgaactggac cactgcgacg accccatcgt | 2160 |
| ctacgagcgc ctcgccggcc accgtctcgc cgagatcgat ctcactctcg cccaggaagt | 2220 |
| cgccgagctc gtcggcgccc cgatcccaga caaggcactt cgcccgaacc atggaaagcg | 2280 |
| cagcaagcat ctttcgcaga ccgagttccc gggtaagcag ccgacgatcg ccagtcgccg | 2340 |
| aatcgccatc attatcggcg acggatacga ccccgtcgct ttcaatggcc tcaagggcgc | 2400 |
| catcacggcg gttggagcct accgttcgt cattggcacc aagcggtcac ctatctacgc | 2460 |
| cgacggtgag gacaaatcat cttccaaggg cgtgatcgcc gaccaccagt atgacggaca | 2520 |
| gcgttcgacg atgtttgacg ctaccttcat ccctggcggt ccgcacgtcg aaagcctcaa | 2580 |
| ggccaatggc cagatccggt actggatcat tgagacattc ggtcatctca aggctctggg | 2640 |
| cgccactggt gaagcggcgg ctttcatcaa ggaagccctg gctccgcgc ttgatgtgaa | 2700 |
| ggtcgctacg tctgataacc cccagccggt tgagtggtat ggtgttgtca cggctggaaa | 2760 |
| gatccacaaa cctgagagct tcaaggaggg tatccagatt gtcaaggatg cgaaggattt | 2820 |
| cattagcacc ttcttctacc agatcagtca gcatcggaac tacaagcgtg aactggatgg | 2880 |
| cctcgcctcg acagttgcat tctaaatgct ttcgtgattg gttgaggaca tggaggcttg | 2940 |
| tgttaacgca aaagtggcat tttagttaat gtcatccttg taatgaatta tgtctctaac | 3000 |
| tgtggatggc cagaatgtac gctaatatga atcatgaaaa tactctattc taattgtgaa | 3060 |
| tgtgaaagtg aaacggcgtc gaaaggtagt tatcaatgtt atcctgaggt atctaatata | 3120 |
| caacatcttt gatattgtag gaaagaaacg taagaaagga tcgtacatag tggggtatca | 3180 |
| taatctggta cagcgtccaa ggctcggctt | 3210 |

<210> SEQ ID NO 24
<211> LENGTH: 747
<212> TYPE: PRT
<213> ORGANISM: Aspergillus oryzae

<400> SEQUENCE: 24

Met Ala Asn Ile Val Ala Gly Gly Leu His Lys Val Gln Glu Ala Val
1               5                   10                  15

Gln Gly Ala Ala Ser Lys Asp Lys Lys Leu Val Asp Leu Ala Pro Asp
            20                  25                  30

Thr His Asn Val Gln Ser Ser Lys Glu Pro Leu Thr Thr Asp His Gly
        35                  40                  45

-continued

Val Arg Ile Ser Asp Thr Asp His Trp Leu Lys Glu Val Asn Asp Asn
 50                  55                  60

His Thr Gly Pro Met Met Leu Glu Asp Gln Ile Ala Arg Glu Lys Ile
 65                  70                  75                  80

His Arg Phe Asp His Glu Arg Ile Pro Glu Arg Val Val His Ala Arg
                     85                  90                  95

Gly Thr Ala Ala Phe Gly Asn Phe Lys Leu His Glu Ser Ala Glu Asp
                100                 105                 110

Val Ser Tyr Ala Gly Ile Leu Thr Asp Thr Ser Arg Asn Thr Pro Val
            115                 120                 125

Phe Leu Arg Phe Ser Thr Val Gln Gly Ser Lys Gly Ser Ala Asp Thr
130                 135                 140

Val Arg Asp Val Arg Gly Phe Ala Val Lys Phe Tyr Thr Asp Glu Gly
145                 150                 155                 160

Asn Trp Asp Leu Val Gly Asn Asn Ile Pro Val Phe Phe Ile Gln Asp
                165                 170                 175

Ala Ile Lys Phe Pro Asp Phe Val His Ala Val Lys Pro Glu Pro His
                180                 185                 190

Asn Glu Val Pro Gln Ala Gln Thr Ala His Asn Asn Phe Trp Asp Phe
            195                 200                 205

Val Tyr Leu His Pro Glu Ala Thr His Met Phe Met Trp Ala Met Ser
210                 215                 220

Asp Arg Ala Ile Pro Arg Ser Tyr Arg Met Met Gln Gly Phe Gly Val
225                 230                 235                 240

Asn Thr Phe Ser Leu Ile Asn Lys Glu Gly Lys Arg His Phe Val Lys
                245                 250                 255

Phe His Phe Ile Pro His Leu Gly Val His Ser Leu Val Trp Asp Glu
                260                 265                 270

Ala Leu Lys Leu Ala Gly Gln Asp Pro Asp Phe His Arg Lys Asp Leu
            275                 280                 285

Met Glu Ala Ile Asp Asn Gly Ala Tyr Pro Lys Trp Asp Phe Ala Ile
290                 295                 300

Gln Val Ile Pro Glu Glu Lys Gln Asp Phe Glu Phe Asp Ile Phe
305                 310                 315                 320

Asp Ala Thr Lys Ile Trp Pro Glu Glu Leu Val Pro Leu Arg Val Ile
                325                 330                 335

Gly Glu Leu Glu Leu Asn Arg Asn Val Asp Glu Phe Phe Pro Gln Thr
                340                 345                 350

Glu Gln Val Ala Phe Cys Thr Ser His Ile Val Pro Gly Ile Asp Phe
            355                 360                 365

Ser Asp Asp Pro Leu Leu Gln Gly Arg Asn Phe Ser Tyr Phe Asp Thr
370                 375                 380

Gln Ile Ser Arg Leu Gly Ile Asn Trp Glu Glu Ile Pro Ile Asn Arg
385                 390                 395                 400

Pro Val Cys Pro Val Leu Asn His Asn Arg Asp Gly Ala Lys Arg His
                405                 410                 415

Arg Ile Ala Gln Gly Thr Val Thr Thr Trp Ser Asn Arg Ser Glu Ala
                420                 425                 430

Gly Pro Pro Ala Pro Val Glu His Gly Phe Ala Ser Tyr Pro Ala
            435                 440                 445

Lys Leu Asn Gly Ile Lys Lys Arg Gly Leu Ser Pro Lys Phe Arg Glu
450                 455                 460

His His Asn Gln Ala Gln Leu Phe Tyr Asn Ser Leu Ser Glu His Glu

-continued

```
             465                 470                 475                 480
        Lys Val His Val Lys Ala Phe Gly Phe Glu Leu Asp His Cys Asp
                        485                 490                 495
        Asp Pro Ile Val Tyr Glu Arg Leu Ala Gly His Arg Leu Ala Glu Ile
                    500                 505                 510
        Asp Leu Thr Leu Ala Gln Glu Val Ala Glu Leu Val Gly Ala Pro Ile
                    515                 520                 525
        Pro Asp Lys Ala Leu Arg Pro Asn His Gly Lys Arg Ser Lys His Leu
                    530                 535                 540
        Ser Gln Thr Glu Phe Pro Gly Lys Gln Pro Thr Ile Ala Ser Arg Arg
        545                 550                 555                 560
        Ile Ala Ile Ile Ile Gly Asp Gly Tyr Asp Pro Val Ala Phe Asn Gly
                        565                 570                 575
        Leu Lys Gly Ala Ile Thr Ala Val Gly Ala Leu Pro Phe Val Ile Gly
                    580                 585                 590
        Thr Lys Arg Ser Pro Ile Tyr Ala Asp Gly Glu Asp Lys Ser Ser Ser
                    595                 600                 605
        Lys Gly Val Ile Ala Asp His Gln Tyr Asp Gly Gln Arg Ser Thr Met
        610                 615                 620
        Phe Asp Ala Thr Phe Ile Pro Gly Gly Pro His Val Glu Ser Leu Lys
        625                 630                 635                 640
        Ala Asn Gly Gln Ile Arg Tyr Trp Ile Ile Glu Thr Phe Gly His Leu
                        645                 650                 655
        Lys Ala Leu Gly Ala Thr Gly Glu Ala Ala Phe Ile Lys Glu Ala
                    660                 665                 670
        Leu Gly Ser Ala Leu Asp Val Lys Val Ala Thr Ser Asp Asn Pro Gln
                    675                 680                 685
        Pro Val Glu Trp Tyr Gly Val Val Thr Ala Gly Lys Ile His Lys Pro
                    690                 695                 700
        Glu Ser Phe Lys Glu Gly Ile Gln Ile Val Lys Asp Ala Lys Asp Phe
        705                 710                 715                 720
        Ile Ser Thr Phe Phe Tyr Gln Ile Ser Gln His Arg Asn Tyr Lys Arg
                        725                 730                 735
        Glu Leu Asp Gly Leu Ala Ser Thr Val Ala Phe
                    740                 745

<210> SEQ ID NO 25
<211> LENGTH: 2502
<212> TYPE: DNA
<213> ORGANISM: Thermoascus aurantiacus

<400> SEQUENCE: 25
atgcgcgcaa ttggacttct gccaggcatc atcggcattg ctggtgctgc ctgtccttac    60
atgacaggcg agctgccgcg ctccttcgcc gagaaccctc atgctatcaa ccgtcgtgct   120
gagggtggtg gtggtgccgc tgccgagacg agaagttcc tgtctcagtt ctacctgaac   180
gacaacgaca ccttcatgac caccgatgtt ggcggtccaa ttgaggatca gaacagtctc   240
agcgctggtg acagaggtcc taccctgctg gaggacttca tcctccgtca aaagatccag   300
cgctttgacc atgagcgggt aggttgatct ttactttcgg ccttcttcga gcggggtgat   360
attaaaacag gtaataggtg cccgagcgtg ctgtccatgc ccgaggagcg ggagcgcatg   420
gcgtgttcac atcctacgca gactggtcca acatcactgc cgcttccttc ctgtctgctg   480
caggaaagga gacacctgtc tttgtccggt tctccactgt agcaggaagc agaggaagcg   540
```

| | | |
|---|---|---|
| cagacacggc gcgtgacgtg cacggtttcg cgacgaggtt ctacacggat gaagggaact | 600 | |
| tcggtaggca actatcatgc tctctttaaa tgttctcgat ctgacagcca gcagacattg | 660 | |
| tcggcaacaa catccctgtc ttcttcattc aagatgcgat ccagttcccc gacctgatcc | 720 | |
| atgctgtcaa gcccagcccg aacaacgaga tccctcaggc cgcaaccgcc catgactctg | 780 | |
| cctgggactt tttcagccag cagccgagct ctttgcatac tctgttctgg gctatggccg | 840 | |
| gtcatggcat tcctcgttcc tacaggaaca tggatggctt cggcatccac accttccgct | 900 | |
| tgtgacgga cgatggagct tccaagctcg tcaagttcca ctggacgtcg ctgcagggca | 960 | |
| aggcgagcct tgtgtgggaa gaggcacagg ccgtggctgg aaagaacgcg gactatcacc | 1020 | |
| gccaggactt gtgggacgca atcgaggctg gaaggtaccc tgagtgggag gtaggctctc | 1080 | |
| cctgctatgt atggatgtgc cagaagctta ataatggcct agctcggcgt gcaaatcatg | 1140 | |
| gatgaggaag accagctgcg ctttggcttc gatctgttgg acccgaccaa gatcgttccc | 1200 | |
| gaggaatacg tgcccatcac gaagctcgga agatgcagc tcaaccgcaa cccgctgaac | 1260 | |
| tacttcgccg agactgaaca gatcatggtc agttcgccac cgtgttcggt tgctcgttgc | 1320 | |
| tgaagtgcta acttgcaaca gttccaaccg ggtcacgttg tccgtggcat tgatttcacc | 1380 | |
| gaggaccctc tgctccaggg acgtctcttc tcttacctcg acacccagct caaccgccac | 1440 | |
| ggaggtccga acttcgagca gatccccatc aaccggccac gcactccaat tcacaacaac | 1500 | |
| aaccgtgacg gagccggtat gctagcccat gtattccttt ctttatgcat ttttatatga | 1560 | |
| tgcgttctaa cggcaacagc gcaaatgtac atccccctga caaggcggc gtacaccccc | 1620 | |
| aacactctga caacggctc ccccaagcag gccaaccaga cggtcggaaa gggcttcttc | 1680 | |
| acgactccag gccggacggc aagcggcagg cttgtgcgcg ccgtcagctc aaccttcgcc | 1740 | |
| gacgtctggt cgcagcctcg tctgttctac aactccctcg tgccggcgga gcagcagttc | 1800 | |
| ctgatcaacg cgatccgctt tgagacggcc cacatcacga gcgacgtcgt gaagaacaac | 1860 | |
| gtcatcatcc agctgaaccg cgtgagcaac aacctcgcca agagtcgc ccgggccatc | 1920 | |
| ggtgtcgcgg agcccgagcc agacccaacc ttgtaccaca acaacaagac cgccaacgtc | 1980 | |
| ggggtgttcg gcaagccgct cgccagactc gacggcctgc aggtcggggt cctcgccacc | 2040 | |
| gtcaacaagc ccgactcgat caagcaggcc gccagcctga aggccagctt cgcggcggac | 2100 | |
| aacgtcgacg tcaaggtcgt cgcggagcgc ctcgccgacg cgtcgacga gacctactcg | 2160 | |
| gccgccgacg cggtcaactt cgacgccatc ctggtcgcca acggcgctga gggcctcttc | 2220 | |
| gcgcgcgaca gcttcaccgc caggccggcc aactcgacca ccgcgacgct ctaccccgcg | 2280 | |
| ggccgcccgc tccagatcct ggtcgacggg ttccgctacg gcaagccggt cggggcgctc | 2340 | |
| ggcagcggcg ccaaggcgct cgacgcagcg gagatttcga cgacccgggc cggcgtgtac | 2400 | |
| gtcgccaact cgacgaccga cagcttcatc aatggcgtca gggacggtct gcggacgttc | 2460 | |
| aagttcctgg accggttcgc gattgacgag gatgctgagt ga | 2502 | |

<210> SEQ ID NO 26
<211> LENGTH: 740
<212> TYPE: PRT
<213> ORGANISM: Thermoascus aurantiacus

<400> SEQUENCE: 26

Met Arg Ala Ile Gly Leu Leu Pro Gly Ile Ile Gly Ile Ala Gly Ala
1               5                   10                  15

Ala Cys Pro Tyr Met Thr Gly Glu Leu Pro Arg Ser Phe Ala Glu Asn
            20                  25                  30

```
Pro His Ala Ile Asn Arg Arg Ala Glu Gly Gly Gly Ala Ala Ala
    35                  40                  45

Glu Thr Glu Lys Phe Leu Ser Gln Phe Tyr Leu Asn Asp Asn Asp Thr
 50                  55                  60

Phe Met Thr Thr Asp Val Gly Gly Pro Ile Glu Asp Gln Asn Ser Leu
 65                  70                  75                  80

Ser Ala Gly Asp Arg Gly Pro Thr Leu Leu Glu Asp Phe Ile Leu Arg
                 85                  90                  95

Gln Lys Ile Gln Arg Phe Asp His Glu Arg Val Pro Glu Arg Ala Val
            100                 105                 110

His Ala Arg Gly Ala Gly Ala His Gly Val Phe Thr Ser Tyr Ala Asp
            115                 120                 125

Trp Ser Asn Ile Thr Ala Ala Ser Phe Leu Ser Ala Ala Gly Lys Glu
        130                 135                 140

Thr Pro Val Phe Val Arg Phe Ser Thr Val Ala Gly Ser Arg Gly Ser
145                 150                 155                 160

Ala Asp Thr Ala Arg Asp Val His Gly Phe Ala Thr Arg Phe Tyr Thr
                165                 170                 175

Asp Glu Gly Asn Phe Asp Ile Val Gly Asn Asn Ile Pro Val Phe Phe
            180                 185                 190

Ile Gln Asp Ala Ile Gln Phe Pro Asp Leu Ile His Ala Val Lys Pro
        195                 200                 205

Ser Pro Asn Asn Glu Ile Pro Gln Ala Ala Thr Ala His Asp Ser Ala
    210                 215                 220

Trp Asp Phe Phe Ser Gln Pro Ser Ser Leu His Thr Leu Phe Trp
225                 230                 235                 240

Ala Met Ala Gly His Gly Ile Pro Arg Ser Tyr Arg Asn Met Asp Gly
                245                 250                 255

Phe Gly Ile His Thr Phe Arg Phe Val Thr Asp Asp Gly Ala Ser Lys
            260                 265                 270

Leu Val Lys Phe His Trp Thr Ser Leu Gln Gly Lys Ala Ser Leu Val
        275                 280                 285

Trp Glu Glu Ala Gln Ala Val Ala Gly Lys Asn Ala Asp Tyr His Arg
    290                 295                 300

Gln Asp Leu Trp Asp Ala Ile Glu Ala Gly Arg Tyr Pro Glu Trp Glu
305                 310                 315                 320

Leu Gly Val Gln Ile Met Asp Glu Glu Asp Gln Leu Arg Phe Gly Phe
                325                 330                 335

Asp Leu Leu Asp Pro Thr Lys Ile Val Pro Glu Glu Tyr Val Pro Ile
            340                 345                 350

Thr Lys Leu Gly Lys Met Gln Leu Asn Arg Asn Pro Leu Asn Tyr Phe
        355                 360                 365

Ala Glu Thr Glu Gln Ile Met Phe Gln Pro Gly His Val Val Arg Gly
    370                 375                 380

Ile Asp Phe Thr Glu Asp Pro Leu Leu Gln Gly Arg Leu Phe Ser Tyr
385                 390                 395                 400

Leu Asp Thr Gln Leu Asn Arg His Gly Gly Pro Asn Phe Glu Gln Ile
                405                 410                 415

Pro Ile Asn Arg Pro Arg Thr Pro Ile His Asn Asn Asn Arg Asp Gly
            420                 425                 430

Ala Ala Gln Met Tyr Ile Pro Leu Asn Lys Ala Ala Tyr Thr Pro Asn
        435                 440                 445
```

```
Thr Leu Asn Asn Gly Ser Pro Lys Gln Ala Asn Gln Thr Val Gly Lys
        450                 455                 460
Gly Phe Phe Thr Thr Pro Gly Arg Thr Ala Ser Gly Arg Leu Val Arg
465                 470                 475                 480
Ala Val Ser Ser Thr Phe Ala Asp Val Trp Ser Gln Pro Arg Leu Phe
                485                 490                 495
Tyr Asn Ser Leu Val Pro Ala Glu Gln Gln Phe Leu Ile Asn Ala Ile
            500                 505                 510
Arg Phe Glu Thr Ala His Ile Thr Ser Asp Val Val Lys Asn Asn Val
        515                 520                 525
Ile Ile Gln Leu Asn Arg Val Ser Asn Asn Leu Ala Lys Arg Val Ala
530                 535                 540
Arg Ala Ile Gly Val Ala Glu Pro Glu Pro Asp Pro Thr Leu Tyr His
545                 550                 555                 560
Asn Asn Lys Thr Ala Asn Val Gly Val Phe Gly Lys Pro Leu Ala Arg
                565                 570                 575
Leu Asp Gly Leu Gln Val Gly Val Leu Ala Thr Val Asn Lys Pro Asp
            580                 585                 590
Ser Ile Lys Gln Ala Ala Ser Leu Lys Ala Ser Phe Ala Ala Asp Asn
        595                 600                 605
Val Asp Val Lys Val Val Ala Glu Arg Leu Ala Asp Gly Val Asp Glu
    610                 615                 620
Thr Tyr Ser Ala Ala Asp Ala Val Asn Phe Asp Ala Ile Leu Val Ala
625                 630                 635                 640
Asn Gly Ala Glu Gly Leu Phe Ala Arg Asp Ser Phe Thr Ala Arg Pro
                645                 650                 655
Ala Asn Ser Thr Thr Ala Thr Leu Tyr Pro Ala Gly Arg Pro Leu Gln
            660                 665                 670
Ile Leu Val Asp Gly Phe Arg Tyr Gly Lys Pro Val Gly Ala Leu Gly
        675                 680                 685
Ser Gly Ala Lys Ala Leu Asp Ala Ala Glu Ile Ser Thr Thr Arg Ala
    690                 695                 700
Gly Val Tyr Val Ala Asn Ser Thr Thr Asp Ser Phe Ile Asn Gly Val
705                 710                 715                 720
Arg Asp Gly Leu Arg Thr Phe Lys Phe Leu Asp Arg Phe Ala Ile Asp
                725                 730                 735
Glu Asp Ala Glu
            740

<210> SEQ ID NO 27
<211> LENGTH: 1452
<212> TYPE: DNA
<213> ORGANISM: Bacillus thermoglucosidasius

<400> SEQUENCE: 27
atgagttcaa ataaactgac aactagctgg ggcgctccgg ttggagataa tcaaaactca    60
atgactgccg gttctcgcgg accaacttta attcaagatg tacatttact cgaaaaattg   120
gcccatttca accgagaacg tgttcctgaa cgtgttgttc acgccaaagg agcaggcgca   180
cacggatatt ttgaagtgac aaacgacgta acaaaataca cgaaagccgc tttcctttct   240
gaagtcggca aacgcacacc gttgttcatc cgtttctcaa cagttgccgg tgaacttggc   300
tctgctgaca cagttcgcga cccgcgcgga tttgctgtta aattttatac tgaagaagga   360
aactacgaca tcgtcggcaa caatacgcct gtattcttta tccgcgatgc gattaagttc   420
```

```
cctgatttca tccatacaca aaaaagagat ccaaaaacac acctgaaaaa ccctacggct    480
gtatgggatt tctggtcact ttcaccagag tcattgcacc aagtgacaat cctgatgtct    540
gaccgcggaa ttcctgcgac acttcgccac atgcacggct tcggaagcca tacattcaaa    600
tggacaaatg ccgaacccga aggcgtatgg attaaatatc actttaaaac agaacaaggc    660
gtgaaaaacc ttgatgtcaa tacggcagca aaaattgccg gtgaaaaccc tgattaccat    720
acagaagacc ttttcaacgc aatcgaaaac ggtgattatc ctgcatggaa actatatgtg    780
caaatcatgc ctttagaaga tgcaaatacg taccgtttcg atccgtttga tgtcacaaaa    840
gtttggtctc aaaaagacta cccgttaatc gaggtcggac gcatggttct agacagaaat    900
ccggaaaact actttgcaga ggtagaacaa gcgacatttt cacctggaac cctcgtgcct    960
ggtattgatg tttcaccgga taaaatgctt caaggtcgac ttttgctta tcatgatgca    1020
caccgctacc gtgtcggtgc aaaccatcaa gcgctgccaa tcaaccgcgc acgcaacaaa    1080
gtaaacaatt atcagcgtga tgggcaaatg cgttttgatg ataacggcgg cggatctgtg    1140
tattacgagc taacagcttc cggcggtcca aaagagtcac ctgaggataa gcaagcagca    1200
tatccggtac aaggtatcgc tgacagcgta agctacgatc actacgatca ctacactcaa    1260
gccggcgatc tgtatcgttt aatgagtgaa gatgaacgta cccgccttgt tgaaaatatc    1320
gttaatgcca tgaagccggt agaaaaagaa gaaatcaagc tgcgccaaat cgagcacttc    1380
tacaaagcgg atcctgaata cggaaaacgc gtggcagaag ccttggatt gccgattaaa    1440
aaagattctt aa                                                        1452

<210> SEQ ID NO 28
<211> LENGTH: 483
<212> TYPE: PRT
<213> ORGANISM: Bacillus thermoglucosidasius

<400> SEQUENCE: 28

Met Ser Ser Asn Lys Leu Thr Thr Ser Trp Gly Ala Pro Val Gly Asp
1               5                   10                  15

Asn Gln Asn Ser Met Thr Ala Gly Ser Arg Gly Pro Thr Leu Ile Gln
            20                  25                  30

Asp Val His Leu Leu Glu Lys Leu Ala His Phe Asn Arg Glu Arg Val
        35                  40                  45

Pro Glu Arg Val Val His Ala Lys Gly Ala Gly Ala His Gly Tyr Phe
    50                  55                  60

Glu Val Thr Asn Asp Val Thr Lys Tyr Thr Lys Ala Ala Phe Leu Ser
65                  70                  75                  80

Glu Val Gly Lys Arg Thr Pro Leu Phe Ile Arg Phe Ser Thr Val Ala
                85                  90                  95

Gly Glu Leu Gly Ser Ala Asp Thr Val Arg Asp Pro Arg Gly Phe Ala
            100                 105                 110

Val Lys Phe Tyr Thr Glu Glu Gly Asn Tyr Asp Ile Val Gly Asn Asn
        115                 120                 125

Thr Pro Val Phe Phe Ile Arg Asp Ala Ile Lys Phe Pro Asp Phe Ile
    130                 135                 140

His Thr Gln Lys Arg Asp Pro Lys Thr His Leu Lys Asn Pro Thr Ala
145                 150                 155                 160

Val Trp Asp Phe Trp Ser Leu Ser Pro Glu Ser Leu His Gln Val Thr
                165                 170                 175

Ile Leu Met Ser Asp Arg Gly Ile Pro Ala Thr Leu Arg His Met His
            180                 185                 190
```

```
Gly Phe Gly Ser His Thr Phe Lys Trp Thr Asn Ala Glu Pro Glu Gly
            195                 200                 205

Val Trp Ile Lys Tyr His Phe Lys Thr Glu Gln Gly Val Lys Asn Leu
    210                 215                 220

Asp Val Asn Thr Ala Ala Lys Ile Ala Gly Glu Asn Pro Asp Tyr His
225                 230                 235                 240

Thr Glu Asp Leu Phe Asn Ala Ile Glu Asn Gly Asp Tyr Pro Ala Trp
                245                 250                 255

Lys Leu Tyr Val Gln Ile Met Pro Leu Glu Asp Ala Asn Thr Tyr Arg
            260                 265                 270

Phe Asp Pro Phe Asp Val Thr Lys Val Trp Ser Gln Lys Asp Tyr Pro
            275                 280                 285

Leu Ile Glu Val Gly Arg Met Val Leu Asp Arg Asn Pro Glu Asn Tyr
    290                 295                 300

Phe Ala Glu Val Glu Gln Ala Thr Phe Ser Pro Gly Thr Leu Val Pro
305                 310                 315                 320

Gly Ile Asp Val Ser Pro Asp Lys Met Leu Gln Gly Arg Leu Phe Ala
                325                 330                 335

Tyr His Asp Ala His Arg Tyr Arg Val Gly Ala Asn His Gln Ala Leu
            340                 345                 350

Pro Ile Asn Arg Ala Arg Asn Lys Val Asn Asn Tyr Gln Arg Asp Gly
            355                 360                 365

Gln Met Arg Phe Asp Asp Asn Gly Gly Ser Val Tyr Tyr Glu Pro
    370                 375                 380

Asn Ser Phe Gly Gly Pro Lys Glu Ser Pro Glu Asp Lys Gln Ala Ala
385                 390                 395                 400

Tyr Pro Val Gln Gly Ile Ala Asp Ser Val Ser Tyr Asp His Tyr Asp
                405                 410                 415

His Tyr Thr Gln Ala Gly Asp Leu Tyr Arg Leu Met Ser Glu Asp Glu
            420                 425                 430

Arg Thr Arg Leu Val Glu Asn Ile Val Asn Ala Met Lys Pro Val Glu
            435                 440                 445

Lys Glu Glu Ile Lys Leu Arg Gln Ile Glu His Phe Tyr Lys Ala Asp
            450                 455                 460

Pro Glu Tyr Gly Lys Arg Val Ala Glu Gly Leu Gly Leu Pro Ile Lys
465                 470                 475                 480

Lys Asp Ser

<210> SEQ ID NO 29
<211> LENGTH: 1449
<212> TYPE: DNA
<213> ORGANISM: Bacillus thermoglucosidasius

<400> SEQUENCE: 29
atgagttcaa ataaactgac aactagctgg ggagcacctg ttggcgataa ccaaaactcg    60
ataacggccg gcaatcctgg cccgacatta atccaagacg tacatcttat cgaaaaatta   120
gcacacttca atagagaacg tgtcccagaa cgtgttgtcc atgcgaaagg cgctggtgcg   180
cacggctatt tcgaagtaac aaacgatatg tcgaaataca caaagcgaa agtgtttaac   240 ggtgttggca acgcacgcc tgtattcgtc cgcttctcta ctgtcgccgg tgaattggga   300
tctgcggata cagtccgcga cccgcgcggt tttgccgtca aatttttatac cgaagaagga   360 aactatgaca tcgttggcaa caacacaccg attttcttca ttcgtgatgc gattaaattc   420
```

```
tcggatttta tccatacaca aaaacgcgac ccgcgcaccc atttgattta tccgacagca      480
atgtgggatt tcttgtcttt atctccggaa tctttgcacc aagtcactta tttattcggg      540
gatcgcggca tcccattgac ataccgccat atgaacggat acggaagcca tacattcaaa      600
tgggtgaatg aaaaaggcga agcggtatgg gtaaaatacc actttaaaac aaaccaaggc      660
gtgaaaaaca tggatccgga actagcggtt aaaatcgccg agaaaatcc ggattaccat       720 acggaagatt tatataacgc catcgaaaaa ggcgactatc catcttggac attatatgtg      780
caaattatgc cgttagaaga cgcaaaaaca taccgtttca atccatttga tgtcacaaaa      840
gtttggtcac ataaagatta tccgttaatt gaagtcggcc gtatggtatt aaaccgcaat      900
ccagaaaatt attttgccga agtcgaacaa gcgacattct ctcctggaaa ccttgttcct      960
ggcgttgaac catcgccgga taaaatcttg caagcccgtt tgttcgctta tgcggatgcg     1020
caccgttacc gcgtcggcgt gaaccataac ttgcttccga tcaaccgccc gcgcgtggaa     1080
gtaaacaatt atcaacgtga cggcttcatg cgctttgaca ataatggcgg cggttcggtc     1140
aactacgaac caaacagctt cggcggaccg acagaagtgc agaacataa aacgaccca        1200 ttcccggtat ccggcgtggc agaaagcgtg ccatgacg acgatgatca ttatacgcaa        1260
gcaggcgact tataccgtct catgagcgaa gaagaaaaag cgcgccttgt gaaaaacatt     1320
gtcgaatcat tgaaacaagt aacaaaagaa gaattaaac ttcgccaaat ccgccacttc      1380
tacaaagcag accctgacta cggccgccgc gttgccgaag tcttggatt gccgattaaa     1440 aaagattct                                                            1449

<210> SEQ ID NO 30
<211> LENGTH: 483
<212> TYPE: PRT
<213> ORGANISM: Bacillus thermoglucosidasius

<400> SEQUENCE: 30

Met Ser Ser Asn Lys Leu Thr Thr Ser Trp Gly Ala Pro Val Gly Asp
1               5                   10                  15

Asn Gln Asn Ser Ile Thr Ala Gly Asn Pro Gly Pro Thr Leu Ile Gln
            20                  25                  30

Asp Val His Leu Ile Glu Lys Leu Ala His Phe Asn Arg Glu Arg Val
        35                  40                  45

Pro Glu Arg Val Val His Ala Lys Gly Ala Gly Ala His Gly Tyr Phe
    50                  55                  60

Glu Val Thr Asn Asp Met Ser Lys Tyr Thr Lys Ala Lys Val Phe Asn
65                  70                  75                  80

Gly Val Gly Lys Arg Thr Pro Val Phe Val Arg Phe Ser Thr Val Ala
                85                  90                  95

Gly Glu Leu Gly Ser Ala Asp Thr Val Arg Asp Pro Arg Gly Phe Ala
            100                 105                 110

Val Lys Phe Tyr Thr Glu Glu Gly Asn Tyr Asp Ile Val Gly Asn Asn
        115                 120                 125

Thr Pro Ile Phe Phe Ile Arg Asp Ala Ile Lys Phe Ser Asp Phe Ile
    130                 135                 140

His Thr Gln Lys Arg Asp Pro Arg Thr His Leu Ile Tyr Pro Thr Ala
145                 150                 155                 160

Met Trp Asp Phe Leu Ser Leu Ser Pro Glu Ser Leu His Gln Val Thr
                165                 170                 175

Tyr Leu Phe Gly Asp Arg Gly Ile Pro Leu Thr Tyr Arg His Met Asn
            180                 185                 190
```

```
Gly Tyr Gly Ser His Thr Phe Lys Trp Val Asn Glu Lys Gly Glu Ala
            195                 200                 205

Val Trp Val Lys Tyr His Phe Lys Thr Asn Gln Gly Val Lys Asn Met
    210                 215                 220

Asp Pro Glu Leu Ala Val Lys Ile Ala Gly Glu Asn Pro Asp Tyr His
225                 230                 235                 240

Thr Glu Asp Leu Tyr Asn Ala Ile Glu Lys Gly Asp Tyr Pro Ser Trp
                245                 250                 255

Thr Leu Tyr Val Gln Ile Met Pro Leu Glu Asp Ala Lys Thr Tyr Arg
            260                 265                 270

Phe Asn Pro Phe Asp Val Thr Lys Val Trp Ser His Lys Asp Tyr Pro
        275                 280                 285

Leu Ile Glu Val Gly Arg Met Val Leu Asn Arg Asn Pro Glu Asn Tyr
    290                 295                 300

Phe Ala Glu Val Glu Gln Ala Thr Phe Ser Pro Gly Asn Leu Val Pro
305                 310                 315                 320

Gly Val Glu Pro Ser Pro Asp Lys Ile Leu Gln Ala Arg Leu Phe Ala
                325                 330                 335

Tyr Ala Asp Ala His Arg Tyr Arg Val Gly Val Asn His Asn Leu Leu
            340                 345                 350

Pro Ile Asn Arg Pro Arg Val Glu Val Asn Asn Tyr Gln Arg Asp Gly
        355                 360                 365

Phe Met Arg Phe Asp Asn Asn Gly Gly Gly Ser Val Asn Tyr Glu Pro
    370                 375                 380

Asn Ser Phe Gly Gly Pro Thr Glu Val Pro Glu His Lys Thr Thr Pro
385                 390                 395                 400

Phe Pro Val Ser Gly Val Ala Glu Ser Val Pro Tyr Asp Asp Asp
                405                 410                 415

His Tyr Thr Gln Ala Gly Asp Leu Tyr Arg Leu Met Ser Glu Glu Glu
            420                 425                 430

Lys Ala Arg Leu Val Lys Asn Ile Val Glu Ser Leu Lys Gln Val Thr
        435                 440                 445

Lys Glu Glu Ile Lys Leu Arg Gln Ile Arg His Phe Tyr Lys Ala Asp
    450                 455                 460

Pro Asp Tyr Gly Arg Arg Val Ala Glu Gly Leu Gly Leu Pro Ile Lys
465                 470                 475                 480

Lys Asp Ser

<210> SEQ ID NO 31
<211> LENGTH: 2262
<212> TYPE: DNA
<213> ORGANISM: Alcaligenes aquamarinus

<400> SEQUENCE: 31
atgaataacg catccgctga cgatctacac agtagcttgc agcaaagatg cagagcattt      60
gttcccttgg tatcgccaag gcatagagca ataagggaga gagctatgag cggtaaatgt     120
cctgtcatgc acggtggtaa cacctcgacc ggtacttcca acaaagattg gtggccggaa     180
gggttgaacc tggatatttt gcatcagcaa gatcgcaaat cagacccgat ggatccggat     240
ttcaactacc gtgaagaagt acgcaagctc gatttcgacg cgctgaagaa agatgtccac     300
gcgttgatga ccgatagcca agagtggtgg cccgctgact gggggcacta cggcggtttg     360
atgatccgta tggcttggca ctccgctggc acctaccgta ttgctgatgg ccgtgggggc     420
```

-continued

```
ggtggtaccg aagccagcg ctttgcaccg ctcaactcct ggccggacaa cgtcagcctg    480
gataaagcgc gccgtctgct gtggccgatc aagaagaagt acggcaacaa atcagctgg    540
gcagacctga tgattctggc tggcaccgtg gcttatgagt ccatgggctt acctgcttac    600
ggcttctctt tcggccgcgt cgatatttgg gaacccgaaa aagatatcta ctggggtgac    660
gaaaaagagt ggctggcacc ttctgacgaa cgctacggcg acgtgaacaa gccagagacc    720
atggaaaacc cgctggcggc tgtccaaatg ggtctgatct atgtgaaccc ggaaggtgtt    780
aacggccacc ctgatccgct gagaaccgca cagcaggtac ttgaaacctt cgcccgtatg    840
gcgatgaacg acgaaaaaac cgcagccctc acagctggcg ccacaccgt cggtaattgt    900
cacggtaatg gcaatgcctc tgcgttagcc cctgacccaa agcctctga cgttgaaaac    960
cagggcttag gttggggcaa ccccaacatg cagggcaagg caagcaacgc cgtgacctcg   1020
ggtatcgaag gtgcttggac caccaacccc acgaaattcg atatgggcta tttcgacctg   1080
ctgttcggct acaattggga actgaaaaag agtcctgccg gtgccccacca ttgggaaccg   1140
attgacatca aaaggaaaa caagccggtt gacgccagcg accctctat cgccacaac    1200
ccgatcatga ccgatgcgga tatggcgata aggtaaatc cgacctatcg cgctatctgc   1260
gaaaaattca tggccgatcc tgagtacttc aagaaaactt cgcgaaggc gtggttcaag   1320
ctgacgcacc gtgacctggg cccgaaatca cgttacatcg gcccggaagt gccggcagaa   1380
gacctgattt ggcaagaccc gattccggca ggtaacaccg actactgcga agaagtggtc   1440
aagcagaaaa ttgcacaaag tggcctgagc attagtgaga tggtctccac cgcttgggac   1500
agtgcccgta cttatcgcgg ttccgatatg cgcggcggtg ctaacggtgc cgcattcgc    1560
ttggccccac agaacgagtg gcagggcaac gagccggagc gcctggcgaa agtgctgagc   1620
gtctacgagc agatctctgc cgacaccggc gctagcatcg cggacgtgat cgttctggcc   1680
ggtagcgtag gcatcgagaa agccgcgaaa gcagcaggtt acgatgtgcg cgttcccttc   1740
ctgaaaggcc gtggcgatgc gaccgccgag atgaccgacg cagactcctt cgcaccgctg   1800
gagccgctgg ccgatggctt ccgcaactgg cagaagaaag agtatgtggt gaagccggaa   1860
gagatgctgc tggatcgtgc gcagctgatg ggcttaaccg gcccggaaat gaccgtgctg   1920
ctgggcggta tgcgcgtact gggcaccaac tatggtggca ccaaacacgg cgtattcacc   1980
gattgtgaag ccagttgac caacgacttt tttgtgaacc tgaccgatat ggggaacagc   2040
tggaagccgg taggtagcaa cgcctacgaa atccgcgacc gcaagaccgg tgccgtgaag   2100
tggaccgcct cgcgggtgga tctggtatttt ggttccaact cgctactgcg ctcttacgca   2160
gaagtgtacg cccaggacga taacggcgag aagttcgtca gagacttcgt cgccgcctgg   2220
accaaagtga tgaacgccga ccgtttcgac gtcgcgtcgt aa                      2262
```

<210> SEQ ID NO 32
<211> LENGTH: 753
<212> TYPE: PRT
<213> ORGANISM: Alcaligenes aquamarinus

<400> SEQUENCE: 32

Met Asn Asn Ala Ser Ala Asp Asp Leu His Ser Ser Leu Gln Gln Arg
1               5                   10                  15

Cys Arg Ala Phe Val Pro Leu Val Ser Pro Arg His Arg Ala Ile Arg
            20                  25                  30

Glu Arg Ala Met Ser Gly Lys Cys Pro Val Met His Gly Gly Asn Thr
        35                  40                  45

```
Ser Thr Gly Thr Ser Asn Lys Asp Trp Trp Pro Glu Gly Leu Asn Leu
     50                  55                  60

Asp Ile Leu His Gln Gln Asp Arg Lys Ser Asp Pro Met Asp Pro Asp
 65              70                  75                      80

Phe Asn Tyr Arg Glu Glu Val Arg Lys Leu Asp Phe Asp Ala Leu Lys
             85                  90                  95

Lys Asp Val His Ala Leu Met Thr Asp Ser Gln Glu Trp Trp Pro Ala
            100                 105                 110

Asp Trp Gly His Tyr Gly Gly Leu Met Ile Arg Met Ala Trp His Ser
            115                 120                 125

Ala Gly Thr Tyr Arg Ile Ala Asp Gly Arg Gly Gly Gly Thr Gly
    130                 135                 140

Ser Gln Arg Phe Ala Pro Leu Asn Ser Trp Pro Asp Asn Val Ser Leu
145                 150                 155                 160

Asp Lys Ala Arg Arg Leu Leu Trp Pro Ile Lys Lys Tyr Gly Asn
                165                 170                 175

Lys Ile Ser Trp Ala Asp Leu Met Ile Leu Ala Gly Thr Val Ala Tyr
            180                 185                 190

Glu Ser Met Gly Leu Pro Ala Tyr Gly Phe Ser Phe Gly Arg Val Asp
        195                 200                 205

Ile Trp Glu Pro Glu Lys Asp Ile Tyr Trp Gly Asp Glu Lys Glu Trp
        210                 215                 220

Leu Ala Pro Ser Asp Glu Arg Tyr Gly Asp Val Asn Lys Pro Glu Thr
225                 230                 235                 240

Met Glu Asn Pro Leu Ala Ala Val Gln Met Gly Leu Ile Tyr Val Asn
                245                 250                 255

Pro Glu Gly Val Asn Gly His Pro Asp Pro Leu Arg Thr Ala Gln Gln
                260                 265                 270

Val Leu Glu Thr Phe Ala Arg Met Ala Met Asn Asp Glu Lys Thr Ala
        275                 280                 285

Ala Leu Thr Ala Gly Gly His Thr Val Gly Asn Cys His Gly Asn Gly
        290                 295                 300

Asn Ala Ser Ala Leu Ala Pro Asp Pro Lys Ala Ser Asp Val Glu Asn
305                 310                 315                 320

Gln Gly Leu Gly Trp Gly Asn Pro Asn Met Gln Gly Lys Ala Ser Asn
                325                 330                 335

Ala Val Thr Ser Gly Ile Glu Gly Ala Trp Thr Thr Asn Pro Thr Lys
            340                 345                 350

Phe Asp Met Gly Tyr Phe Asp Leu Leu Phe Gly Tyr Asn Trp Glu Leu
        355                 360                 365

Lys Lys Ser Pro Ala Gly Ala His His Trp Glu Pro Ile Asp Ile Lys
    370                 375                 380

Lys Glu Asn Lys Pro Val Asp Ala Ser Asp Pro Ser Ile Arg His Asn
385                 390                 395                 400

Pro Ile Met Thr Asp Ala Asp Met Ala Ile Lys Val Asn Pro Thr Tyr
                405                 410                 415

Arg Ala Ile Cys Glu Lys Phe Met Ala Asp Pro Glu Tyr Phe Lys Lys
            420                 425                 430

Thr Phe Ala Lys Ala Trp Phe Lys Leu Thr His Arg Asp Leu Gly Pro
            435                 440                 445

Lys Ser Arg Tyr Ile Gly Pro Glu Val Pro Ala Glu Asp Leu Ile Trp
450                 455                 460

Gln Asp Pro Ile Pro Ala Gly Asn Thr Asp Tyr Cys Glu Glu Val Val
```

```
Lys Gln Lys Ile Ala Gln Ser Gly Leu Ser Ile Ser Glu Met Val Ser
            485                 490                 495

Thr Ala Trp Asp Ser Ala Arg Thr Tyr Arg Gly Ser Asp Met Arg Gly
            500                 505                 510

Gly Ala Asn Gly Ala Arg Ile Arg Leu Ala Pro Gln Asn Glu Trp Gln
            515                 520                 525

Gly Asn Glu Pro Glu Arg Leu Ala Lys Val Leu Ser Val Tyr Glu Gln
            530                 535                 540

Ile Ser Ala Asp Thr Gly Ala Ser Ile Ala Asp Val Ile Val Leu Ala
545                 550                 555                 560

Gly Ser Val Gly Ile Glu Lys Ala Ala Lys Ala Ala Gly Tyr Asp Val
                565                 570                 575

Arg Val Pro Phe Leu Lys Gly Arg Gly Asp Ala Thr Ala Glu Met Thr
            580                 585                 590

Asp Ala Asp Ser Phe Ala Pro Leu Glu Pro Leu Ala Asp Gly Phe Arg
            595                 600                 605

Asn Trp Gln Lys Lys Glu Tyr Val Val Lys Pro Glu Glu Met Leu Leu
            610                 615                 620

Asp Arg Ala Gln Leu Met Gly Leu Thr Gly Pro Glu Met Thr Val Leu
625                 630                 635                 640

Leu Gly Gly Met Arg Val Leu Gly Thr Asn Tyr Gly Gly Thr Lys His
                645                 650                 655

Gly Val Phe Thr Asp Cys Glu Gly Gln Leu Thr Asn Asp Phe Phe Val
            660                 665                 670

Asn Leu Thr Asp Met Gly Asn Ser Trp Lys Pro Val Gly Ser Asn Ala
            675                 680                 685

Tyr Glu Ile Arg Asp Arg Lys Thr Gly Ala Val Lys Trp Thr Ala Ser
            690                 695                 700

Arg Val Asp Leu Val Phe Gly Ser Asn Ser Leu Leu Arg Ser Tyr Ala
705                 710                 715                 720

Glu Val Tyr Ala Gln Asp Asp Asn Gly Glu Lys Phe Val Arg Asp Phe
                725                 730                 735

Val Ala Ala Trp Thr Lys Val Met Asn Ala Asp Arg Phe Asp Val Ala
            740                 745                 750

Ser

<210> SEQ ID NO 33
<211> LENGTH: 2238
<212> TYPE: DNA
<213> ORGANISM: Microscilla furvescens

<400> SEQUENCE: 33
atggaaaatc acaaacactc aggatcttct acgtataaca caaacactgg cggaaaatgc      60
ccttttaccg gaggttcgct taagcaaagt gcaggtggcg gcaccaaaaa cagggattgg     120
tggcccaaca tgctcaacct cggcatctta cgccaacatt catcgctatc ggacccaaac     180
gacccggatt ttgactatgc cgaagagttt aagaagctag atctggcagc ggttaaaaag     240
gacctggcag cgctaatgac agattcacag gactggtggc agcagattat cggtcattat     300 ggcccttct ttatacgcat ggcgtggcac agcgccggca cctaccgtat cggtgatggc     360
cgtggtggcg gtggctccgg ctcacagcgc ttcgcgcctc tcaatagctg gccagacaat     420
gccaatctgg ataaagcacg cttgcttctt tggcccatca acaaaaaata cggtcgaaaa     480
```

```
atctcctggg cggatctaat gatactcaca ggaaacgtag ctctggaaac tatgggcttt      540 aaaactttg gttttgcagg tggcagagca gatgtatggg agcctgaaga agatgtatac      600
tggggagcag aaaccgaatg gctgggagac aagcgctatg aaggtgaccg agagctcgaa     660
aatcccctgg gagccgtaca atgggactc atctatgtaa accccgaagg acccaacggc      720
aagccagacc ctatcgctgc tgcgcgtgat attcgtgaga cttttggccg aatggcaatg     780
aatgacgaag aaaccgtggc tctcatagcg ggtggacaca ccttcggaaa acccatggt      840 gctgccgatg cggagaaata tgtgggccga gagcctgccg ccgcaggtat tgaagaaatg     900
agcctggggt ggaaaaacac ctacggcacc ggacacggtg cggataccat caccagtgga     960
ctagaaggcg cctggaccaa gacccctact caatggagca ataacttttt tgaaaacctc    1020
tttggttacg agtgggagct taccaaaagt ccagctggag cttatcagtg aaaccaaaa    1080 gacggtgccg ggctggcac ataccggat gcacatgatc ccagcaagtc gcacgctcca     1140
tttatgctca ctacggacct ggcgctgcgc atggacctg attacgaaaa aatttctcga    1200
cggtactatg aaaaccctga tgagtttgca gatgctttcg cgaaagcatg gtacaaactg    1260
acacacagag atatgggacc aaaggtgcgc tacctgggac cagaagtgcc tcaggaagac    1320
ctcatctggc aagaccctat accagatgta agccatcctc ttgtagacga aaacgatatt    1380
gaaggcctaa aagccaaaat cctggaatcg ggactgacgg taagcgagct ggtaagcacg    1440
gcatgggctt ctgcatctac ttttagaaac tctgacaagc gcggcggtgc aacggtgca     1500 cgtatacgac tggccccaca aaagactgg gaagtaaaca accctcagca acttgccagg    1560
gtactcaaaa cactgaaagg tatccaggag gactttaacc aggcgcaatc agataacaaa    1620
gcagtatcgt tggccgacct gattgtgctg gccggctgtg cgggtgtaga aaagctgca    1680 aaagatgctg gccatgaggt gcaggtgcct ttcaacccgg acagagcgga tgccaccgct    1740
gagcaaaccg atgtggaagc tttcgaagca ctagagccag cggctgacgg ctttagaaac    1800
tacattaaac cggagcataa agtatccgct gaggaaatgc tcgtagaccg ggcgcagctt    1860
ctgtcgcttt cggcaccaga aatgactgct ttggtaggcg gtatgcgtgt actgggcacc    1920
aactacgacg gttcgcagca tggagtgttt acaaataagc cgggtcagct atccaatgac    1980
ttctttgtaa acctgctaga cctcaacact aaatggcgag ccagcgatga atcagacaaa    2040 gttttttgaag gcagagactt caaaactggc gaagtaaagt ggagtggcac ccgggtagac    2100
ctgatcttcg gatccaattc cgagctaaga gccctcgcag aagtgtacgg ctgtgcagat    2160
tctgaagaaa agtttgttaa agattttgtg aaggcctggg ccaaagtaat ggacctggac    2220
cggtttgatc tgaaataa                                                    2238
```

<210> SEQ ID NO 34
<211> LENGTH: 745
<212> TYPE: PRT
<213> ORGANISM: Microscilla furvescens

<400> SEQUENCE: 34

```
Met Glu Asn His Lys His Ser Gly Ser Ser Thr Tyr Asn Thr Asn Thr
1               5                   10                  15

Gly Gly Lys Cys Pro Phe Thr Gly Gly Ser Leu Lys Gln Ser Ala Gly
            20                  25                  30

Gly Gly Thr Lys Asn Arg Asp Trp Trp Pro Asn Met Leu Asn Leu Gly
        35                  40                  45

Ile Leu Arg Gln His Ser Ser Leu Ser Asp Pro Asn Asp Pro Asp Phe
    50                  55                  60
```

```
Asp Tyr Ala Glu Glu Phe Lys Lys Leu Asp Leu Ala Ala Val Lys Lys
 65                  70                  75                  80

Asp Leu Ala Ala Leu Met Thr Asp Ser Gln Asp Trp Trp Pro Ala Asp
                 85                  90                  95

Tyr Gly His Tyr Gly Pro Phe Phe Ile Arg Met Ala Trp His Ser Ala
            100                 105                 110

Gly Thr Tyr Arg Ile Gly Asp Gly Arg Gly Gly Gly Ser Gly Gly Ser
        115                 120                 125

Gln Arg Phe Ala Pro Leu Asn Ser Trp Pro Asp Asn Ala Asn Leu Asp
    130                 135                 140

Lys Ala Arg Leu Leu Leu Trp Pro Ile Lys Gln Lys Tyr Gly Arg Lys
145                 150                 155                 160

Ile Ser Trp Ala Asp Leu Met Ile Leu Thr Gly Asn Val Ala Leu Glu
                165                 170                 175

Thr Met Gly Phe Lys Thr Phe Gly Phe Ala Gly Gly Arg Ala Asp Val
            180                 185                 190

Trp Glu Pro Glu Glu Asp Val Tyr Trp Gly Ala Glu Thr Glu Trp Leu
        195                 200                 205

Gly Asp Lys Arg Tyr Glu Gly Asp Arg Glu Leu Glu Asn Pro Leu Gly
210                 215                 220

Ala Val Gln Met Gly Leu Ile Tyr Val Asn Pro Glu Gly Pro Asn Gly
225                 230                 235                 240

Lys Pro Asp Pro Ile Ala Ala Arg Asp Ile Arg Glu Thr Phe Gly
                245                 250                 255

Arg Met Ala Met Asn Asp Glu Glu Thr Val Ala Leu Ile Ala Gly Gly
                260                 265                 270

His Thr Phe Gly Lys Thr His Gly Ala Ala Asp Ala Glu Lys Tyr Val
            275                 280                 285

Gly Arg Glu Pro Ala Ala Ala Gly Ile Glu Glu Met Ser Leu Gly Trp
290                 295                 300

Lys Asn Thr Tyr Gly Thr Gly His Gly Ala Asp Thr Ile Thr Ser Gly
305                 310                 315                 320

Leu Glu Gly Ala Trp Thr Lys Thr Pro Thr Gln Trp Ser Asn Asn Phe
                325                 330                 335

Phe Glu Asn Leu Phe Gly Tyr Glu Trp Glu Leu Thr Lys Ser Pro Ala
            340                 345                 350

Gly Ala Tyr Gln Trp Lys Pro Lys Asp Gly Ala Gly Ala Gly Thr Ile
        355                 360                 365

Pro Asp Ala His Asp Pro Ser Lys Ser His Ala Pro Phe Met Leu Thr
    370                 375                 380

Thr Asp Leu Ala Leu Arg Met Asp Pro Asp Tyr Glu Lys Ile Ser Arg
385                 390                 395                 400

Arg Tyr Tyr Glu Asn Pro Asp Glu Phe Ala Asp Ala Phe Ala Lys Ala
                405                 410                 415

Trp Tyr Lys Leu Thr His Arg Asp Met Gly Pro Lys Val Arg Tyr Leu
            420                 425                 430

Gly Pro Glu Val Pro Gln Glu Asp Leu Ile Trp Gln Asp Pro Ile Pro
        435                 440                 445

Asp Val Ser His Pro Leu Val Asp Glu Asn Asp Ile Glu Gly Leu Lys
    450                 455                 460

Ala Lys Ile Leu Glu Ser Gly Leu Thr Val Ser Glu Leu Val Ser Thr
465                 470                 475                 480
```

```
Ala Trp Ala Ser Ala Ser Thr Phe Arg Asn Ser Asp Lys Arg Gly Gly
                485                 490                 495

Ala Asn Gly Ala Arg Ile Arg Leu Ala Pro Gln Lys Asp Trp Glu Val
            500                 505                 510

Asn Asn Pro Gln Gln Leu Ala Arg Val Leu Lys Thr Leu Glu Gly Ile
        515                 520                 525

Gln Glu Asp Phe Asn Gln Ala Gln Ser Asp Asn Lys Ala Val Ser Leu
    530                 535                 540

Ala Asp Leu Ile Val Leu Ala Gly Cys Ala Gly Val Glu Lys Ala Ala
545                 550                 555                 560

Lys Asp Ala Gly His Glu Val Gln Val Pro Phe Asn Pro Gly Arg Ala
                565                 570                 575

Asp Ala Thr Ala Glu Gln Thr Asp Val Glu Ala Phe Glu Ala Leu Glu
            580                 585                 590

Pro Ala Ala Asp Gly Phe Arg Asn Tyr Ile Lys Pro Glu His Lys Val
        595                 600                 605

Ser Ala Glu Glu Met Leu Val Asp Arg Ala Gln Leu Leu Ser Leu Ser
    610                 615                 620

Ala Pro Glu Met Thr Ala Leu Val Gly Gly Met Arg Val Leu Gly Thr
625                 630                 635                 640

Asn Tyr Asp Gly Ser Gln His Gly Val Phe Thr Asn Lys Pro Gly Gln
                645                 650                 655

Leu Ser Asn Asp Phe Phe Val Asn Leu Leu Asp Leu Asn Thr Lys Trp
            660                 665                 670

Arg Ala Ser Asp Glu Ser Asp Lys Val Phe Glu Gly Arg Asp Phe Lys
        675                 680                 685

Thr Gly Glu Val Lys Trp Ser Gly Thr Arg Val Asp Leu Ile Phe Gly
    690                 695                 700

Ser Asn Ser Glu Leu Arg Ala Leu Ala Glu Val Tyr Gly Cys Ala Asp
705                 710                 715                 720

Ser Glu Glu Lys Phe Val Lys Asp Phe Val Lys Ala Trp Ala Lys Val
                725                 730                 735

Met Asp Leu Asp Arg Phe Asp Leu Lys
            740                 745

<210> SEQ ID NO 35
<211> LENGTH: 3108
<212> TYPE: DNA
<213> ORGANISM: Aspergillus niger

<400> SEQUENCE: 35
cttgtcaccg agtgcccgtt tgtcacttgt tgtggtgatc ttgagcacat cgcgttcctc      60
tcgtctcatc acatcgagtg atcaacattg catgaccota gtggagcccc ttcgtctccc     120
aacaggaggg tccggattac caagtcccga caccgtttgg ctgtaattcg actcaaattc     180
tggattcgta gcttaactaa gacgcgtggt ctgttaaccg gcctcgccat ggatgccgat     240
ataaggaccc taggggactc cccctggtg actctcgtcg aagatcgca gcactctgaa       300 ttctcctagt cttcgtttac tccgccatgc gtcatttctg ccttttgcca gctgttgctg     360
gtatcgctgg ggctcaatgc ccctaccgt cgggtgaaat gagtttcacc caggagcagg      420
acaatgctgg cgataccatt gaggtcacgg agcagcccat gacaacacc ctgtatgtca      480 atgacaccgg tagctacatg actaccgact tggcactcc gatctccgac cagaccagtc      540
tcaaggccgg gccccgtggt cctaccctgt tggaggactt tatcttccgt cagaagcttc     600
```

| | |
|---|---|
| agcggttcga ccatgagcgt gtaagtacag taactgctgc ggtgtgtagt aacaataaat | 660 |
| tgacccagtg gttttcaatt aggtccccga gcgcgtcgtc cacgcccgtg gtgccggtgc | 720 |
| atatggtact ttcaaatcct acgccgactg gtcgaacgtc acggctgccg atttcttgag | 780 |
| tgccaacgat aaggagagcc cctatgttct gtcgcttctc tactgtggtc ggtttccgtg | 840 |
| gtagtgttga cactgcgcgt gatgttcacg gtcacgcttg tcggttctac actgacgagg | 900 |
| gtaactatgg tatcttgata tggtcaccca acaataattc aatacatgct aacagatatg | 960 |
| tctctactag acatcgtcgg tatcaatttc gccccttct tcatccagga cgccatccag | 1020 |
| ttccccgatc ttgtccacgc catcaagccc atgcccaaca atgagatccc ccaggccgct | 1080 |
| actgcacaca cttccgcttg ggacttcttc agccagcaga gcactgccct ccacagtgcc | 1140 |
| ttgtggctga tgtctggtaa cggtattcct cgttctttcc gccacatgaa cggctacgga | 1200 |
| gtccacagct tccgcttcgt cgctgccaat ggcacttcca aggtggtgcg aacaccttgg | 1260 |
| aagtcccaac agggtgttgc cagtctggtg tgggatgaag ctcaggccgc tgctggtaag | 1320 |
| aacagtgact accaccgcca ggatctgtac aatgcgatgc ccaatggcca ctacccgaaa | 1380 |
| tacgaggtca gccaatccct tgatgtctat cgatagagcc ttttgctgac aatcccctag | 1440 |
| gtccaagccc agatcatgga tgaggctgac atgcttcgtt tcggcttcga ccttctggat | 1500 |
| cccaccaagt tggtccccga ggaggttgtc ccttacactc ctctcggaat gatggagctc | 1560 |
| aatgccaacc ccaccaacta ctttgctgaa gttgaacagg ctggtgtatg tattccccat | 1620 |
| tcatcaaatg ccagacataa tctaacttct gcagttccaa cccggtcacg tcgttcctgg | 1680 |
| cattgacttc accgacgacc ccctgctgca aggccgtctc ttctcctacc tcgacactca | 1740 |
| gttgacccgt cacggcggtc ccaacttcga gcaaatcccc gtcaaccgtc ctcgcaagcc | 1800 |
| cgttcacaac aacaaccgtg acggcttcgg ccagcagcag atccccacca acaactgggc | 1860 |
| ctacaccccc aacagcatga gcaacggtta ccccatgcaa gccaaccaga cccagggtca | 1920 |
| tggtttcttc accgcgccct accgctacgc ttccggccat ctcgtccgcc agaccagccc | 1980 |
| gaccttcaat gaccactggt cccagcccgc catgttctgg aactctctga tccccgctga | 2040 |
| gcagcagatg gttgtcaacg ccattgtctt tgagaactcc aaggttaaca gccccacgt | 2100 |
| tcggaagaac gttgtcaacc agctgaacat ggtcaacaac aacctcgccg tccgtgtcgc | 2160 |
| tcgtggtctt ggtctcgatg agccctcccc caacccgact tactacacct ccaacaagac | 2220 |
| ctccaacgtc ggtaccttcg gcaagcccct cctcagcatc gagggtctgc aggtcggctt | 2280 |
| cctggcctcg aactcccacc ccgaatccat caagcagggc caggccatgg ccgcgcagtt | 2340 |
| ctctgccgct ggcgtcgacc tgaacattgt caccgaggcc tacgccgatg gtgtcaacac | 2400 |
| cacctacgcc ctgtctgatg ccatcgactt tgacgccctc atcatcgccg atggtgtgca | 2460 |
| gagcctcttc gcctcccccg ctctcgctaa ccagatgaac tctaccgcca cctctactct | 2520 |
| ctaccctcct gccagacctt tccagatcct ggtcgattct ttcaggtacg gtaagcccgt | 2580 |
| ggctgctgtc ggcagtggca gtgttgcgct caagaacgct ggtattgatt cctcccgctc | 2640 |
| tggtgtgtac actggctcga gcgagacgac ggagaagatc gccaaggagg tcttggaggg | 2700 |
| actctacact ttccgttttg tggaccggtt tgcgctggat gagtaagggt atcacgtttg | 2760 |
| tacttgtact cacgttcatc gtttgtgatg atacattgat tgatcgatag atattttgtg | 2820 |
| agatagatag agtatactag agwgkacata tctctactga tgaggtgttg tgctgctgca | 2880 |
| acacatattt atgaatatat attctcttct ttgtgaaagc tagccttcta tataatcagc | 2940 |
| aatggttaac tcttccaatt ctatagatac caatcaccta acccactcgg aatgacgaca | 3000 |

-continued

```
gaaaacatcg acatgttcgc ccaagtaaag ctacttgaac ttctacattt atgctatgct    3060
ggagtcctct cataagtcca gaataaacaa agagatccga tcctgctc                3108
```

<210> SEQ ID NO 36
<211> LENGTH: 729
<212> TYPE: PRT
<213> ORGANISM: Aspergillus niger

<400> SEQUENCE: 36

```
Met Arg His Phe Trp Leu Leu Pro Ala Val Ala Gly Ile Ala Gly Ala
1               5                   10                  15

Gln Cys Pro Tyr Leu Ser Gly Glu Met Ser Phe Thr Gln Glu Gln Asp
            20                  25                  30

Asn Ala Gly Asp Thr Ile Glu Val Thr Glu Gln Pro Ile Asp Asn Thr
        35                  40                  45

Leu Tyr Val Asn Asp Thr Gly Ser Tyr Met Thr Thr Asp Phe Gly Thr
    50                  55                  60

Pro Ile Ser Asp Gln Thr Ser Leu Lys Ala Gly Pro Arg Gly Pro Thr
65                  70                  75                  80

Leu Leu Glu Asp Phe Ile Phe Arg Gln Lys Leu Gln Arg Phe Asp His
                85                  90                  95

Glu Arg Val Pro Glu Arg Val Val His Ala Arg Gly Gly Ala Tyr Gly
            100                 105                 110

Thr Phe Lys Ser Tyr Ala Asp Trp Ser Asn Val Thr Ala Ala Asp Phe
        115                 120                 125

Leu Ser Ala Asn Asp Lys Glu Thr Pro Met Phe Cys Arg Phe Ser Thr
    130                 135                 140

Val Val Gly Phe Arg Gly Ser Val Asp Thr Ala Arg Asp Val His Gly
145                 150                 155                 160

His Ala Cys Arg Phe Tyr Thr Asp Glu Gly Asn Tyr Asp Ile Val Gly
                165                 170                 175

Ile Asn Phe Ala Pro Phe Phe Ile Gln Asp Ala Ile Gln Phe Pro Asp
            180                 185                 190

Leu Val His Ala Ile Lys Pro Met Pro Asn Asn Glu Ile Pro Gln Ala
        195                 200                 205

Ala Thr Ala His Thr Ser Ala Trp Asp Phe Phe Ser Gln Gln Ser Thr
    210                 215                 220

Ala Leu His Ser Ala Leu Trp Leu Met Ser Gly Asn Gly Ile Pro Arg
225                 230                 235                 240

Ser Phe Arg His Met Asn Gly Tyr Gly Val His Ser Phe Arg Phe Val
                245                 250                 255

Ala Ala Asn Gly Thr Ser Lys Val Val Arg Thr Pro Lys Ser Gln
            260                 265                 270

Gln Gly Val Ala Ser Leu Val Trp Asp Glu Ala Gln Ala Ala Gly
        275                 280                 285

Lys Asn Ser Asp Tyr His Arg Gln Asp Leu Tyr Asn Ala Met Pro Asn
    290                 295                 300

Gly His Tyr Pro Lys Tyr Glu Leu Gln Ala Gln Ile Met Asp Glu Ala
305                 310                 315                 320

Asp Met Leu Arg Phe Gly Phe Asp Leu Leu Asp Pro Thr Lys Leu Val
                325                 330                 335

Pro Glu Glu Val Val Pro Tyr Thr Pro Leu Gly Met Met Glu Leu Asn
            340                 345                 350
```

```
Ala Asn Pro Thr Asn Tyr Phe Ala Glu Val Glu Gln Ala Gly Phe Gln
            355                 360                 365

Pro Gly His Val Val Pro Gly Ile Asp Phe Thr Asp Pro Leu Leu
370                 375                 380

Gln Gly Arg Leu Phe Ser Tyr Leu Asp Thr Gln Leu Thr Arg His Gly
385                 390                 395                 400

Gly Pro Asn Phe Glu Gln Ile Pro Val Asn Arg Pro Arg Lys Pro Val
                405                 410                 415

His Asn Asn Asn Arg Asp Gly Phe Gln Gln Gln Ile Pro Thr Asn
            420                 425                 430

Asn Trp Ala Tyr Thr Pro Asn Ser Met Ser Asn Gly Tyr Pro Met Gln
        435                 440                 445

Ala Asn Gln Thr Gln Gly His Gly Phe Phe Thr Ala Pro Tyr Arg Tyr
    450                 455                 460

Ala Ser Gly His Leu Val Arg Gln Thr Ser Pro Thr Phe Asn Asp His
465                 470                 475                 480

Trp Ser Gln Pro Ala Met Phe Trp Asn Ser Leu Ile Pro Ala Glu Gln
                485                 490                 495

Gln Met Val Val Asn Ala Ile Val Phe Glu Asn Ser Lys Val Asn Ser
            500                 505                 510

Pro His Val Arg Lys Asn Val Val Asn Gln Leu Asn Met Val Asn Asn
        515                 520                 525

Asn Leu Ala Val Arg Val Ala Arg Gly Leu Gly Leu Asp Glu Pro Ser
    530                 535                 540

Pro Asn Pro Thr Tyr Tyr Thr Ser Asn Lys Thr Ser Asn Val Gly Thr
545                 550                 555                 560

Phe Gly Lys Pro Leu Leu Ser Ile Glu Gly Leu Gln Val Gly Phe Leu
                565                 570                 575

Ala Ser Asn Ser His Pro Glu Ser Ile Lys Gln Gly Gln Ala Met Ala
            580                 585                 590

Ala Gln Phe Ser Ala Ala Gly Val Asp Leu Asn Ile Val Thr Glu Ala
        595                 600                 605

Tyr Ala Asp Gly Val Asn Thr Thr Tyr Ala Leu Ser Asp Ala Ile Asp
    610                 615                 620

Phe Asp Ala Leu Ile Ile Ala Asp Gly Val Gln Ser Leu Phe Ala Ser
625                 630                 635                 640

Pro Ala Leu Ala Asn Gln Met Asn Ser Thr Ala Ser Thr Leu Tyr
                645                 650                 655

Pro Pro Ala Arg Pro Phe Gln Ile Leu Val Asp Ser Phe Arg Tyr Gly
            660                 665                 670

Lys Pro Val Ala Val Gly Ser Gly Ser Val Ala Leu Lys Asn Ala
        675                 680                 685

Gly Ile Asp Ser Ser Arg Ser Gly Val Tyr Thr Gly Ser Ser Glu Thr
    690                 695                 700

Thr Glu Lys Ile Ala Lys Glu Val Leu Glu Gly Leu Tyr Thr Phe Arg
705                 710                 715                 720

Phe Val Asp Arg Phe Ala Leu Asp Glu
                725
```

<210> SEQ ID NO 37
<211> LENGTH: 684
<212> TYPE: PRT
<213> ORGANISM: Humicola grisea

<400> SEQUENCE: 37

```
Met Asn Arg Val Thr Asn Leu Leu Ala Trp Ala Gly Ala Ile Gly Leu
1               5                   10                  15

Ala Gln Ala Thr Cys Pro Phe Ala Asp Pro Ala Ala Leu Tyr Arg Arg
            20                  25                  30

Gln Asp Thr Thr Ser Gly Gln Ser Pro Leu Ala Ala Tyr Glu Val Asp
        35                  40                  45

Asp Ser Thr Gly Tyr Leu Thr Ser Asp Val Gly Gly Pro Ile Gln Asp
    50                  55                  60

Gln Thr Ser Leu Lys Ala Gly Ile Arg Gly Pro Thr Leu Leu Glu Asp
65                  70                  75                  80

Phe Met Phe Arg Gln Lys Ile Gln His Phe Asp His Glu Arg Val Pro
                85                  90                  95

Glu Arg Ala Val His Ala Arg Gly Ala Gly Ala His Gly Thr Phe Thr
            100                 105                 110

Ser Tyr Ala Asp Trp Ser Asn Ile Thr Ala Ala Ser Phe Leu Asn Ala
        115                 120                 125

Thr Gly Lys Gln Thr Pro Val Phe Val Arg Phe Ser Thr Val Ala Gly
130                 135                 140

Ser Arg Gly Ser Ala Asp Thr Ala Arg Asp Val His Gly Phe Ala Thr
145                 150                 155                 160

Arg Phe Tyr Thr Asp Glu Gly Asn Phe Asp Ile Val Gly Asn Asn Ile
                165                 170                 175

Pro Val Phe Phe Ile Gln Asp Ala Ile Gln Phe Pro Asp Leu Ile His
            180                 185                 190

Ser Val Lys Pro Ser Pro Asp Asn Glu Ile Pro Gln Ala Ala Thr Ala
        195                 200                 205

His Asp Ser Ala Trp Asp Phe Phe Ser Gln Gln Pro Ser Ala Met His
    210                 215                 220

Thr Leu Phe Trp Ala Met Ser Gly His Gly Ile Pro Arg Ser Tyr Arg
225                 230                 235                 240

His Met Asp Gly Phe Gly Val His Thr Phe Arg Phe Val Lys Asp Asp
                245                 250                 255

Gly Ser Ser Lys Leu Ile Lys Trp His Phe Lys Ser Arg Gln Gly Lys
            260                 265                 270

Ala Ser Leu Val Trp Glu Glu Ala Gln Val Leu Ser Gly Lys Asn Ala
        275                 280                 285

Asp Phe His Arg Gln Asp Leu Trp Asp Ala Ile Glu Ser Gly Asn Gly
    290                 295                 300

Pro Glu Trp Asp Val Cys Val Gln Ile Val Asp Glu Ser Gln Ala Gln
305                 310                 315                 320

Ala Phe Gly Phe Asp Leu Leu Asp Pro Thr Lys Ile Ile Pro Glu Glu
                325                 330                 335

Tyr Ala Pro Leu Thr Lys Leu Gly Leu Leu Lys Leu Asp Arg Asn Pro
            340                 345                 350

Thr Asn Tyr Phe Ala Glu Thr Glu Gln Val Met Phe Gln Pro Gly His
        355                 360                 365

Ile Val Arg Gly Val Asp Phe Thr Glu Asp Pro Leu Leu Gln Gly Arg
    370                 375                 380

Leu Phe Ser Tyr Leu Asp Thr Gln Leu Asn Arg Asn Gly Gly Pro Asn
385                 390                 395                 400

Phe Glu Gln Leu Pro Ile Asn Met Pro Arg Val Pro Ile His Asn Asn
                405                 410                 415
```

```
Asn Arg Asp Gly Ala Gly Gln Met Phe Ile His Arg Asn Lys Tyr Pro
            420                 425                 430

Tyr Thr Pro Asn Thr Leu Asn Ser Gly Tyr Pro Arg Gln Ala Asn Gln
        435                 440                 445

Asn Ala Gly Arg Gly Phe Phe Thr Ala Pro Gly Arg Thr Val Ser Gly
    450                 455                 460

Ala Leu Val Arg Glu Val Ser Pro Thr Phe Asn Asp His Trp Ser Gln
465                 470                 475                 480

Pro Arg Leu Phe Phe Asn Ser Leu Thr Pro Val Glu Gln Gln Phe Leu
                485                 490                 495

Val Asn Ala Met Arg Phe Glu Ile Ser Leu Val Lys Ser Glu Glu Cys
            500                 505                 510

Arg Lys Asn Val Leu Thr Gln Leu Asn Arg Val Ser His Asp Val Ala
        515                 520                 525

Val Arg Val Ala Ala Ala Ile Gly Leu Ala Ala Pro Asp Ala Asp Asp
    530                 535                 540

Thr Tyr Tyr His Asn Asn Lys Thr Ala Gly Val Ser Ile Leu Gly Ser
545                 550                 555                 560

Gly Pro Leu Pro Thr Ile Lys Thr Leu Arg Val Gly Ile Leu Ala Thr
                565                 570                 575

Thr Ser Glu Ser Ser Ala Leu Asp Gln Ala Ala Gln Leu Arg Thr Arg
            580                 585                 590

Leu Glu Lys Asp Gly Leu Val Val Thr Val Ala Glu Thr Leu Arg
        595                 600                 605

Glu Gly Val Asp Gln Thr Tyr Ser Thr Ala Asp Ala Thr Gly Phe Asp
610                 615                 620

Gly Val Val Val Asp Gly Ala Ala Ala Leu Phe Ala Ser Thr Ala
625                 630                 635                 640

Ser Ser Pro Leu Phe Pro Thr Gly Arg Pro Leu Gln Ile Phe Val Asp
                645                 650                 655

Ala Tyr Arg Trp Gly Lys Pro Val Gly Val Cys Gly Gly Lys Ser Ser
            660                 665                 670

Glu Val Leu Asp Ala Ala Asp Val Pro Glu Asn Gly
        675                 680

<210> SEQ ID NO 38
<211> LENGTH: 40
<212> TYPE: DNA
<213> ORGANISM: Artificial Sequence
<220> FEATURE:
<223> OTHER INFORMATION: Synthetic Construct

<400> SEQUENCE: 38
acacaactgg ggatccacca tgcgaggggc atactctctc                            40

<210> SEQ ID NO 39
<211> LENGTH: 43
<212> TYPE: DNA
<213> ORGANISM: Artificial Sequence
<220> FEATURE:
<223> OTHER INFORMATION: Synthetic Construct

<400> SEQUENCE: 39
gtcaccctct agatctaaca agttactcgt gttaatcgtg gaa                        43

<210> SEQ ID NO 40
<211> LENGTH: 44
<212> TYPE: DNA
```

```
<213> ORGANISM: Artificial Sequence
<220> FEATURE:
<223> OTHER INFORMATION: Synthetic Construct

<400> SEQUENCE: 40
acacaactgg ggatccacca tgaacagagt cacgaatctc ctcg                    44

<210> SEQ ID NO 41
<211> LENGTH: 43
<212> TYPE: DNA
<213> ORGANISM: Artificial Sequence
<220> FEATURE:
<223> OTHER INFORMATION: Synthetic Construct

<400> SEQUENCE: 41
gtcaccctct agatctggta caactcccac cctattcctt ctc                     43

<210> SEQ ID NO 42
<211> LENGTH: 36
<212> TYPE: DNA
<213> ORGANISM: Artificial Sequence
<220> FEATURE:
<223> OTHER INFORMATION: Synthetic Construct

<400> SEQUENCE: 42
acacaactgg ggatccacca tgcgcgcagt gcagct                             36

<210> SEQ ID NO 43
<211> LENGTH: 47
<212> TYPE: DNA
<213> ORGANISM: Artificial Sequence
<220> FEATURE:
<223> OTHER INFORMATION: Synthetic Construct

<400> SEQUENCE: 43
gtcaccctct agatctgtcg actattccaa ccttcctata tggacac                 47
```

METHODS FOR DEGRADING OR CONVERTING CELLULOSIC MATERIAL

CROSS-REFERENCE TO RELATED APPLICATIONS

This application is a 35 U.S.C. 371 national application of PCT/CN2012/073040 filed Mar. 26, 2012 which claims priority or the benefit under 35 U.S.C. 119 of PCT application nos. PCT/CN2011/072143 and PCT/CN2011/084230 filed Mar. 25, 2011 and Dec. 19, 2011, respectively, and U.S. provisional application No. 61/477,418 filed Apr. 20, 2011, the contents of which are fully incorporated herein by reference.

REFERENCE TO A SEQUENCE LISTING

This application contains a Sequence Listing in computer readable form. The computer readable form is incorporated herein by reference.

BACKGROUND OF THE INVENTION

Field of the Invention

The present invention relates to methods for degrading or converting cellulosic material and enzyme composition for degrading or converting cellulosic material.

Description of the Related Art

Catalases [hydrogen peroxide: hydrogen peroxide oxidoreductases (EC 1.11.1.6)] are enzymes which catalyze the conversion of hydrogen peroxide ($H_2O_2$) to oxygen ($O_2$) and water ($H_2O$). These ubiquitous enzymes have been purified from a variety of animal tissues, plants and microorganisms (Chance and Maehly, 1955, *Methods Enzymol.* 2: 764-791).

Catalase preparations are used commercially for diagnostic enzyme kits, for the enzymatic production of sodium gluconate from glucose, for the neutralization of $H_2O_2$ waste, for removal of $H_2O_2$ from textile fabrics, and for the removal of $H_2O_2$ and/or generation of $O_2$ in foods and beverages.

Cellulose is a polymer of simple sugars covalently linked by beta-1,4-bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic material has the advantages of the ready availability of large amounts of feedstock and the desirability of avoiding burning or land filling the materials. Wood, agricultural residues, herbaceous crops, and municipal solid wastes have been considered as feedstocks. These materials primarily consist of cellulose, hemicellulose, and lignin. Once the lignocellulose is converted to simple sugars, e.g., glucose, the simple sugars can further be converted to many useful substances, e.g., fuel, potable ethanol, fermentation products and/or chemicals (e.g., acids, alcohols, ketones, gases, and the like).

It would be advantageous in the art to improve methods for degrading or converting a cellulosic material.

SUMMARY OF THE INVENTION

The present invention relates to methods for degrading or converting a cellulosic material, comprising: treating the cellulosic material with an enzyme composition in the presence of a polypeptide having catalase activity.

The present invention also relates to methods for producing a fermentation product, comprising:

(a) saccharifying a cellulosic material with an enzyme composition in the presence of a polypeptide having catalase activity;

(b) fermenting the saccharified cellulosic material with one or more (e.g., several) fermenting microorganisms to produce the fermentation product; and (c) recovering the fermentation product from the fermentation.

The present invention further relates to methods of fermenting a cellulosic material, comprising: fermenting the cellulosic material with one or more (e.g., several) fermenting microorganisms, wherein the cellulosic material is hydrolyzed with an enzyme composition in the presence of a polypeptide having catalase activity.

The present invention even further relates to an enzyme composition for degrading or converting a cellulosic material comprising enzymes having cellulolytic activity and/or xylan degrading activity and a polypeptide having catalase activity; and the uses thereof.

BRIEF DESCRIPTION OF THE FIGURES

FIG. 1 shows the genomic DNA sequence (SEQ ID NO: 3) and the amino acid sequence (SEQ ID NO: 4) of a *Talaromyces stipitatus* catalase gene.

FIG. 2 shows the genomic DNA sequence (SEQ ID NO: 5) and the amino acid sequence (SEQ ID NO: 6) of a *Humicola insolens* catalase gene.

FIG. 3 shows the genomic DNA sequence (SEQ ID NO: 7) and the amino acid sequence (SEQ ID NO: 8) of a *Penicillium emersonii* catalase gene.

DEFINITIONS

Catalase activity: The term "catalase activity" is defined herein as a hydrogen-peroxide:hydrogen-peroxide oxidoreductase activity (EC 1.11.1.6) that catalyzes the conversion of 2 $H_2O_2$ to $O_2$+2 $H_2O$. For purposes of the present invention, catalase activity is determined according to U.S. Pat. No. 5,646,025. One unit of catalase activity equals the amount of enzyme that catalyzes the oxidation of 1 µmole of hydrogen peroxide under the assay conditions.

In one aspect, the catalases used in the present invention have at least 20%, e.g., at least 40%, at least 50%, at least 60%, at least 70%, at least 80%, at least 90%, at least 95%, or at least 100% of the catalase activity of the mature polypeptide of SEQ ID NO: 2, the mature polypeptide of SEQ ID NO: 4, the mature polypeptide of SEQ ID NO: 6, or the mature polypeptide of SEQ ID NO: 8.

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 µmole of p-nitrophenolate anion per minute at pH 5, 25° C.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methylglucuronic acid per minute at pH 5, 40° C.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581. In the present invention, the Tomme et al. method can be used to determine cellobiohydrolase activity.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is arundo. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is miscanthus. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is eucalyptus. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide main; wherein the fragment has catalase activity. In one aspect, a fragment contains at least 632 amino acid residues, e.g., at least 670 amino acid residues or at least 708 amino acid residues of SEQ ID NO: 2. In another aspect, a fragment contains at least 622 amino acid residues, e.g., at least 659 amino acid residues or at least 696 amino acid residues of SEQ ID NO: 4. In another aspect, a fragment contains at least 652 amino acid residues, e.g., at least 689 amino acid residues or at least 727 amino acid residues of SEQ ID NO: 6. In another aspect, a fragment contains at least 614 amino acid residues, e.g., at least 650 amino acid residues or at least 686 amino acid residues of SEQ ID NO: 8.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a catalase of the present invention. The term "host cell" encompasses any progeny of a parent cell that is not identical to the parent cell due to mutations that occur during replication.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one embodiment, the mature polypeptide is amino acids 1 to 746 of SEQ ID NO: 2. In another embodiment, the mature polypeptide is amino acids 20 to 733 of SEQ ID NO: 4 based on the SignalP program that predicts amino acids 1 to 19 of SEQ ID NO: 4 are a signal peptide. In another embodiment, the mature polypeptide is amino acids 20 to 765 of SEQ ID NO: 6 based on the SignalP program that predicts amino acids 1 to 19 of SEQ ID NO: 6 are a signal peptide. In another embodiment, the mature polypeptide is amino acids 20 to 741 of SEQ ID NO: 8 based on the SignalP program that predicts amino acids 1 to 19 of SEQ ID NO: 8 are a signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having catalase activity. In one embodiment, the mature polypeptide coding sequence is nucleotides 1 to 2351 of SEQ ID NO: 1 or the cDNA sequence thereof. In another embodiment, the mature polypeptide coding sequence is nucleotides 58 to 2418 of SEQ ID NO: 3 or the cDNA sequence thereof based on the SignalP program that predicts nucleotides 1 to 57 of SEQ ID NO: 3 encode a signal peptide. In another embodiment, the mature polypeptide coding sequence is nucleotides 58 to 3040 of SEQ ID NO: 5 or the cDNA sequence thereof based on the SignalP program that predicts nucleotides 1 to 57 of SEQ ID NO: 5 encode a signal peptide. In another embodiment, the mature polypeptide coding sequence is nucleotides 58 to 2476 of SEQ ID NO: 7 or the cDNA sequence thereof based on the SignalP program that predicts nucleotides 1 to 57 of SEQ ID NO: 7 encode a signal peptide.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and either 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes A/S, Bagsvrd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment− Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Variant: The term "variant" means a polypeptide having catalase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the*

*Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, Biochemical Journal 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

DETAILED DESCRIPTION OF THE INVENTION

Methods of Processing Cellulosic Material

The present invention relates to methods for degrading or converting a cellulosic material, comprising: treating the cellulosic material with an enzyme composition in the presence of a polypeptide having catalase activity. In one aspect, the method further comprises recovering the degraded or converted cellulosic material.

The present invention also relates to methods for producing a fermentation product, comprising:

(a) saccharifying a cellulosic material with an enzyme composition in the presence of a polypeptide having catalase activity;

(b) fermenting the saccharified cellulosic material with one or more (e.g., several) fermenting microorganisms to produce the fermentation product; and (c) recovering the fermentation product from the fermentation.

The present invention further relates to methods of fermenting a cellulosic material, comprising: fermenting the cellulosic material with one or more (e.g., several) fermenting microorganisms, wherein the cellulosic material is hydrolyzed with an enzyme composition in the presence of a polypeptide having catalase activity. In one aspect, the fermenting of the cellulosic material produces a fermentation product. In another aspect, the method further comprises recovering the fermentation product from the fermentation.

In the methods described above, the presence of the polypeptide having catalase activity increases the hydrolysis of the cellulosic material compared to the absence of the polypeptide having catalase activity.

The methods of the present invention can be used to saccharify the cellulosic material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic material typically involves pretreatment, enzymatic hydrolysis (saccharification), and fermentation.

The processing of the cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, cellotriose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: fluidized bed, upflow blanket, immobilized, and extruder type reactors for hydrolysis and/or fermentation.

Pretreatment. In practicing the methods of the present invention, any pretreatment process known in the art can be used to disrupt plant cell wall components of cellulosic material (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, cellulosic material is heated to disrupt the plant cell wall components, including lignin, hemicellulose, and cellulose to make the cellulose and other fractions, e.g., hemicellulose, accessible to enzymes. Cellulosic material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-30 minutes, more preferably 1-15 minutes, even more preferably 3-12 minutes, and most preferably 4-10 minutes, where the optimal residence time depends on temperature range and any addition of a chemical catalyst. Steam pretreatment allows for relatively high solids loadings, so that cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

In dilute acid pretreatment, cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose is removed.

Other examples of suitable pretreatment methods are described by Schell et al., 2003, *Appl. Biochem. and Biotechnol.* Vol. 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt acid, even more preferably 0.1 to 5 wt % acid, and most preferably 0.2 to 2.0 wt % acid. The acid is contacted with cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Mechanical Pretreatment: The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: Cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, cellulosic material is subjected to mechanical, chemical, or physical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification. In the hydrolysis step, also known as saccharification, the cellulosic material, e.g., pretreated, is hydrolyzed to break down cellulose and alternatively also hemicellulose to sugars, such as glucose, cellobiose, xylose, xylulose, arabinose, mannose, galactose, and/or soluble oligosaccharides. The sugars, and/or soluble oligosaccharides can further be further used to produce an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide.

The hydrolysis is performed enzymatically by an enzyme composition in the presence of a polypeptide having catalase activity of the present invention. The enzymes of the compositions and the polypeptide having catalase activity can also be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme(s), i.e., optimal for the enzyme(s). The hydrolysis can be carried out as a fed batch or continuous process where the cellulosic material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

Enzyme Composition

The enzyme compositions can comprise any protein that is useful in degrading or converting cellulosic material. The compositions may comprise one enzyme as the major enzymatic component, e.g., a mono-component composition, or multiple enzymes. The compositions may be prepared in accordance with methods known in the art and may be in the form of a liquid or a dry composition. The compositions may be stabilized in accordance with methods known in the art.

In one aspect, an enzyme composition for degrading or converting a cellulosic material comprises one or more (e.g., several) enzymes having cellulolytic and/or hemicellulolytic activity and a polypeptide having catalase activity.

In an embodiment, the enzyme composition comprises or further comprises one or more (e.g., several) proteins selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another embodiment, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another embodiment, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another embodiment, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin.

In the methods of the present invention, the enzyme(s) can be added prior to or during saccharification, saccharification and fermentation, or fermentation. The enzymes having cellulolytic and/or hemicellulolytic activity and a polypeptide having catalase activity can be added simultaneously or sequentially.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the methods of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptide(s) having catalase activity depend on several factors including, but not limited to, the mixture of component cellulolytic enzymes, the cellulosic material, the concentration of cellulosic material, the pretreatment(s) of the cellulosic material, temperature, time, pH, and inclusion of fermenting organism (e.g., yeast for Simultaneous Saccharification and Fermentation).

In a preferred aspect, an effective amount of cellulolytic or hemicellulolytic enzyme to the cellulosic material is about 0.5 to about 50 mg, preferably about 0.5 to about 40 mg, more preferably about 0.5 to about 25 mg, more preferably about 0.75 to about 20 mg, more preferably about 0.75 to about 15 mg, even more preferably about 0.5 to about 10 mg, and most preferably about 1.0 to about 10 mg per g of the cellulosic material.

In another preferred aspect, an effective amount of polypeptide(s) having catalase activity to the cellulosic material is about 0.001 to about 100.0 mg, preferably about 0.01 to about 50 mg, more preferably about 0.01 to about 40 mg, more preferably about 0.01 to about 30 mg, more preferably about 0.01 to about 20 mg, more preferably about 0.01 to about 10 mg, more preferably about 0.025 to about 8 mg, more preferably bout 0.05 to about 6 mg, more preferably about 0.075 to about 5 mg, more preferably about 0.1 to about 4 mg, even more preferably about 0.15 to about 3 mg, and most preferably about 0.25 to about 1.0 mg per g of the cellulosic material.

In another preferred aspect, an effective amount of polypeptide(s) having catalase activity to cellulolytic or hemicellulolytic enzyme is about 0.005 to about 1.0 g, preferably about 0.01 to about 1.0 g, more preferably about 0.15 to about 0.75 g, more preferably about 0.15 to about 0.5 g, more preferably about 0.1 to about 0.5 g, even more preferably about 0.1 to about 0.5 g, and most preferably about 0.05 to about 0.2 g per g of cellulolytic or hemicellulolytic enzyme.

In another aspect, an effective amount of a GH61 polypeptide having cellulolytic enhancing activity to cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably about 0.025 to about 1.5 mg, more preferably about 0.05 to about 1.25 mg, more preferably about 0.075 to about 1.25 mg, more preferably about 0.1 to about 1.25 mg, even more preferably about 0.15 to about 1.25 mg, and most preferably about 0.25 to about 1.0 mg per g of cellulosic material.

In another aspect, an effective amount of a GH61 polypeptide having cellulolytic enhancing activity to cellulolytic enzyme protein is about 0.005 to about 1.0 g, preferably about 0.01 to about 1.0 g, more preferably about 0.15 to about 0.75 g, more preferably about 0.15 to about 0.5 g, more preferably about 0.1 to about 0.5 g, even more preferably about 0.1 to about 0.5 g, and most preferably about 0.05 to about 0.2 g per g of cellulolytic enzyme protein.

The polypeptides having cellulolytic enzyme activity or hemicellulolytic enzyme activity as well as other proteins/polypeptides useful in the degradation of the cellulosic material, e.g., polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia,* or *Oceanobacillus* polypeptide having enzyme activity, or a Gram negative bacterial polypeptide such as an *E. coli, Pseudomonas, Salmonella, Campylobacter, Helicobacter,*

*Flavobacterium, Fusobacterium, Ilyobacter, Neisseria,* or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having enzyme activity.

In another aspect, the polypeptide is a *Streptococcus equisimilis, Streptococcus pyogenes, Streptococcus uberis,* or *Streptococcus equi* subsp. *Zooepidemicus* polypeptide having enzyme activity.

In another aspect, the polypeptide is a *Streptomyces achromogenes, Streptomyces avermitilis, Streptomyces coelicolor, Streptomyces griseus,* or *Streptomyces lividans* polypeptide having enzyme activity.

The polypeptide having enzyme activity may also be a fungal polypeptide, and more preferably a yeast polypeptide such as a *Candida, Kluyveromyces, Pichia, Saccharomyces, Schizosaccharomyces,* or *Yarrowia* polypeptide having enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having enzyme activity.

In one aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having enzyme activity.

In one aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride,* or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec Ctec3 (Novozymes A/S), CELLIC® CTec CTec2 (Novozymes A/S), CELLIC® CTec (Novozymes A/S), CELLUCLAST™ (Novozymes A/S), NOVOZYM™ 188 (Novozymes NS), CELLUZYME™ (Novozymes A/S), CEREFLO™ (Novozymes A/S), and ULTRAFLO™ (Novozymes A/S), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the method of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263; *Trichoderma reesei* Cel7B endoglucanase I (GENBANK™ accession no. M15665); *Trichoderma reesei* endoglucanase II (Saloheimo, et al., 1988, *Gene* 63:11-22; *Trichoderma reesei* Cel5A endoglucanase II (GENBANK™ accession no. M19373); *Trichoderma reesei* endoglucanase III (Okada et al., 1988, *Appl. Environ. Microbiol.* 64: 555-563; GENBANK™ accession no. AB003694); *Trichoderma reesei* endoglucanase V (Saloheimo et al., 1994, *Molecular Microbiology* 13: 219-228; GENBANK™ accession no. Z33381); *Aspergillus aculeatus* endoglucanase (Ooi et al., 1990, *Nucleic Acids Research* 18: 5884); *Aspergillus kawachii* endoglucanase (Sakamoto et al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V; *Myceliophthora thermophila* CBS 117.65 endoglucanase; basidiomycete CBS 495.95 endoglucanase; basidiomycete CBS 494.95 endoglucanase; *Thielavia terrestris* NRRL 8126 CEL6B endoglucanase; *Thielavia terrestris* NRRL 8126 CEL6C endoglucanase; *Thielavia terrestris* NRRL 8126 CEL7C endoglucanase; *Thielavia terrestris* NRRL 8126 CEL7E endoglucanase; *Thielavia terrestris* NRRL 8126 CEL7F endoglucanase; *Cladorrhinum foecundissimum* ATCC 62373 CEL7A endoglucanase; and *Trichoderma reesei* strain No. VTT-D-80133 endoglucanase (GENBANK™ accession no. M15665).

Examples of cellobiohydrolases useful in the present invention include, but are not limited to, *Trichoderma reesei* cellobiohydrolase I; *Trichoderma reesei* cellobiohydrolase II; *Humicola insolens* cellobiohydrolase I; *Myceliophthora thermophila* cellobiohydrolase II; *Thielavia terrestris* cellobiohydrolase II (CEL6A); *Chaetomium thermophilum* cellobiohydrolase I; and *Chaetomium thermophilum* cellobiohydrolase II.

Examples of beta-glucosidases useful in the present invention include, but are not limited to, *Aspergillus oryzae* beta-glucosidase; *Aspergillus fumigatus* beta-glucosidase; *Penicillium brasilianum* IBT 20888 beta-glucosidase; *Aspergillus niger* beta-glucosidase; and *Aspergillus aculeatus* beta-glucosidase.

The *Aspergillus oryzae* beta-glucosidase can be obtained according to WO 2002/095014. The *Aspergillus fumigatus* beta-glucosidase can be obtained according to WO 2005/047499. The *Penicillium brasilianum* beta-glucosidase can be obtained according to WO 2007/019442. The *Aspergillus niger* beta-glucosidase can be obtained according to Dan et al., 2000, *J. Biol. Chem.* 275: 4973-4980. The *Aspergillus aculeatus* beta-glucosidase can be obtained according to Kawaguchi et al., 1996, *Gene* 173: 287-288.

The beta-glucosidase may be a fusion protein. In one aspect, the beta-glucosidase is the *Aspergillus oryzae* beta-glucosidase variant BG fusion protein or the *Aspergillus oryzae* beta-glucosidase fusion protein obtained according to WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in EP 495,257, EP 531,315, EP 531,372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/0076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 4,435,307, U.S. Pat. No. 5,457,046, U.S. Pat. No. 5,648,263, U.S. Pat. No. 5,686,593, U.S. Pat. No. 5,691,178, U.S. Pat. No. 5,763,254, and U.S. Pat. No. 5,776,757.

In the methods of the present invention, any GH61 polypeptide having cellulolytic enhancing activity can be used.

In a first aspect, the GH61 polypeptide having cellulolytic enhancing activity comprises the following motifs:

[ILMV]-P-X(4,5)-G-X-Y-[ILMV]—X-R-X4EQFX(4)-[HNQ] and [FW]-[TF]-K-[AIV], wherein X is any amino acid, X(4,5) is any amino acid at 4 or 5 contiguous positions, and X(4) is any amino acid at 4 contiguous positions.

The polypeptide comprising the above-noted motifs may further comprise:

H—X(1,2)-G-P-X(3)-[YW]-[AILMV],

[EQ]-X-Y-X(2)-C-X-[EHQN]-[FILV]-X-[ILV], or

H-X(1,2)-G-P-X(3)-[YW]-[AILMV] and [EQ]-X-Y-X(2)-C-X-[EHQN]-[FILV]-X-[ILV], wherein X is any amino acid, X(1,2) is any amino acid at 1 position or 2 contiguous positions, X(3) is any amino acid at 3 contiguous positions, and X(2) is any amino acid at 2 contiguous positions. In the above motifs, the accepted IUPAC single letter amino acid abbreviation is employed.

In a preferred aspect, the GH61 polypeptide having cellulolytic enhancing activity further comprises H-X(1,2)-G-P-X(3)-[YW]-[AILMV]. In another preferred aspect, the GH61 polypeptide having cellulolytic enhancing activity further comprises [EQ]-X-Y-X(2)-C-X-[EHQN]-[FILV]-X-[ILV]. In another preferred aspect, the GH61 polypeptide having cellulolytic enhancing activity further comprises H-X(1,2)-G-P-X(3)-[YW]-[AILMV] and [EQ]-X-Y-X(2)-C-X-[EHQN]-[FILV]-X-[ILV].

In a second aspect, the GH61 polypeptide having cellulolytic enhancing activity comprises the following motif:

[ILMV]-P-x(4,5)-G-x-Y-[ILMV]-x-R-x-[EQ]-x(3)-A-[HNQ], wherein x is any amino acid, x(4,5) is any amino acid at 4 or 5 contiguous positions, and x(3) is any amino acid at 3 contiguous positions. In the above motif, the accepted IUPAC single letter amino acid abbreviation is employed.

Examples of GH61 polypeptides having cellulolytic enhancing activity useful in the methods of the present invention include, but are not limited to, polypeptides having cellulolytic enhancing activity from *Thielavia terrestris* (WO 2005/074647, WO/2008/148131 and WO 2011/035027); polypeptides having cellulolytic enhancing activity from *Thermoascus aurantiacus* (WO 2005/074656 and WO 2010/065830); polypeptides having cellulolytic enhancing activity from *Trichoderma reesei* (WO 2007/089290); and polypeptides having cellulolytic enhancing activity from *Myceliophthora thermophila* (WO 2009/085935; WO 2009/085859; WO 2009/085864; and WO 2009/085868); polypeptides having cellulolytic enhancing activity from *Aspergillus fumigatus* (WO 2010/138754); and polypeptides having cellulolytic enhancing activity from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese sulfate.

In one aspect, the GH61 polypeptide having cellulolytic enhancing activity is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxyphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothienopyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl) furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, and about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, and about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using methods standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-6}$ to about 1 g, about $10^{-6}$ to about $10^{-1}$ g, about $10^4$ to about $10^{-1}$ g, about $10^{-3}$ to about $10^{-1}$ g, and about $10^{-3}$ to about $10^{-2}$ g per g of cellulose.

In one embodiment, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), VISCOZYME® (Novozymes A/S), ULTRAFLO® (Novozymes A/S), PULPZYME® HC (Novozymes A/S), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the methods of the present invention include, but are not limited to, *Aspergillus aculeatus* xylanase (GeneSeqP: AAR63790; WO 94/21785); *Aspergillus fumigatus* xylanases (WO 2006/078256); *Penicillium pinophilum* (WO 2011/041405); *Penicillium* sp. (WO 2010/126772); *Thielavia terrestris* NRRL 8126 (WO 2009/079210); and *Trichophaea saccata* GH10 (WO 2011/057083).

Examples of beta-xylosidases useful in the methods of the present invention include, but are not limited to, *Trichoderma reesei* beta-xylosidase (UniProtKB/TrEMBL accession number Q92458); *Talaromyces emersonii* (SwissProt accession number Q8X212); and *Neurospora crassa* (SwissProt accession number Q7SOW4).

Examples of acetylxylan esterases useful in the methods of the present invention include, but are not limited to, acetylxylan esterases from *Aspergillus aculeatus* (WO 2010/108918); *Chaetomium globosum* (Uniprot accession number Q2GWX4); *Chaetomium gracile* (GeneSeqP accession number AAB82124); *Humicola insolens* DSM 1800 (WO 2009/073709); *Hypocrea jecorina* (WO 2005/001036); *Myceliophthora thermophila* (WO 2010/014880); *Neurospora crassa* (UniProt accession number q7s259); *Phaeosphaeria nodorum* (Uniprot accession number Q0UHJ1); and *Thielavia terrestris* NRRL 8126 (WO 2009/042846).

Examples of ferulic acid esterases useful in the methods of the present invention include, but are not limited to, *Humicola insolens* DSM 1800 feruloyl esterase (WO 2009/076122), *Neurospora crassa* feruloyl esterase (UniProt accession number Q9HGR3), and *Neosartorya fischeri* feruloyl esterase (UniProt Accession number A1D9T4).

Examples of arabinofuranosidases useful in the methods of the present invention include, but are not limited to, arabinofuranosidases from *Aspergillus niger* (GeneSeqP accession number AAR94170); *Humicola insolens* DSM 1800 (WO 2006/114094 and WO 2009/073383); and *M. giganteus* (WO 2006/114094).

Examples of alpha-glucuronidases useful in the methods of the present invention include, but are not limited to, alpha-glucuronidases from *Aspergillus clavatus* (UniProt accession number alcc12); *Aspergillus fumigatus* (SwissProt accession number Q4WW45); *Aspergillus niger* (Uniprot accession number Q96WX9); *Aspergillus terreus* (SwissProt accession number Q0CJP9); *Humicola insolens* (WO 2010/014706); *Penicillium aurantiogriseum* (WO 2009/068565); *Talaromyces emersonii* (UniProt accession number Q8X211); and *Trichoderma reesei* (Uniprot accession number Q99024).

The polypeptides having enzyme activity used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, Calif., 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

The compositions may be a fermentation broth formulation or a cell composition, as described herein. In some embodiments, the composition is a cell-killed whole broth containing organic acid(s), killed cells and/or cell debris, and culture medium.

In one aspect, the present invention relates to a whole broth formulation or cell culture composition comprising one or more (e.g., several) enzymes having cellulolytic and/or hemicellulolytic activity and a polypeptide having catalase activity.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid (s), and optionally further contains killed cells and/or cell debris. In one embodiment, the killed cells and/or cell debris are removed from a cell-killed whole broth to provide a composition that is free of these components.

The fermentation broth formulations or cell compostions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions may be produced by a method described in WO 90/15861 or WO 2010/096673.

In one aspect, the present invention relates to use of the enzyme composition of the present invention in degrading or converting a cellulosic material.

Fermentation. The fermentable sugars obtained from the hydrolyzed cellulosic material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida, Kluyveromyces*, and *Saccharomyces*, e.g., *Candida sonorensis, Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans; Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala; Klebsiella*, such as *K. oxytoca; Kluyveromyces*, such as *K. marxianus, K. lactis, K. thermotolerans*, and *K. fragilis; Schizosaccharomyces*, such as *S. pombe; Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermo-*

*tolerans.* In another preferred aspect, the yeast is a *Pachysolen.* In another more preferred aspect, the yeast is *Pachysolen tannophilus.* In another preferred aspect, the yeast is a *Pichia.* In another more preferred aspect, the yeast is a *Pichia stipitis.* In another preferred aspect, the yeast is a *Saccharomyces* spp. In another more preferred aspect, the yeast is *Saccharomyces cerevisiae.* In another more preferred aspect, the yeast is *Saccharomyces distaticus.* In another more preferred aspect, the yeast is *Saccharomyces uvarum.*

In a preferred aspect, the bacterium is a *Bacillus.* In a more preferred aspect, the bacterium is *Bacillus coagulans.* In another preferred aspect, the bacterium is a *Clostridium.* In another more preferred aspect, the bacterium is *Clostridium acetobutylicum.* In another more preferred aspect, the bacterium is *Clostridium phytofermentans.* In another more preferred aspect, the bacterium is *Clostridium thermocellum.* In another more preferred aspect, the bacterium is *Geobacillus* sp. In another more preferred aspect, the bacterium is a *Thermoanaerobacter.* In another more preferred aspect, the bacterium is *Thermoanaerobacter saccharolyticum.* In another preferred aspect, the bacterium is a *Zymomonas.* In another more preferred aspect, the bacterium is *Zymomonas mobilis.*

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis.* In another preferred aspect, the genetically modified fermenting microorganism is *Escherichia coli.* In another preferred aspect, the genetically modified fermenting microorganism is *Klebsiella oxytoca.* In another preferred aspect, the genetically modified fermenting microorganism is *Kluyveromyces marxianus.* In another preferred aspect, the genetically modified fermenting microorganism is *Saccharomyces cerevisiae.* In another preferred aspect, the genetically modified fermenting microorganism is *Zymomonas mobilis.*

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation products: A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, Biotechnology and Bioengineering 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is polyketide.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Polypeptides Having Catalase Activity

In the methods of the present invention, the polypeptide having catalase activity can be any polypeptide having catalase activity. The polypeptide having catalase activity may be present as an enzyme in the enzyme composition and/or as one or more protein components added to the composition. In a preferred aspect, the polypeptide having catalase activity is foreign to one or more components of the cellulolytic enzyme composition.

The polypeptide having catalase activity may be obtained from microorganisms of any genus. In one aspect, the polypeptide obtained from a given source is secreted extracellularly.

The polypeptide having catalase activity may be a bacterial polypeptide. For example, the polypeptide may be a gram positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, or *Oceanobacillus* polypeptide having catalase activity, or a Gram negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having catalase activity.

In one aspect, the polypeptide having catalase activity is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having catalase activity.

In another aspect, the polypeptide having catalase activity is a *Streptococcus equisimilis, Streptococcus pyogenes, Streptococcus uberis,* or *Streptococcus equi* subsp. *Zooepidemicus* polypeptide having catalase activity.

In another aspect, the polypeptide having catalase activity is a *Streptomyces achromogenes, Streptomyces avermitilis, Streptomyces coelicolor, Streptomyces griseus,* or *Streptomyces lividans* polypeptide having catalase activity.

The polypeptide having catalase activity may also be a fungal polypeptide, and more preferably a yeast polypeptide such as a *Candida, Kluyveromyces, Pichia, Saccharomyces, Schizosaccharomyces,* or *Yarrowia* polypeptide having catalase activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having catalase activity.

In another aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis* polypeptide having catalase activity.

In another aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium emersonii, Penicillium funiculosum, Penicillium purpurogenum, Phanerochaete chrysosporium, Talaromyces stipitatus, Thermoascus aurantiacus, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* polypeptide having catalase activity.

In a preferable embodiment, the polypeptide having catalase activity is a catalase from *Thermoascus, Talaromyces, Humicola,* or *Penicillium*. In a more preferable embodiment, the polypeptide having catalase activity is a catalase from *Thermoascus aurantiacus, Talaromyces stipitatus, Humicola insolens,* or *Penicillium emersonii*.

Non-limiting examples of suitable catalases and coding sequence thereof are listed below.

SEQ ID NOs: 1 and 2: a polynucleotide and a polypeptide of a catalase from *Thermoascus aurantiacus*, as described in JP 2004261137A.

SEQ ID NOs: 3 and 4: a polynucleotide and a polypeptide of a catalase from *Talaromyces stipitatus*, which can be prepared as shown in Examples 9-13.

SEQ ID NOs: 5 and 6: a polynucleotide and a polypeptide of a catalase from *Humicola insolens*, which can be prepared as shown in Examples 14-20.

SEQ ID NOs: 7 and 8: a polynucleotide and a polypeptide of a catalase from *Penicillium emersonii*, which can be prepared as shown in Examples 21-27.

SEQ ID NOs: 9 and 10: a polynucleotide and a polypeptide of a catalase from *Thermus Brockianus*, as described in WO 2005/044994.

SEQ ID NOs: 11 and 12: a polynucleotide and a polypeptide of a catalase from *Saccharomyces pastorianus*, as described in WO 2007/105350.

SEQ ID NOs: 13 and 14: a polynucleotide and a polypeptide of a catalase from *Saccharomyces pastorianus* as described in WO 2007/105350.

SEQ ID NOs: 15 and 16: a polynucleotide and a polypeptide of a catalase from *Penicillium pinophilum*, as described in WO 2009/104622.

SEQ ID NOs: 17 and 18: a polynucleotide and a polypeptide of a catalase from *Humicola grisea*, as described in WO 2009/104622.

SEQ ID NOs: 19 and 20: a polynucleotide and a polypeptide of a catalase from *Thielavia terrestris*, as described in WO 2010/074972.

SEQ ID NOs: 21 and 22: a polynucleotide and a polypeptide of a catalase from *Bacillus thermoglucosidasius*, as described in JP 11243961A.

SEQ ID NOs: 23 and 24: a polynucleotide and a polypeptide of a catalase from *Aspergillus oryzae*, as described in JP 2002223772A.

SEQ ID NOs: 25 and 26: a polynucleotide and a polypeptide of a catalase from *Thermoascus aurantiacus*, as described in JP 2007143405A.

SEQ ID NOs: 27 and 28: a polynucleotide and a polypeptide of a catalase from *Bacillus thermoglucosidasius*, as described in U.S. Pat. No. 6,022,721.

SEQ ID NOs: 29 and 30: a polynucleotide and a polypeptide of a catalase from *Bacillus thermoglucosidasius*, as described in U.S. Pat. No. 6,022,721.

SEQ ID NOs: 31 and 32: a polynucleotide and a polypeptide of a catalase from *Alcaligenes aquamarinus*, as described in WO 98/00526.

SEQ ID NOs: 33 and 34: a polynucleotide and a polypeptide of a catalase from *Microscilla furvescens*, as described in WO 98/00526.

SEQ ID NOs: 35 and 36: a polynucleotide and a polypeptide of a catalase from *Aspergillus niger*, as described in U.S. Pat. No. 5,360,901.

SEQ ID NO 37: a polypeptide of *Humicola grisea* thermotolerant catalase (GENESEQP: AXQ55105, disclosed in WO2009104622).

In an embodiment, the catalases used in the present invention have a sequence identity to the mature polypeptide of the mature polypeptide of SEQ ID NO: 2, the mature polypeptide of SEQ ID NO: 4, the mature polypeptide of SEQ ID NO: 6, the mature polypeptide of SEQ ID NO: 8, the mature polypeptide of SEQ ID NO: 10, the mature polypeptide of SEQ ID NO: 12, the mature polypeptide of SEQ ID NO: 14, the mature polypeptide of SEQ ID NO: 16, the mature polypeptide of SEQ ID NO: 18, the mature polypeptide of SEQ ID NO: 20, the mature polypeptide of SEQ ID NO: 22, the mature polypeptide of SEQ ID NO: 24, the mature polypeptide of SEQ ID NO: 26, the mature polypeptide of SEQ ID NO: 28, the mature polypeptide of SEQ ID NO: 30, the mature polypeptide of SEQ ID NO: 32, the mature polypeptide of SEQ ID NO: 34, the mature polypeptide of SEQ ID NO: 36, the mature polypeptide of SEQ ID NO: 37, of at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have catalase activity.

In one embodiment, the mature polypeptide is amino acids 1 to 746 of SEQ ID NO: 2. In another aspect, the mature polypeptide is amino acids 20 to 733 of SEQ ID NO: 4 based on the SignalP program that predicts amino acids 1 to 19 of SEQ ID NO: 4 are a signal peptide. In another aspect, the mature polypeptide is amino acids 20 to 765 of SEQ ID NO: 6 based on the SignalP program that predicts amino acids 1 to 19 of SEQ ID NO: 6 are a signal peptide. In another aspect, the mature polypeptide is amino acids 20 to 741 of SEQ ID NO: 8 based on the SignalP program that predicts amino acids 1 to 19 of SEQ ID NO: 8 are a signal peptide. It is known in the art that a host cell may produce a mixture of two of more different mature polypeptides (i.e., with a different C-terminal and/or N-terminal amino acid) expressed by the same polynucleotide.

In another embodiment, the catalases used in the present invention are encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1, the mature polypeptide coding sequence of SEQ ID NO: 3, the mature polypeptide coding sequence of SEQ ID NO: 5, or the mature polypeptide coding sequence of SEQ ID NO: 7, (ii) the cDNA sequence thereof, or (iii) the full-length complement of (i) or (ii) (Sambrook et al., 1989, Molecular Cloning, A Laboratory Manual, 2d edition, Cold Spring Harbor, N.Y.).

For purposes of the present invention, hybridization indicates that the polynucleotide hybridizes to a labeled nucleic acid probe corresponding to (i) SEQ ID NO: 1, SEQ ID NO: 3, SEQ ID NO: 5, or SEQ ID NO: 7; (ii) the mature polypeptide coding sequence of SEQ ID NO: 1, the mature polypeptide coding sequence of SEQ ID NO: 3, the mature polypeptide coding sequence of SEQ ID NO: 5, or the mature polypeptide coding sequence of SEQ ID NO: 7; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In an embodiment, the catalases used in the present invention are encoded by a polynucleotide having at least 60%, e.g., at least 65%, at least 70%, at least 75%, at least 78%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1, the mature polypeptide coding sequence of SEQ ID NO: 3, the mature polypeptide coding sequence of SEQ ID NO: 5, or the mature polypeptide coding sequence of SEQ ID NO: 7; or the cDNA sequence thereof.

In one embodiment, the mature polypeptide coding sequence is nucleotides 1 to 2351 of SEQ ID NO: 1 or the cDNA sequence thereof. In another embodiment, the mature polypeptide coding sequence is nucleotides 58 to 2418 of SEQ ID NO: 3 or the cDNA sequence thereof based on the SignalP program that predicts nucleotides 1 to 57 of SEQ ID NO: 3 encode a signal peptide. In another embodiment, the mature polypeptide coding sequence is nucleotides 58 to 3040 of SEQ ID NO: 5 or the cDNA sequence thereof based on the SignalP program that predicts nucleotides 1 to 57 of SEQ ID NO: 5 encode a signal peptide. In another embodiment, the mature polypeptide coding sequence is nucleotides 58 to 2476 of SEQ ID NO: 7 or the cDNA sequence thereof based on the SignalP program that predicts nucleotides 1 to 57 of SEQ ID NO: 7 encode a signal peptide.

In another embodiment, the catalases used in the present invention relates to variants of the mature polypeptide of SEQ ID NO: 2, variants of the mature polypeptide of SEQ ID NO: 4, variants of the mature polypeptide of SEQ ID NO: 6, or variants of the mature polypeptide of SEQ ID NO: 8, comprising a substitution, deletion, and/or insertion at one or more (e.g., several) positions. In an embodiment, the number of amino acid substitutions, deletions and/or insertions introduced into the mature polypeptide of SEQ ID NO: 2, the mature polypeptide of SEQ ID NO: 4, the mature polypeptide of SEQ ID NO: 6, or the mature polypeptide of SEQ ID NO: 8 is up to 10, e.g., 1, 2, 3, 4, 5, 6, 7, 8, 9 or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for catalase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Examples of commercial catalase preparations suitable for use in the present invention include, for example, Terminox Ultra 50L/200L (Novozymes A/S), Catazyme 25L (Novozymes A/S), GC118 (Danisco A/S), Oxygone T100/T400 (Danisco A/S), ASC Super 200L (Mitsubishi Chemicals, Japan), and Reyonet 200L (Nagase, Japan).

Nucleic Acid Constructs

An isolated polynucleotide encoding a polypeptide, e.g., a cellulolytic enzyme, a polypeptide having catalase activity, a polypeptide having cellulolytic enhancing activity, etc., may be manipulated in a variety of ways to provide for expression of the polypeptide by constructing a nucleic acid construct comprising an isolated polynucleotide encoding the polypeptide operably linked to one or more (e.g., several) control sequences that direct the expression of the coding sequence in a suitable host cell under conditions compatible with the control sequences. A polynucleotide may be manipulated in a variety of ways to provide for expression of the polypeptide. Manipulation of the polynucleotide prior to its insertion into a vector may be desirable or necessary depending on the expression vector. The techniques for modifying polynucleotide sequences utilizing recombinant DNA methods are well known in the art.

The control sequence may be a promoter, a polynucleotide that is recognized by a host cell for expression of a polynucleotide encoding a polypeptide. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, Gene 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease Useful polyadenylation sequences for yeast host cells are described by Guo and Sherman, 1995, *Mol. Cellular. Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The various nucleotide and control sequences described above may be joined together to produce a recombinant expression vector that may include one or more (e.g., several) convenient restriction sites to allow for insertion or substitution of a polynucleotide encoding a polypeptide, e.g., a cellulolytic enzyme, a polypeptide having catalase activity, a polypeptide having cellulolytic enhancing activity, etc., at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

Host Cells

Recombinant host cells comprising a polynucleotide encoding a polypeptide, e.g., a cellulolytic enzyme, a polypeptide having catalase activity, a polypeptide having cellulolytic enhancing activity, etc., can be advantageously used in the recombinant production of the polypeptide. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide, e.g., a prokaryote or a eukaryote.

The prokaryotic host cell may be any Gram-positive or Gram-negative bacterium. Gram-positive bacteria include, but not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), using competent cells transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation and electroporation (see, e.g., Gong et al., 2004, *Folia Microbiol.* (Praha) 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, Appl. Environ. Microbiol. 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell. "Fungi" as used herein includes the phyla *Ascomycota, Basidiomycota, Chytridiomycota*, and *Zygomycota* as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

Methods for producing a polypeptide, e.g., a cellulolytic enzyme, a polypeptide having catalase activity, a polypeptide having cellulolytic enhancing activity, etc., comprise (a) cultivating a cell, which in its wild-type form produces the polypeptide, under conditions conducive for production of the polypeptide; and (b) recovering the polypeptide. In a preferred aspect, the cell is an *Aspergillus, Thermoascus, Talaromyces, Trichoderma, Humicola*, or *Penicillium* cell. In a more preferred aspect, the cell is an *Aspergillus niger, Aspergillus oryzae, Aspergillus fumigatus, Thermoascus aurantiacus, Talaromyces stipitatus, Trichoderma reesei, Humicola insolens*, or *Penicillium emersonii* cell.

Alternatively, methods for producing a polypeptide, e.g., a cellulolytic enzyme, a polypeptide having catalase activity, a polypeptide having cellulolytic enhancing activity, etc., comprise (a) cultivating a recombinant host cell under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide. The polypeptides having cellulolytic enhancing activity are detected using the methods described herein.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, the whole fermentation broth is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell expressing a polypeptide is used as a source of the polypeptide.

The present invention is further described by the following examples that should not be construed as limiting the scope of the invention.

EXAMPLES

Strain

The fungal strain NN70 was obtained from Centraalbureau voor Schimmelcultures named as CBS 375.48. The strain NN70 was identified as *Talaromyces stipitatus*, based on both morphological characteristics and ITS rDNA sequence.

The fungal strain NN38 was isolated from a soil sample collected from China by the dilution plate method with PDA medium at 45° C. It was then purified by transferring a single conidium onto a YG agar plate. The strain NN38 was identified as *Humicola insolens*, based on both morphological characteristics and ITS rDNA sequence.

The fungal strain NN051602 was isolated from a compost sample collected from China by the dilution plate method with PDA medium at 45° C. It was then purified by transferring a single conidium onto a YG agar plate. The strain NN051602 was identified as *Penicillium emersonii*, based on both morphological characteristics and ITS rDNA sequence.

Media

PDA medium was composed of 39 grams of potato dextrose agar and deionized water to 1 liter.

YG agar plate was composed of 5.0 g of yeast extract, 10.0 g of glucose, 20.0 g of agar, and deionized water to 1 liter.

YPM medium contained 1% yeast extract, 2% of peptone, and 2% of maltose in deionized water.

YPG medium contained 0.4% of yeast extract, 0.1% of $KH_2PO_4$, 0.05% of $MgSO_4.7H_2O$, 1.5% glucose in deionized water.

Minimal medium plates were composed of 342 g of sucrose, 20 ml of salt solution, 20 g of agar, and deionized water to 1 liter. The salt solution was composed of 2.6% KCl, 2.6% $MgSO_4.7H_2O$, 7.6% $KH_2PO_4$, 2 ppm $Na_2B_4O_7.10H_2O$, 20 ppm $CuSO_4.5H_2O$, 40 ppm $FeSO_4.7H_2O$, 40 ppm $MnSO_4.2H_2O$, 40 ppm $Na_2MoO_4.2H_2O$, and 400 ppm $ZnSO_4.7H_2O$.

Example 1

Boosting Effect of *Thermoascus aurantiacus* Catalase or *Talaromyces stipitatus* Catalase on Hydrolysis of Pretreated Corn Stover (PCS)

Catalase from *Thermoascus aurantiacus* (as shown in SEQ ID NO: 2) was expressed by *Aspergillus niger* and purified as described in J.P. Publication 2004261137A. Catalase from *Talaromyces stipitatus* (as shown in SEQ ID NO: 4) was cloned, expressed and purified as Examples 9-13. Corn stover was pretreated at the U.S. Department of Energy National Renewable Energy Laboratory (NREL) using dilute sulfuric acid at conditions of 190° C., 1 minute residence time, 0.05 g acid/g dry biomass, and at a 30% total solid concentration in a pretreatment reactor.

PCS was hydrolyzed at an initial total solid (TS) of 10% and total weight of hydrolysis system of 20 g. *Trichoderma reesei* cellulase composition (CELLIC® CTec2 available from Novozymes A/S, Bagsvaerd, Denmark) was added into the PCS for enzymatic hydrolysis with a ratio of the *Trichoderma reesei* cellulase composition to cellulose of 0.5% (w/w), namely 5 mg/g cellulose based on protein amount. *Thermoascus aurantiacus* catalase or *Talaromyces stipitatus* catalase at dosages shown in Table 1 below was added into the hydrolysis system. The hydrolysis system without the addition of catalase was used as a control. The flasks were incubated at 50° C. for 72 hours, with shaking at 130 rpm. Unless specified otherwise, the total hydrolysis time was 72 hours. After hydrolysis was completed, the sugar was analyzed by High Performance Liquid Chromatography (HPLC).

For HPLC measurement, the collected samples were filtered using 0.22 μm syringe filters (Millipore, Bedford, Mass., USA) and the filtrates were analyzed for sugar content as described below. The sugar concentrations of samples diluted in 0.005 M $H_2SO_4$ were measured using a 7.8×300 mm AMINEX® HPX-87H column (Bio-Rad Laboratories, Inc., Hercules, Calif., USA) by elution with 0.005 M $H_2SO_4$ at 65° C. at a flow rate of 0.7 ml per minute, and quantification by integration of the glucose signal from refractive index detection (CHEMSTATION®, AGILENT® 1100 HPLC, Agilent Technologies, Santa Clara, Calif., USA) calibrated by pure sugar samples. The resultant glucose was used to calculate the percentage of glucose yield from glucans for each reaction. Measured sugar concentrations were adjusted for the appropriate dilution factor. The net concentrations of enzymatically-produced sugars were determined by adjusting the measured sugar concentrations for corresponding background sugar concentrations in unwashed biomass at zero time point. All HPLC data processing was performed using MICROSOFT EXCEL™ software (Microsoft, Richland, Wash., USA).

The degree of glucose conversion to glucose was calculated according to the publication by Zhu, Y., et al. 2010. *Bioresource Technology*. 102(3): 2897-2903.

The results as shown in Table 1 demonstrated that PCS conversion to glucose can be improved significantly by adding small amounts of catalase.

TABLE 1

Effect of catalase from *T. aurantiacus* or catalase from *T. stipitatus* on the glucose conversion of PCS

| | Dosage of catalase (μg/g cellulose) | | | | | | |
|---|---|---|---|---|---|---|---|
| | | *T. aurantiacus* catalase | | | *T. stipitatus* catalase | | |
| | 0 (control) | 50 | 250 | 500 | 50 | 250 | 500 |
| Glucose conversion (%) | 49.7 ± 0.4 | 54.9 ± 0.1 | 61.7 ± 1.8 | 63 ± 0.7 | 56.7 ± 0.4 | 60.6 ± 1.9 | 60.4 ± 2.5 |

Example 2

Boosting Effect of *Talaromyces stipitatus* Catalase on Mono-components of Cellulases Avicel® PH-101 (Fluka 11365, Sigma-Aldrich (Shanghai), Shanghai, China), a kind of microcrystalline cellulose, was hydrolyzed at a final concentration of 5 g/l and total volume of the hydrolysis system of 0.5 ml. The pH was adjusted and kept at 5.0 by 50 mM sodium acetate. In addition, ascorbic acid was present with a final concentration of 5 mM or absent in the hydrolysis system. Manganese (II) sulfate was present with a final concentration of 1 mM in the hydrolysis system.

Cellobiohydrolase (CBH) I from *Aspergillus fumigatus* (WO 2011/057140), cellobiohydrolase (CBH) II from *Aspergillus fumigatus* (WO 2011/057140), endoglucanase (EG) I from *Trichoderma reesei* (WO 2011/057140) and beta-glucanase (BG) from *Aspergillus oryaze* (WO 02/095014) were cloned, expressed and purified. These mono-components were applied to the hydrolysis of Avicel® individually. 10 mg mono-component of cellulase/g Avicel® and 5 mg catalase/g Avicel® were used. The tubes were incubated at 50° C. for 72 hours, with shaking at 600 rpm. All experiments were performed in triplicates.

HPLC analysis of the extent of hydrolysis was performed according to the procedure described in Example 1.

The extent of cellulose conversion was calculated based on the mass ratio of solubilized glucosyl units to the initial mass of insoluble cellulose. Only glucose and cellobiose were measured for soluble sugars, as cellodextrins longer than cellobiose were present in negligible concentrations (due to enzymatic hydrolysis). The extent of total cellulose conversion was calculated using the following equation:

$$\% \text{ conversion} = \frac{[\text{cellobiose}](\text{mg/ml})/1.053 + ([\text{glucose}][\text{mg/ml})/1.111)}{[\text{Cellulose}](\text{mg/ml})} \times 100 \quad \text{(Equation 1)}$$

The 1.111 and 1.053 factors for glucose and cellobiose, respectively, take into account the increase in mass when the glucosyl units in cellulose (average molecular mass of 162 daltons) are converted to glucose (molecular mass of 180 daltons) or cellobiose glucosyl units (average molecular mass of 171 daltons).

As shown in Table 2, in the presence of ascorbic acid, the hydrolysis of every mono-component of cellulase can be boosted by *T. stipitatus* catalase.

Example 3

Boosting Effect of *Humicola insolens* Catalase on Hydrolysis of PCS

Preparation of PCS and set-up of hydrolysis system were the same as example 1. Catalase from *Humicola insolens* was cloned, expressed and purified as shown in Examples 14-20.

PCS was hydrolyzed at an initial TS of 10% and total weight of hydrolysis system of 20 g. *Trichoderma reesei* cellulase composition (CELLIC® CTec2 available from Novozymes A/S, Bagsvaerd, Denmark) was utilized for enzymatic hydrolysis. Five percent by weight Ctec2 was replaced by *H. insolens* catalase based on protein amount and the total enzyme dose was 4 mg/g cellulose. The hydrolysis system with 4 mg *Trichoderma reesei* cellulase composition/g cellulose but without catalase was used as a control. The flasks were incubated at 50° C. for 72 hours, with shaking at 130 rpm. The total hydrolysis time was 72 hours.

The calculation of glucose conversion was the same as example 1 and the boosting effect was shown in table 3.

TABLE 3

Effect of catalase from *Humicola insolens* on glucose conversion of PCS.

|  | Control | *H. insolens* Catalase |
|---|---|---|
| Glucose conversion (%) | 50.4 ± 1.1 | 58.4 ± 0.9 |

Example 4

Boosting Effect of *Humicola insolens* Catalase on Hydrolysis of PCS

Preparation of PCS and set-up of hydrolysis system were the same as example 1. Catalase from *Humicola insolens* was cloned, expressed and purified and purified as shown in Examples 14-20.

PCS was hydrolyzed at an initial TS of 10% and total weight of hydrolysis system of 20 g. *Trichoderma reesei* cellulase composition (CELLIC® CTec3 available from Novozymes A/S, Bagsvaerd, Denmark) was utilized for enzymatic hydrolysis. Five percent by weight Ctec3 was replaced by *H. insolens* catalase based on protein amount and the total enzyme dose was 4 mg/g cellulose. The hydrolysis system with 4 mg *Trichoderma reesei* cellulase composition/g cellulose but without catalase was used as a control. The flasks were incubated at 50° C. for 72 hours, with shaking at 130 rpm. The total hydrolysis time was 72 hours.

TABLE 2

Effect of catalase from *T. stipitatus* on glucose conversion of Avicel.

| | Mono-component without Ascorbic acid | | | | | Mono-component with Ascorbic acid | | | | |
|---|---|---|---|---|---|---|---|---|---|---|
| | Control | BG | CBH I | CBH II | EG | Control | BG | CBH I | CBH II | EG |
| Control (%) | 0.0 ± 0.0 | 0.0 ± 0.0 | 13.7 ± 0.2 | 9.0 ± 0.3 | 2.5 ± 0.0 | 0.0 ± 0.0 | 0.0 ± 0.0 | 11.4 ± 0.1 | 8.0 ± 0.3 | 1.9 ± 0.1 |
| Catalase (%) | 0.0% ± 0.0 | 0.0 ± 0.0 | 13.4 ± 0.2 | 9.1 ± 0.1 | 2.4 ± 0.1 | 0.0 ± 0.0 | 2.4 ± 0.3 | 15.8 ± 1.3 | 12.7 ± 0.3 | 4.8 ± 0.0 |

The calculation of glucose conversion was the same as example 1 and the boosting effect was shown in table 4.

TABLE 4

Effect of catalase from *Humicola insolens* on glucose conversion of PCS.

|  | Control | *H. insolens* Catalase |
|---|---|---|
| Glucose conversion (%) | 70.9 ± 1.4 | 80.1 ± 1.2 |

Example 5

Synergetic Effect of *Thermoascus aurantiacus* Catalase and *Thermoascus aurantiacus* GH61A on Hydrolysis of PCS PCS was prepared according to the procedure as described in Example 1, and hydrolyzed at initial TS of 10% and total weight of hydrolysis system of 20 g. The pH was adjusted to 5.0 using 10 M sodium hydroxide. *Trichoderma reesei* cellulase composition (CELLUCLAST®) in the presence of 10% of total protein weight *Aspergillus fumigatus* beta-glucosidase (WO 2005/047499), available from Novozymes A/S, Bagsvaerd, Denmark) was added into PCS for enzymatic hydrolysis with a ratio of the *Trichoderma reesei* cellulase composition to cellulose of 0.8% (w/w). Catalase from *Thermoascus aurantiacus*, GH61A polypeptide from *Thermoascus aurantiacus* (WO 2005/074656), or the combination thereof were added into the hydrolysis system, respectively. The dosage of catalase, GH61A polypeptide, or the combination thereof was calculated based on the weight of cellulose. The hydrolysis system with *Trichoderma reesei* cellulase composition but without catalase and GH61 was used as a control. The flasks were incubated at 50° C. for 72 hours, with shaking at 130 rpm. All experiments were performed in triplicates. HPLC analysis of the extent of hydrolysis was performed according to the procedure described in Example 1. The conversion of PCS to glucose after 72-hour hydrolysis was shown in Table 5 below.

TABLE 5

Synergetic effect of *Thermoascus aurantiacus* catalase and *Thermoascus aurantiacus* GH61A on hydrolysis of PCS

|  | Control | Catalase alone (μg/g cellulose) | | GH61A alone (μg/g cellulose) | | Catalase + GH61A (μg/g cellulose) | |
|---|---|---|---|---|---|---|---|
|  |  | 80 | 160 | 80 | 160 | 80 + 80 | 160 + 160 |
| Glucose conversion (%) | 66.9 ± 1.1 | 75.9 ± 0.0 | 82.8 ± 0.4 | 70.6 ± 0.2 | 71.8 ± 0.2 | 88.7 ± 3.0 | 93.2 ± 0.8 |

As shown in Table 5, catalase or GH61A polypeptide alone boosted the hydrolysis of PCS. It was surprisingly found that, when catalase and GH61A polypeptide were used simultaneously, the hydrolysis was improved significantly. The results indicated that catalase and GH61A polypeptide have a significant synergistic effect on the hydrolysis of PCS.

Example 6

Boosting Effect of *Penicillium emersonii* Catalase on Hydrolysis of PCS

Preparation of PCS and set-up of hydrolysis system were the same as example 1. Catalase from *P. emersonii* was cloned, expressed and purified as shown in Examples 21-27.

PCS was hydrolyzed at an initial TS of 10% and total weight of hydrolysis system of 20 g. *Trichoderma reesei* cellulase composition (CELLIC® CTec2 available from Novozymes A/S, Bagsvaerd, Denmark) was added into PCS for enzymatic hydrolysis. Five percent by weight of Ctec2 was replaced with *P. emersonii* catalase based on protein amount and the total enzyme dose was 4 mg/g cellulose. The hydrolysis system with *Trichoderma reesei* cellulase composition but without catalase was used as a control. The flasks were incubated at 50° C. for 72 hours, with shaking at 130 rpm.

The calculation of glucose conversion was the same as example 1 and the boosting effect was shown in table 6.

TABLE 6

Effect of catalase from *P. emersonii* on glucose conversion of PCS.

|  | Control | *P. emersonii* Catalase |
|---|---|---|
| Glucose conversion (%) | 48.6 ± 0.7 | 54.3 ± 0.8 |

Example 7

Boosting effect of *Thermoascus aurantiacus* Catalase on Hydrolysis of PCS in Relatively high TS Preparation of PCS and set-up of hydrolysis system were the same as example 1. PCS was hydrolyzed at an initial TS of 20% and total weight of hydrolysis system of 20 g. *Trichoderma reesei* cellulase composition (CELLIC® CTec2 available from Novozymes A/S, Bagsvaerd, Denmark) was added into PCS for enzymatic hydrolysis. Five percent by weight of Ctec2 was replaced by *T. aurantiacus* catalase based on protein amount and the total enzyme dose was 7 mg/g cellulose. The hydrolysis system with *Trichoderma reesei* cellulase composition but without catalase was used as a control. The flasks were incubated at 50° C. for 72 hours, with shaking at 130 rpm. The calculation of glucose conversion was the same as example 1 and the boosting effect of catalases was shown in table 7.

TABLE 7

Effect of catalase from *Thermoascus aurantiacus* on glucose conversion of PCS.

| | Control | 5% *T. aurantiacus* catalase replacement |
|---|---|---|
| Glucose conversion (%) | 58.6 ± 1.4 | 64.8 ± 0.8 |

Example 8

**Boosting Effect of *Thermoascus aurantiacus* Catalase on Hydrolysis of PCS in Relatively High TS**

Preparation of PCS and set-up of hydrolysis system were the same as example 1. PCS was hydrolyzed at an initial TS of 20% and total weight of hydrolysis system of 20 g. *Trichoderma reesei* cellulase composition (CELLIC® CTec3 available from Novozymes A/S, Bagsvaerd, Denmark) was utilized for enzymatic hydrolysis. Five percent by weight of Ctec3 was replaced by *T. aurantiacus* catalase based on protein amount and the total enzyme dose was 6 mg/g cellulose. The hydrolysis system with *Trichoderma reesei* cellulase composition but without catalase was used as a control. The flasks were incubated at 50° C. for 72 hours, with shaking at 130 rpm.

The calculation of glucose conversion was the same as example 1 and the boosting effect of catalases was shown in table 8.

TABLE 8

Effect of catalase from *Thermoascus aurantiacus* on glucose conversion of PCS.

| | Control | 5% *T. aurantiacus* catalase replacement |
|---|---|---|
| Glucose conversion (%) | 72.0± | 80.5 ± 0.8 |

Example 9

Talaromyces stipitatus Genomic DNA Extraction

*Talaromyces stipitatus* strain NN70 was grown in PDA agar plate at 45° C. for 3 days. Mycelia were collected directly from the agar plate into a sterilized mortar and frozen under liquid nitrogen. Frozen mycelia were ground, by mortar and pestle, to a fine powder, and genomic DNA was isolated using a DNeasy® Plant Mini Kit (QIAGEN Inc., Valencia, Calif., USA).

Example 10

**Cloning of the *Talaromyces stipitatus* Catalase Gene from Genomic DNA**

Based on the DNA information of European Molecular Biology Laboratory (EMBL):EQ962660 SEQ ID NO: 3) and protein sequence SWISSPROT:B8MT74 (i.e., SEQ ID NO: 4), oligonucleotide primers, shown in below, were designed to amplify the catalase gene from the genomic DNA of *Talaromyces stipitatus* NN70. Primers were fabricated by Invitrogen (Invitrogen, Beijing, China).

Forward primer:
(SEQ ID NO: 38)
5' ACACAACTGGGGATCC ACC atgcgaggggcatactctctc 3'

Reverse primer:
(SEQ ID NO: 39)
5' GTCACCCTCTAGATCT aacaagttactcgtgttaatcgtggaa 3'

Lowercase characters represent the sequences of the gene, while capitalized parts were homologous to the insertion sites of pPFJO355 vector which has been described in US2010306879.

The expression vector pPFJO355 contains the TAKA-amylase promoter derived from *Aspergillus oryzae* and the *Aspergillus niger* glucoamylase terminator elements. Furthermore pPFJO355 has pUC18 derived sequences for selection and propagation in *E. coli*, and a pyrG gene, which encodes an orotidine decarboxylase derived from *Aspergillus nidulans* for selection of a transformant of a pyrG mutant *Aspergillus* strain.

Twenty picomoles of primer pair (forward and reverse) were used in a PCR reaction composed of 2 µl of *Talaromyces stipitatus* NN70 genomic DNA, 10 µl of 5×GC Buffer, 1.5 µl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 µl. The amplification was performed using a Peltier Thermal Cycler (MJ Research Inc., South San Francisco, Calif., USA) programmed for denaturing at 98° C. for 40 seconds; 8 cycles of denaturing at 98° C. for 15 seconds, annealing at 70° C. for 30 seconds, with 1° C. decrease per cycle and elongation at 72° C. for 80 seconds; and another 23 cycles each at 98° C. for 15 seconds, 62° C. for 30 seconds and 72° C. for 80 seconds; final extension at 72° C. for 5 minutes. The heat block then went to a 4° C. soak cycle.

The PCR reaction products were isolated by 1.0% agarose gel electrophoresis using 90 mM Tris-borate and 1 mM EDTA (TBE) buffer where a single product band of the expected size, approximate 2.4 kb, was visualized under UV light, and then purified from solution using an ILLUSTRA™ GFX™ PCR DNA and Gel Band Purification Kit (GE Healthcare, Buckinghamshire, UK) according to the manufacturer's instructions.

Plasmid pPFJO355 was digested with Bam HI and Bgl II, isolated by 1.0% agarose gel electrophoresis using TBE buffer, and purified using an ILLUSTRA™ GFX™ PCR DNA and Gel Band Purification Kit according to the manufacturer's instructions.

An IN-FUSION™ CF Dry-down Cloning Kit (Clontech Laboratories, Inc., Mountain View, Calif., USA) was used to clone the fragment directly into the expression vector pPFJO355, without the need for restriction digestion and ligation.

The PCR reaction product and the digested vector were ligated together using an IN-FUSION™ CF Dry-down PCR Cloning resulting in plasmid plasmid pTs in which the transcription of *Talaromyces stipitatus* catalase gene was under the control of a promoter from the gene for *Aspergillus oryzae* alpha-amylase. The cloning operation was conducted according to the manufacturer's instruction. In brief, 30 ng of pPFJO355 digested with Bam HI and Bgl II, and 60 ng of the purified *Talaromyces stipitatus* catalase PCR reaction products were added to the reaction vial and resuspended the powder in a final volume of 10 µl with addition of deionized water. The reaction was incubated at 37° C. for 15 minutes and then 50° C. for 15 minutes. Three µl of the reaction products were used to transform *E. coli* TOP10 competent cells (TIANGEN Biotech (Beijing) Co. Ltd., Beijing, China). *E. coli* transformants containing expression constructs were detected by colony PCR which is a method for quick screening of plasmid inserts directly from *E. coli* colonies. Briefly, in the premixed PCR solution aliquot in each PCR tube, including PCR buffer, $MgCl_2$, dNTP and primer pairs for which the PCR fragment generated, a single colony was added by picking up with a sterile tip and twirling the tip in the reaction solution. Normaly 7-10 colonies were screened. After the PCR program, reactions were checked on agarose gel. The colony giving the amplification of expected size was possibly to contain the correct insert. The plasmid DNA was prepared using a QIAprep Spin Miniprep Kit (QIAGEN Inc., Valencia, Calif., USA). The *Talaromyces stipitatus* catalase gene inserted in plasmid pTs was confirmed by DNA sequencing using a 3730XL DNA Analyzers (Applied Biosystems Inc, Foster City, Calif., USA).

Example 11

Expression of *Talaromyces Stipitatus* Catalase Gene in *Aspergillus oryzae*

*Aspergillus oryzae* HowB101 (described in patent WO9535385 example 1) protoplasts were prepared according to the method of Christensen et al., 1988, Bio/Technology 6: 1419-1422. Three µg of plasmid pTs were used to transform *Aspergillus oryzae* HowB101.

The transformation of *Aspergillus oryzae* HowB101 with plasmid pTs yielded about 50 transformants for each transformation. Eight transformants were isolated to individual Minimal medium plates.

Four transformants from each transformation were inoculated separately into 3 ml of YPM in 24-well plate and incubated at 30° C., 150 rpm. After 3 days incubation, 20 µl of supernatant from each culture were analyzed on NuPAGE Novex 4-12% Bis-Tris Gel with 2-(N-morpholino) ethane-sulfonic acid (MES) (Invitrogen Corporation, Carlsbad, Calif., USA) according to the manufacturer's instructions. The resulting gel was stained with INSTANT BLUE™ (Expedeon Ltd., Babraham Cambridge, UK). SDS-PAGE profiles of the cultures showed expression with protein bands detected. The size of major band of the gene was around 92 KD. The expression strain was designated as EXP84.

Example 12

Fermentation of the Expression Strain EXP84

A slant of the expression strain, EXP84, was washed with 10 ml of YPM and inoculated into eight 2-liter flasks containing 400 ml of YPM medium to generate broth for characterization of the enzyme. The culture was harvested on day 3 and filtered using a 0.45 µm DURAPORE Membrane (Millipore, Bedford, Mass., USA).

Example 13

Purification of Recombinant *Talaromyces stipitatus* Catalase from *Aspergillus oryzae* EXP84

3200 ml supernatant of the recombinant strain EXP84 was precipitated with ammonium sulfate (80% saturation) and re-dissolved in 50 ml 20 mM Tris-HCl buffer, pH7.5, then dialyzed against the same buffer and filtered through a 0.45 mm filter, the final volume was 100 ml. The solution was applied to a 40 ml Q SEPHAROSE® Fast Flow column (GE Healthcare, Buckinghamshire, UK) equilibrated in 20 mM Tris-HCl buffer, pH7.5. Fractions eluted with 0.08-0.2M NaCl were collected and further purified on a 40 ml Q SEPHAROSE® Fast Flow column (GE Healthcare, Buckinghamshire, UK) with a linear NaCl gradient (0.14-0.2M). Fractions were evaluated by SDS-PAGE (NP0336BOX, NUPAGE 4-12% BT GEL 1.5MM15W). Fractions containing a band of approximately 92 kDa were pooled. Then the pooled solution was concentrated by ultrafiltration.

Example 14

*Humicola Insolens* Genomic DNA Extraction

*Humicola insolens* strain NN38 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using DNeasy® Plant Maxi Kit (QIAGEN Inc., Valencia, Calif., USA) following the manufacturer's instruction.

Example 15

Genome Sequencing, Assembly and Annotation of *Humicola insolens* Strain NN38

The extracted genomic DNA samples were delivered to Beijing Genome Institute (BGI, Shenzhen, China) for genome sequencing using ILLUMINA® GA2 System (Illumina, Inc., San Diego, Calif., USA). The raw reads were assembled at BGI using program SOAPdenovo (Li et al., 2010, *Genome Research* 20(2): 265-72). The assembled sequences were analyzed using standard bioinformatics methods for gene finding and functional prediction. Briefly, geneID (Parra et al., 2000, *Genome Research* 10(4):511-515) was used for gene prediction. Blastall version 2.2.10 ((Altschul et al., 1990, *J. Mol. Biol.* 215 (3): 403-410; National Center for Biotechnology Information (NCBI), Bethesda, Md., USA) and HMMER version 2.1.1 (National Center for Biotechnology Information (NCBI), Bethesda, Md., USA) were used to predict function based on structural homology. The catalase gene, (SEQ ID NO: 5 for DNA sequence, SEQ ID NO: 6 for protein sequence), was identified directly by analysis of the Blast results. The Agene program (Munch and Krogh, 2006, *BMC Bioinformatics* 7:263) and SignalP program (Nielsen et al., 1997, *Protein Engineering* 10:1-6) were used to identify starting codons. SignalP was further used to predict the signal peptide. Pepstats (European Bioinformatics Institute, Hinxton, Cambridge CB10 1SD, UK) was used to estimate isoelectric point of proteins, and molecular weight.

Example 16

Cloning of the *Humicola insolens* Catalase Gene from Genomic DNA

Based on the DNA information of the *Humicola insolens* catalase, oligonucleotide primers, shown in below, were designed to amplify the catalase gene from the genomic DNA of *Humicola insolens* NN38. Primers were fabricated by Invitrogen (Invitrogen, Beijing, China).

```
Forward primer:
                                      (SEQ ID NO: 40)
5' ACACAACTGGGGATCC ACC atgaacagagtcacgaatctcct cg 3'

Reverse primer:
                                      (SEQ ID NO: 41)
5' GTCACCCTCTAGATCT ggtacaactcccaccctattccttctc 3'
```

Lowercase characters represent the sequences of the gene in the forward primer and the flanking region of the 3' end of the gene in the reverse primer, while capitalized parts were homologous to the insertion sites of pPFJO355 vector which has been described in US2010306879.

The expression vector pPFJO355 contains the TAKA-amylase promoter derived from *Aspergillus oryzae* and the *Aspergillus niger* glucoamylase terminator elements. Furthermore pPFJO355 has pUC18 derived sequences for selection and propagation in *E. coli*, and a pyrG gene, which encodes an orotidine decarboxylase derived from *Aspergillus nidulans* for selection of a transformant of a pyrG mutant *Aspergillus* strain.

Twenty picomoles of primer pair (forward and reverse) were used in a PCR reaction composed of 2 µl of *Humicola insolens* NN38 genomic DNA, 10 µl of 5×GC Buffer, 1.5 µl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 µl. The amplification was performed using a Peltier Thermal Cycler (MJ Research Inc., South San Francisco, Calif., USA) programmed for denaturing at 98° C. for 1 minute; 6 cycles of denaturing at 98° C. for 15 seconds, annealing at 63° C. for 30 seconds, with 1° C. decrease per cycle and elongation at 72° C. for 3 minutes; and another 22 cycles each at 98° C. for 15 seconds, 62° C. for 30 seconds and 72° C. for 3 minutes; final extension at 72° C. for 7 minutes. The heat block then went to a 4° C. soak cycle.

The PCR reaction products were isolated by 1.0% agarose gel electrophoresis using 90 mM Tris-borate and 1 mM EDTA (TBE) buffer where a single product band of the expected size, approximate 3.1 kb, was visualized under UV light and then purified from solution using an ILLUSTRA™ GFX™ PCR DNA and Gel Band Purification Kit (GE Healthcare, Buckinghamshire, UK) according to the manufacturer's instructions.

Plasmid pPFJO355 was digested with Bam HI and Bgl II, isolated by 1.0% agarose gel electrophoresis using TBE buffer, and purified using an ILLUSTRA™ GFX™ PCR DNA and Gel Band Purification Kit according to the manufacturer's instructions.

An IN-FUSION™ CF Dry-down Cloning Kit (Clontech Laboratories, Inc., Mountain View, Calif., USA) was used to clone the fragment directly into the expression vector pPFJO355, without the need for restriction digestion and ligation.

The PCR reaction product and the digested vector were ligated together using an IN-FUSION™ CF Dry-down PCR Cloning resulting in plasmid pHi in which the transcription of *Humicola insolens* catalase gene was under the control of a promoter from the gene for *Aspergillus oryzae* alpha-amylase. The cloning operation was conducted according to the manufacturer's instruction. In brief, 30 ng of pPFJO355 digested with Bam HI and Bgl II, and 60 ng of the purified *Humicola insolens* catalase PCR product were added to the reaction vial and resuspended the powder in a final volume of 10 µl with addition of deionized water. The reaction was incubated at 37° C. for 15 minutes and then 50° C. for 15 minutes. Three µl of the reaction products were used to transform *E. coli* TOP10 competent cells (TIANGEN Biotech (Beijing) Co. Ltd., Beijing, China). *E. coli* transformants containing expression constructs were detected by colony PCR which is a method for quick screening of plasmid inserts directly from *E. coli* colonies. Briefly, in the premixed PCR solution aliquot in each PCR tube, including PCR buffer, $MgCl_2$, dNTP and primer pairs for which the PCR fragment generated, a single colony was added by picking up with a sterile tip and twirling the tip in the reaction solution. Normally 7-10 colonies were screened. After the PCR program, reactions were checked on agarose gel. The colony giving the amplification of expected size was possibly to contain the correct insert. The plasmid DNA was prepared using a QIAprep Spin Miniprep Kit (QIAGEN Inc., Valencia, Calif., USA). The *Humicola insolens* catalase gene inserted in plasmid pHi was confirmed by DNA sequencing using a 3730XL DNA Analyzers (Applied Biosystems Inc, Foster City, Calif., USA).

Example 17

Expression of *Humicola insolens* Catalase Gene in *Aspergillus oryzae*

*Aspergillus oryzae* HowB101 (described in patent WO9535385 example 1) protoplasts were prepared according to the method of Christensen et al., 1988, Bio/Technology 6: 1419-1422. Three µg of plasmid pHi were used to transform *Aspergillus oryzae* HowB101.

The transformation of *Aspergillus oryzae* HowB101 with plasmid pHi yielded about 50 transformants for each transformation. Eight transformants were isolated to individual Minimal medium plates.

Four transformants from each transformation were inoculated separately into 3 ml of YPM medium in 24-well plate and incubated at 30° C., 150 rpm. After 3 days incubation, 20 µl of supernatant from each culture were analyzed on NuPAGE Novex 4-12% Bis-Tris Gel w/MES (Invitrogen Corporation, Carlsbad, Calif., USA) according to the manufacturer's instructions. The resulting gel was stained with INSTANT BLUE™ (Expedeon Ltd., Babraham Cambridge, UK). SDS-PAGE profiles of the cultures showed expression with protein bands detected. The size of major band of the gene was around 80 KD. The expression strain was designated as O5.

Example 18

Fermentation of Expression Strain O5

A slant of the expression strain, O5, was washed with 10 ml of YPM and inoculated into twelve 2-liter flasks each containing 400 ml of YPM medium to generate broth for characterization of the enzyme. The culture was harvested on day 3 and filtered using a 0.45 µm DURAPORE Membrane (Millipore, Bedford, Mass., USA).

Example 19

Purification of Recombinant *Humicola insolens* Catalase from *Aspergillus oryzae* O5

4000 ml supernatant of the recombinant strain O5 was precipitated with ammonium sulfate (80% saturation) and re-dissolved in 50 ml 20 mM Bis-Tris buffer, pH6.0, then dialyzed against the same buffer and filtered through a 0.45 mm filter, the final volume was 140 ml. The solution was applied to a 40 ml Q SEPHAROSE® Fast Flow column (GE Healthcare, Buckinghamshire, UK) equilibrated in 20 mM Bis-Tris buffer, pH6.0, and the proteins was eluted with a linear NaCl gradient (0-0.25M). Fractions eluted with 0.2-0.5M NaCl were collected and further purified on a 40 ml Q SEPHAROSE® Fast Flow column (GE Healthcare, Buckinghamshire, UK) equilibrated in 20 mM Bis-Tris buffer, pH6.0, and the proteins was eluted with a linear NaCl gradient (0.2-0.5M). Fractions were evaluated by SDS-PAGE (NP0336BOX, NUPAGE 4-12% BT GEL 1.5MM15W). Fractions containing a band of approximately 80 kDa were pooled. Then the pooled solution was concentrated by ultrafiltration.

The mature polypeptide of the *Humicola insolens* catalase shares 99.25% identity with the mature polypeptide of *Humicola grisea* thermotolerant catalase protein (WO2009104622-A1).

Example 20

Catalase Activity Assay

The purified *Humicola insolens* catalase was checked for catalase activity by using the following protocol.

The substrate was prepared by 1000 times dilution of 30% $H_2O_2$ (from Xilong Chemical, Guangdong, China) with double distilled $H_2O$ (dd$H_2O$), the final concentration was 10.3 mM. The reaction was started by adding 1 µl of purified *Humicola insolens* catalase sample into 1000 µl of substrate. The optical density (OD) at 240 nm was read by Ultrospec 3300 (GE Healthcare, Buckinghamshire, UK) at second of 0 and 16 respectively, and the decrease of the OD (from 0.400 to 0.102) showed the relative activity of the *Humicola insolens* catalase.

Example 21

*Penicillium emersonii* Genomic DNA Extraction

*Penicillium emersonii* strain NN051602 was inoculated onto a PDA plate and incubated for 3 days at 45° C. in the darkness. Several mycelia-PDA plugs were inoculated into 500 ml shake flasks containing 100 ml of YPG medium. The flasks were incubated for 3 days at 45° C. with shaking at 160 rpm. The mycelia were collected by filtration through MIRACLOTH® (Calbiochem, La Jolla, Calif., USA) and frozen in liquid nitrogen. Frozen mycelia were ground, by a mortar and a pestle, to a fine powder, and genomic DNA was isolated using a Large-Scale Column Fungal DNAout (Baoman Biotechnology, Shanghai, China) according to the manufacturer's instructions.

Example 22

Genome Sequencing, Assembly and Annotation

The extracted genomic DNA samples were delivered to Beijing Genome Institute (BGI, Shenzhen, China) for genome sequencing using ILLUMINA® GA2 System (Illumina, Inc., San Diego, Calif, USA). The raw reads were assembled at BGI using program SOAPdenovo (Li et al., 2010, Genome Res 20: 265-72). The assembled sequences were analyzed using standard bioinformatics methods for gene identification and functional prediction. Briefly, geneID (Parra et al., 2000, Genome Research 10(4):511-515) was used for gene prediction. Blastall version 2.2.10 (Altschul et al., 1990, J. Mol. Biol. 215 (3): 403-410, available on the internet at hypertext transfer protocol world wide web address blast.ncbi.nlm.nih.gov/Blast.cgi) and HMMER version 2.1.1 (National Center for Biotechnology Information (NCBI), Bethesda, Md., USA, available on the internet at hypertext transfer protocol world wide web address hmmr.janelia.org) were used to predict function based on structural homology. The catalase was identified by analysis of the Blast results. The Agene program (Munch and Krogh, 2006, BMC Bioinformatics 7:263) and SignalP program (Nielsen et al., 1997, Protein Engineering 10: 1-6) were used to identify start codons. SignalP was further used to predict the signal peptide. Pepstats (Rice et al., 2000, Trends Genet. 16 (6): 276-277) was used to estimate isoelectric point of proteins, and molecular weight.

Example 23

Cloning of the *Penicillium emersonii* Catalase from Genomic DNA

One catalase gene, PE04230007241 (SEQ ID NO: 7), was selected for expression cloning.

Based on the gene information obtained by genome sequencing, oligonucleotide primers as shown below, were designed to amplify the catalase gene, PE04230007241, from the genomic DNA of *Penicillium emersonii*. Primers were fabricated by Invitrogen (Invitrogen, Beijing, China).

```
Forward primer
                                       SEQ ID NO: 42
5' ACACAACTGGGGATCC ACC atgcgcgcagtgcagct 3'

Reverse primer
                                       SEQ ID NO: 43
5' GTCACCCTCTAGATCT gtcgactattccaaccttcctatatggac
ac 3'
```

Lowercase characters of the forward primer represent the coding regions of the gene and lowercase characters of the reverse primer represent the flanking region of the gene, while capitalized parts were homologous to the insertion sites of pPFJO355 vector which has been described in US2010306879.

An IN-FUSION™ CF Dry-down Cloning Kit (Clontech Laboratories, Inc., Mountain View, Calif., USA) was used to clone the fragment directly into the expression vector pPFJO355 which has been described in US2010306879, without the need for restriction digestion and ligation.

The expression vector pPFJO355 contains the TAKA-amylase promoter derived from *Aspergillus oryzae* and the *Aspergillus niger* glucoamylase terminator elements. Furthermore pPFJO355 has pUC18 derived sequences for selection and propagation in *E. coli*, and a pyrG gene, which encodes an orotidine decarboxylase derived from *Aspergillus nidulans* for selection of a transformant of a pyrG mutant *Aspergillus* strain.

Twenty picomoles of each of the primers above were used in a PCR reaction composed of 2 µl of *Penicillium* emersonii genomic DNA, 10 µl of 5×GC Buffer, 1.5 µl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 µl. The amplification was performed using a Peltier Thermal Cycler (MJ Research Inc., South San Francisco, Calif., USA) programmed for denaturing at 98° C. for 1 minutes; 8 cycles of denaturing at 98° C. for 15 seconds, annealing at 65° C. for 30 seconds, with 1° C. decrease per cycle and elongation at 72° C. for 3 minute 15 second; and another 22 cycles each at 98° C. for 15 seconds, 58 C for 30 seconds and 72° C. for 3 minute 15 second; final extension at 72° C. for 10 minutes. The heat block then went to a 4° C. soak cycle.

The reaction product was isolated by 1.0% agarose gel electrophoresis using 90 mM Tris-borate and 1 mM EDTA (TBE) buffer where an approximate 2.5 kb product band was excised from the gel, and purified using an ILLUSTRA™ GFX™ PCR DNA and Gel Band Purification Kit (GE Healthcare, Buckinghamshire, UK) according to the manufacturer's instructions.

Plasmid pPFJO355 was digested with Bam HI and Bgl 11, isolated by 1.0% agarose gel electrophoresis using TBE buffer, and purified using an ILLUSTRA™ GFX™ PCR DNA and Gel Band Purification Kit according to the manufacturer's instructions.

The PCR product and the digested vector were ligated together using an IN-FUSION™ CF Dry-down PCR Cloning resulting in pCat_PE04230007241 in which the transcription of the Penicillium emersonii catalase gene was under the control of a promoter from the gene for Aspergillus oryzae alpha-amylase. The cloning operation was conducted according to the manufacturer's instruction. In brief, 30 ng of pPFJO355 digested with Bam HI and Bgl II, and 60 ng of the purified Penicillium emersonii catalase gene PCR product were added to the reaction vial and resuspended the powder in a final volume of 10 µl with addition of deionized water. The reaction was incubated at 37° C. for 15 minutes and then 50° C. for 15 minutes. Three µl of the reaction products were used to transform E. coli TOP10 competent cells (TIANGEN Biotech (Beijing) Co. Ltd., Beijing, China). An E. coli transformant containing pCat_PE04230007241 was detected by colony PCR. Colony PCR is a method for quick screening of plasmid inserts directly from E. coli colonies. Briefly, in the premixed PCR solution aliquot in each PCR tube, including PCR buffer, $MgCl_2$, dNTPs, and primer pairs from which the PCR fragment was generated, a single colony was added by picking with a sterile tip and twirling the tip in the reaction solution. Normally 7-10 colonies were screened. After the PCR, reactions were analyzed by 1.0% agarose gel electrophoresis using TBE buffer. The plasmid DNA was prepared using a QIAprep Spin Miniprep Kit (QIAGEN Inc., Valencia, Calif., USA). The Penicillium emersonii catalase gene inserted in pCat_PE04230007241 was confirmed by DNA sequencing using a 3730XL DNA Analyzer (Applied Biosystems Inc, Foster City, Calif., USA).

Example 24

Expression of Penicillium emersonii Catalase Gene in Aspergillus oryzae

Aspergillus oryzae HowB101 (described in patent WO9535385 example 1) protoplasts were prepared according to the method of Christensen et al., 1988, Bio/Technology 6: 1419-1422. Three µg of pCat_PE04230007241 were used to transform Aspergillus oryzae HowB101.

The transformation of Aspergillus oryzae HowB101 with pCat_PE04230007241 yielded about 50 transformants. Four transformants were isolated to individual Minimal medium plates.

Four transformants were inoculated separately into 3 ml of YPM medium in 24-well plate and incubated at 30° C.,
150 rpm. After 3 days incubation, 20 µl of supernatant from each culture were analyzed on NuPAGE Novex 4-12% Bis-Tris Gel with 2-(N-morpholino)ethanesulfonic acid (MES) (Invitrogen Corporation, Carlsbad, Calif., USA) according to the manufacturer's instructions. The resulting gel was stained with INSTANT BLUE™ (Expedeon Ltd., Babraham Cambridge, UK). SDS-PAGE profiles of the cultures showed that all transformants had a band of approximately 80 kDa. The expression strain was designated as O6YTS.

Example 25

Fermentation of Aspergillus oryzae Expression Strain O6YTS

A slant of the expression strain, O6YTS, was washed with 10 ml of YPM and inoculated into 7 2-liter flasks containing 400 ml of YPM medium to generate broth for characterization of the enzyme. The culture was harvested on day 3 and filtered using a 0.45 µm DURAPORE Membrane (Millipore, Bedford, Mass., USA).

Example 26

Purification of Recombinant Penicillium emersonii Catalase from Aspergillus oryzae O6YTS 2800 ml supernatant of the recombinant strain O6YTS was precipitated with ammonium sulfate (80% saturation) and re-dissolved in 50 ml 20 mM Tris-HCl buffer, pH8.0, then dialyzed against the same buffer and filtered through a 0.45 mm filter, the final volume was 80 ml. The solution was applied to a 40 ml Q SEPHAROSE® Fast Flow column (GE Healthcare, Buckinghamshire, UK) equilibrated in 20 mM Tris-HCl buffer, pH8.0. Fractions eluted with 0.18-0.25M NaCl were evaluated by SDS-PAGE (NP0336BOX, NUPAGE 4-12% BT GEL 1.5MM15W). Fractions containing a band of approximately 80 kDa were pooled. Then the pooled solution was concentrated by ultrafiltration.

Example 27

Catalase Activity Assay

The purified Penicillium emersonii catalase was checked for catalase activity by using the following protocol.

The substrate was prepared by 1000 times dilution of 30% $H_2O_2$ (from Xilong Chemical, Guangdong, China) with double distilled $H_2O$ ($ddH_2O$), the final concentration was 10.3 mM. The reaction was started by adding 1 µl of purified Penicillium emersonii catalase sample into 1000 µl of substrate. The optical density (OD) at 240 nm was read by Ultrospec 3300 (GE Healthcare, Buckinghamshire, UK) at second of 0 and 16 respectively, and the decrease of the OD (from 0.505 to 0.284) showed the relative activity of the Penicillium emersonii catalase.

The present invention is further described by the following numbered paragraphs:

[1] A method for degrading or converting a cellulosic material, comprising: treating the cellulosic material with an enzyme composition in the presence of a polypeptide having catalase activity.

[2] The method of paragraph 1, wherein the enzyme composition comprises one or more (e.g., several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[3] The method of paragraph 2, wherein the cellulase is one or more (e.g., several) enzymes selected from the group consisting of an endoglucanase, a cellobiohydrolase, and a beta-glucosidase.

[4] The method of paragraph 2, wherein the hemicellulase is one or more enzymes selected from the group consisting of a xylanase, an acetylxylan esterase, a feruloyl esterase, an arabinofuranosidase, a xylosidase, and a glucuronidase.

[5] The method of any of paragraphs 1-4, wherein the cellulosic material is selected from the group consisting of agricultural residue, herbaceous material, municipal solid waste, pulp and paper mill residue, waste paper, and wood; preferably, arundo, bagasse, bamboo, corn cob, corn fiber, corn stover, miscanthus, orange peel, rice straw, switchgrass, wheat straw, eucalyptus, fir, pine, poplar, spruce, willow, algal cellulose, bacterial cellulose, cotton linter, filter paper, microcrystalline cellulose, or phosphoric-acid treated cellulose.

[6] The method of any of paragraphs 1-5, wherein the cellulosic material is pretreated, especially by chemical pretreatment, physical pretreatment, or biochemical pretreatment.

[7] The method of any of paragraphs 1-6, further comprising recovering the degraded cellulosic material.

[8] The method of paragraph 7, wherein the degraded cellulosic material is a sugar.

[9] The method of paragraph 8, wherein the sugar is selected from the group consisting of glucose, xylose, mannose, galactose, and arabinose.

[10] The method of any of paragraphs 1-9, wherein the presence of the polypeptide having catalase activity increases the hydrolysis of the cellulosic material compared to the absence of the polypeptide having catalase activity.

[11]. The method of any of paragraphs 1-10, wherein the polypeptide having catalase activity is selected from the group consisting of:

(a) a polypeptide having at least 60% sequence identity to the mature polypeptide of SEQ ID NO: 2, the mature polypeptide of SEQ ID NO: 4, the mature polypeptide of SEQ ID NO: 6, or the mature polypeptide of SEQ ID NO: 8;

(b) a polypeptide encoded by a polynucleotide that hybridizes under low, medium, medium-high, high, or very high stringency conditions with (i) the mature polypeptide coding sequence of SEQ ID NO: 1, SEQ ID NO: 3, SEQ ID NO: 5, or SEQ ID NO: 7, (ii) the cDNA sequence thereof, or (iii) the full-length complement of (i) or (ii);

(c) a polypeptide encoded by a polynucleotide having at least 60% sequence identity to the mature polypeptide coding sequence of SEQ ID NO: 1, the mature polypeptide coding sequence of SEQ ID NO: 3, the mature polypeptide coding sequence of SEQ ID NO: 5, or the mature polypeptide coding sequence of SEQ ID NO: 7; or the cDNA sequence thereof;

(d) a variant of the mature polypeptide of SEQ ID NO: 2, a variant of the mature polypeptide of SEQ ID NO: 4, a variant of the mature polypeptide of SEQ ID NO: 6, or a variant of the mature polypeptide of SEQ ID NO: 8, comprising a substitution, deletion, and/or insertion at one or more (e.g., several) positions; and (e) a fragment of the polypeptide of (a), (b), (c), or (d) that has catalase activity.

[12] The method of any of paragraphs 1-11, wherein the polypeptide having catalase activity is a catalase from *Thermoascus, Talaromyces, Humicola,* or *Penicillium*.

[13] The method of paragraph 12, wherein the polypeptide having catalase activity is a catalase from *Thermoascus aurantiacus, Talaromyces stipitatus, Humicola insolens,* or *Penicillium emersonii*.

[14] A method for producing a fermentation product, comprising:

(a) saccharifying a cellulosic material with an enzyme composition in the presence of a polypeptide having catalase activity;

(b) fermenting the saccharified cellulosic material with one or more (e.g., several) fermenting microorganisms to produce the fermentation product; and (c) recovering the fermentation product from the fermentation.

[15] The method of paragraph 14, wherein the enzyme composition comprises one or more (e.g., several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[16] The method of paragraph 15, wherein the cellulase is one or more (e.g., several) enzymes selected from the group consisting of an endoglucanase, a cellobiohydrolase, and a beta-glucosidase.

[17] The method of paragraph 15, wherein the hemicellulase is one or more enzymes selected from the group consisting of a xylanase, an acetylxylan esterase, a feruloyl esterase, an arabinofuranosidase, a xylosidase, and a glucuronidase.

[18] The method of any of paragraphs 14-17, wherein the cellulosic material is selected from the group consisting of agricultural residue, herbaceous material, municipal solid waste, pulp and paper mill residue, waste paper, and wood; preferably, arundo, bagasse, bamboo, corn cob, corn fiber, corn stover, miscanthus, orange peel, rice straw, switchgrass, wheat straw, eucalyptus, fir, pine, poplar, spruce, willow, algal cellulose, bacterial cellulose, cotton linter, filter paper, microcrystalline cellulose, or phosphoric-acid treated cellulose.

[19] The method of any of paragraphs 14-18, wherein the cellulosic material is pretreated, especially by chemical pretreatment, physical pretreatment, or biochemical pretreatment; or wherein steps (a) and (b) are performed simultaneously in a simultaneous saccharification and fermentation.

[20] The method of any of paragraphs 14-19, wherein the fermentation product is an alcohol, an alkane, a cycloalkane, an alkene, an amino acid, a gas, isoprene, a ketone, an organic acid, or polyketide.

[21] The method of any of paragraphs 14-20, wherein the presence of the polypeptide having catalase activity increases the hydrolysis of the cellulosic material compared to the absence of the polypeptide having catalase activity.

[22]. The method of any of paragraphs 14-21, wherein the polypeptide having catalase activity is selected from the group consisting of:

(a) a polypeptide having at least 60% sequence identity to the mature polypeptide of SEQ ID NO: 2, the mature polypeptide of SEQ ID NO: 4, the mature polypeptide of SEQ ID NO: 6, or the mature polypeptide of SEQ ID NO: 8;

(b) a polypeptide encoded by a polynucleotide that hybridizes under low, medium, medium-high, high, or very high stringency conditions with (i) the mature polypeptide coding sequence of SEQ ID NO: 1, SEQ ID NO: 3, SEQ ID NO: 5, or SEQ ID NO: 7, (ii) the cDNA sequence thereof, or (iii) the full-length complement of (i) or (ii);

(c) a polypeptide encoded by a polynucleotide having at least 60% sequence identity to the mature polypeptide coding sequence of SEQ ID NO: 1, the mature polypeptide coding sequence of SEQ ID NO: 3, the mature polypeptide coding sequence of SEQ ID NO: 5, or the mature polypeptide coding sequence of SEQ ID NO: 7; or the cDNA sequence thereof;

(d) a variant of the mature polypeptide of SEQ ID NO: 2, a variant of the mature polypeptide of SEQ ID NO: 4, a variant of the mature polypeptide of SEQ ID NO: 6, or a variant of the mature polypeptide of SEQ ID NO: 8, comprising a substitution, deletion, and/or insertion at one or more (e.g., several) positions; and (e) a fragment of the polypeptide of (a), (b), (c), or (d) that has catalase activity.

[23] The method of any of paragraphs 14-22, wherein the polypeptide having catalase activity is a catalase from *Thermoascus, Talaromyces, Humicola*, or *Penicillium*.

[24] The method of paragraph 23, wherein the polypeptide having catalase activity is a catalase from *Thermoascus aurantiacus, Talaromyces stipitatus, Humicola insolens*, or *Penicillium emersonii*.

[25] A method of fermenting a cellulosic material, comprising: fermenting the cellulosic material with one or more (e.g., several) fermenting microorganisms, wherein the cellulosic material is hydrolyzed with an enzyme composition in the presence of a polypeptide having catalase activity.

[26] The method of paragraph 25, wherein the enzyme composition comprises one or more (e.g., several) enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

[27] The method of paragraph 26, wherein the cellulase is one or more (e.g., several) enzymes selected from the group consisting of an endoglucanase, a cellobiohydrolase, and a beta-glucosidase.

[28] The method of paragraph 26, wherein the hemicellulase is one or more enzymes selected from the group consisting of a xylanase, an acetylxylan esterase, a feruloyl esterase, an arabinofuranosidase, a xylosidase, and a glucuronidase.

[29] The method of any of paragraphs 25-28, wherein the cellulosic material is selected from the group consisting of agricultural residue, herbaceous material, municipal solid waste, pulp and paper mill residue, waste paper, and wood; preferably, arundo, bagasse, bamboo, corn cob, corn fiber, corn stover, miscanthus, orange peel, rice straw, switchgrass, wheat straw, eucalyptus, fir, pine, poplar, spruce, willow, algal cellulose, bacterial cellulose, cotton linter, filter paper, microcrystalline cellulose, or phosphoric-acid treated cellulose.

[30] The method of any of paragraphs 25-29, wherein the cellulosic material is pretreated, especially by chemical pretreatment, physical pretreatment, or biochemical pretreatment.

[31] The method of any of paragraphs 25-30, wherein the fermentation produces a fermentation product.

[32] The method of paragraph 31, further comprising recovering the fermentation product.

[33] The method of paragraph 32, wherein the fermentation product is an alcohol, an alkane, a cycloalkane, an alkene, an amino acid, a gas, isoprene, a ketone, an organic acid, or polyketide.

[34] The method of any of paragraphs 25-33, wherein the presence of the polypeptide having catalase activity increases the hydrolysis of the cellulosic material compared to the absence of the polypeptide having catalase activity.

[35] The method of any of paragraphs 25-34, wherein the polypeptide having catalase activity is selected from the group consisting of:

(a) a polypeptide having at least 60% sequence identity to the mature polypeptide of SEQ ID NO: 2, the mature polypeptide of SEQ ID NO: 4, the mature polypeptide of SEQ ID NO: 6, or the mature polypeptide of SEQ ID NO: 8;

(b) a polypeptide encoded by a polynucleotide that hybridizes under low, medium, medium-high, high, or very high stringency conditions with (i) the mature polypeptide coding sequence of SEQ ID NO: 1, SEQ ID NO: 3, SEQ ID NO: 5, or SEQ ID NO: 7, (ii) the cDNA sequence thereof, or (iii) the full-length complement of (i) or (ii);

(c) a polypeptide encoded by a polynucleotide having at least 60% sequence identity to the mature polypeptide coding sequence of SEQ ID NO: 1, the mature polypeptide coding sequence of SEQ ID NO: 3, the mature polypeptide coding sequence of SEQ ID NO: 5, or the mature polypeptide coding sequence of SEQ ID NO: 7; or the cDNA sequence thereof;

(d) a variant of the mature polypeptide of SEQ ID NO: 2, a variant of the mature polypeptide of SEQ ID NO: 4, a variant of the mature polypeptide of SEQ ID NO: 6, or a variant of the mature polypeptide of SEQ ID NO: 8, comprising a substitution, deletion, and/or insertion at one or more (e.g., several) positions; and (e) a fragment of the polypeptide of (a), (b), (c), or (d) that has catalase activity.

[36] The method of any of paragraphs 25-35, wherein the polypeptide having catalase activity is a catalase from *Thermoascus, Talaromyces, Humicola*, or *Penicillium*.

[37] The method of paragraph 36, wherein the polypeptide having catalase activity is a catalase from *Thermoascus aurantiacus, Talaromyces stipitatus, Humicola insolens*, or *Penicillium emersonii*.

[38] An enzyme composition for degrading or converting a cellulosic material comprising one or more (e.g., several) enzymes having cellulolytic and/or hemicellulolytic activity and a polypeptide having catalase activity.

[39] The enzyme composition of paragraph 38, further comprising one or more (e.g., several) enzymes selected from the group consisting of a GH61 polypeptide having cellulolytic enhancing activity, an esterase, an expansin, a laccase, a ligninolytic enzyme, a pectinase, a peroxidase, a protease, and a swollenin.

[40] The enzyme composition of paragraph 38 or 39, wherein the enzymes having cellulolytic activity are selected from the group consisting of an endoglucanase, a cellobiohydrolase, and a beta-glucosidase.

[41] The enzyme composition of any of paragraphs 38-40, wherein the enzymes having hemicellulolytic activity are selected from the group consisting of a xylanase, an acetylxylan esterase, a feruloyl esterase, an arabinofuranosidase, a xylosidase, and a glucuronidase.

[42] The enzyme composition of any of paragraphs 38-41, wherein the polypeptide having catalase activity is selected from the group consisting of:

(a) a polypeptide having at least 60% sequence identity to the mature polypeptide of SEQ ID NO: 2, the mature polypeptide of SEQ ID NO: 4, the mature polypeptide of SEQ ID NO: 6, or the mature polypeptide of SEQ ID NO: 8;

(b) a polypeptide encoded by a polynucleotide that hybridizes under low, medium, medium-high, high, or very high stringency conditions with (i) the mature polypeptide coding sequence of SEQ ID NO: 1, SEQ ID NO: 3, SEQ ID NO: 5, or SEQ ID NO: 7, (ii) the cDNA sequence thereof, or (iii) the full-length complement of (i) or (ii);

(c) a polypeptide encoded by a polynucleotide having at least 60% sequence identity to the mature polypeptide coding sequence of SEQ ID NO: 1, the mature polypeptide coding sequence of SEQ ID NO: 3, the mature polypeptide coding sequence of SEQ ID NO: 5, or the mature polypeptide coding sequence of SEQ ID NO: 7; or the cDNA sequence thereof;

(d) a variant of the mature polypeptide of SEQ ID NO: 2, a variant of the mature polypeptide of SEQ ID NO: 4, a variant of the mature polypeptide of SEQ ID NO: 6, or a variant of the mature polypeptide of SEQ ID NO: 8, comprising a substitution, deletion, and/or insertion at one or more (e.g., several) positions; and (e) a fragment of the polypeptide of (a), (b), (c), or (d) that has catalase activity.

[43] The enzyme composition of any of paragraphs 38-42, wherein the polypeptide having catalase activity is a catalase from *Thermoascus, Talaromyces, Humicola,* or *Penicillium.*

[44] The enzyme composition of paragraph 43, wherein the polypeptide having catalase activity is a catalase from *Thermoascus aurantiacus, Talaromyces stipitatus, Humicola insolens,* or *Penicillium emersonii.*

[45] Use of the enzyme composition of any of paragraphs 38-44 in degrading or converting a cellulosic material.

[46] The use of paragraph 45, wherein the cellulosic material is selected from the group consisting of agricultural residue, herbaceous material, municipal solid waste, pulp and paper mill residue, waste paper, and wood; preferably, arundo, bagasse, bamboo, corn cob, corn fiber, corn stover, miscanthus, orange peel, rice straw, switchgrass, wheat straw, eucalyptus, fir, pine, poplar, spruce, willow, algal cellulose, bacterial cellulose, cotton linter, filter paper, microcrystalline cellulose, or phosphoric-acid treated cellulose.

[47] The use of paragraph 45 or 46, wherein the cellulosic material is pretreated, especially by chemical pretreatment, physical pretreatment, or biochemical pretreatment.

[48] A whole broth formulation or cell culture composition comprising one or more (e.g., several) enzymes having cellulolytic and/or hemicellulolytic activity and a polypeptide having catalase activity.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A method for degrading or converting a cellulosic material to fermentable sugars, comprising: treating the cellulosic material with an enzyme composition in the presence of a polypeptide having catalase activity, wherein the polypeptide having catalase activity is selected from the group consisting of:
   (a) a polypeptide having at least 70% sequence identity to the amino acid sequence of SEQ ID NO: 2 the sequence of amino acids 20 to 733 of SEQ ID NO: 4, or the sequence of amino acids 20 to 765 of SEQ ID NO: 6;
   (b) a polypeptide encoded by a polynucleotide that hybridizes under high stringency conditions with (i) the sequence of SEQ ID NO: 1, the nucleic acid sequence of nucleotides 58 to 2418 of SEQ ID NO: 3, or the nucleic acid sequence of nucleotides 58 to 3040 of SEQ ID NO: 5, (ii) the cDNA sequence thereof, or (iii) the full-length complement of (i) or (ii);
   (c) a polypeptide encoded by a polynucleotide having at least 70% sequence identity to the sequence of SEQ ID NO: 1,the nucleic acid sequence of nucleotides 58 to 2418 of SEQ ID NO: 3, the nucleic acid sequence of nucleotides 58 to 3040 of SEQ ID NO: 5, or the cDNA sequence thereof; and
   (d) a fragment of the polypeptide of (a), (b), or (c) that has catalase activity;
wherein the presence of the polypeptide having catalase activity increases the production of fermentable sugars, as compared to a degradation or conversion of a cellulosic material not in the presence of a polypeptide having catalase activity.

2. The method of claim 1, wherein the enzyme composition comprises one or more enzymes selected from the group consisting of a cellulase, a GH61 polypeptide having cellulolytic enhancing activity, a hemicellulase, an esterase, an expansin, a laccase, a ligninolytic enzyme, a pectinase, a peroxidase, a protease, and a swollenin.

3. The method of claim 1, wherein the cellulosic material is selected from the group consisting of agricultural residue, herbaceous material, municipal solid waste, pulp and paper mill residue, waste paper, and wood; preferably, arundo, bagasse, bamboo, corn cob, corn fiber, corn stover, miscanthus, orange peel, rice straw, switchgrass, wheat straw, eucalyptus, fir, pine, poplar, spruce, willow, algal cellulose, bacterial cellulose, cotton linter, filter paper, microcrystalline cellulose, or phosphoric-acid treated cellulose.

4. The method of claim 1, wherein the cellulosic material is pretreated, especially by chemical pretreatment, physical pretreatment, or biochemical pretreatment.

5. The method of claim 1, wherein the polypeptide has at least 80% sequence identity to SEQ ID NO: 2, the sequence of amino acids 20 to 733 of SEQ ID NO: 4, or the sequence of amino acids 20 to 765 of SEQ ID NO: 6.

6. The method of claim 1, wherein the polypeptide has at least 90% sequence identity to SEQ ID NO: 2, the sequence of amino acids 20 to 733 of SEQ ID NO: 4, or the sequence of amino acids 20 to 765 of SEQ ID NO: 6.

7. The method of claim 1, wherein the polypeptide has at least 95% sequence identity to SEQ ID NO: 2, the sequence of amino acids 20 to 733 of SEQ ID NO: 4, or the sequence of amino acids 20 to 765 of SEQ ID NO: 6.

8. The method of claim 1, wherein the polypeptide is encoded by a polynucleotide having at least 80% sequence identity to the nucleic acid sequence of SEQ ID NO: 1, the nucleic acid sequence of nucleotides 58to 2418 of SEQ ID NO: 3, or the nucleic acid sequence of nucleotides 58 to 3040 of SEQ ID NO: 5.

9. The method of claim 1, wherein the polypeptide is encoded by a polynucleotide having at least 90% sequence identity to the nucleic acid sequence of SEQ ID NO: 1 the nucleic acid sequence of nucleotides 58 to 2418 of SEQ ID NO: 3, or the nucleic acid sequence of nucleotides 58 to 3040 of SEQ ID NO: 5.

10. The method of claim 1, wherein the polypeptide is encoded by a polynucleotide having at least 95% sequence identity to the nucleic acid sequence of SEQ ID NO: 1 the nucleic acid sequence of nucleotides 58 to 2418 of SEQ ID NO: 3, or the nucleic acid sequence of nucleotides 58 to 3040 of SEQ ID NO: 5.

11. The method of claim 1, wherein the high stringency conditions are defined as prehybridization and hybridization at 42° C. in 5×SSPE, 0.3% SDS, 200 micrograms/mL sheared and denatured salmon sperm DNA, and 50% formamide, following standard Southern blotting procedures, followed by washing three times each for 15 minutes using 2×SSC, 0.2% SDS at 65° C.

\* \* \* \* \*